(12) United States Patent
McWeeney

(10) Patent No.: US 10,888,689 B2
(45) Date of Patent: *Jan. 12, 2021

(54) ENDOSCOPIC ULTRASOUND-GUIDED BILIARY ACCESS SYSTEM

(71) Applicant: COVIDIEN LP, Mansfield, MA (US)

(72) Inventor: John O. McWeeney, Brighton, MA (US)

(73) Assignee: Covidien LP, Mansfield, MA (US)

( * ) Notice: Subject to any disclaimer, the term of this patent is extended or adjusted under 35 U.S.C. 154(b) by 496 days.

This patent is subject to a terminal disclaimer.

(21) Appl. No.: 15/708,882

(22) Filed: Sep. 19, 2017

(65) Prior Publication Data

US 2018/0001057 A1    Jan. 4, 2018

Related U.S. Application Data

(63) Continuation of application No. 14/494,685, filed on Sep. 24, 2014, now Pat. No. 9,782,565, which is a (Continued)

(51) Int. Cl.
*A61B 5/00* (2006.01)
*A61M 25/01* (2006.01)
(Continued)

(52) U.S. Cl.
CPC ..... *A61M 25/0136* (2013.01); *A61B 10/0283* (2013.01); *A61B 10/04* (2013.01);
(Continued)

(58) Field of Classification Search
CPC ........... A61M 25/0136; A61B 10/0283; A61B 10/04; A61B 2010/045; A61B 17/3403;
(Continued)

(56) References Cited

U.S. PATENT DOCUMENTS 3,612,050 A   10/1971   Sheridan
3,666,808 A    5/1972   Meek
(Continued)

FOREIGN PATENT DOCUMENTS

EP   0704189 A1    4/1996
EP   0738501 A1   10/1996
(Continued)

OTHER PUBLICATIONS

Creganna Needle Brochure dated Jan. 16, 2008.
(Continued)

*Primary Examiner* — Max F Hindenburg
(74) *Attorney, Agent, or Firm* — Holland & Hart

(57) ABSTRACT

The present disclosure provides an access system having a maneuverable catheter assembly configured for providing access to and navigating a desired vessel for subsequent treatment thereof. The access system includes an adjustable delivery handle assembly and an access catheter subassembly having a maneuverable access catheter configured to be delivered to desired site (e.g., within duodenum) to assist in treatment of a condition (e.g., drainage of a bile ducts via Endoscopic Ultrasound Guided Biliary Drainage (EUS-BD) techniques). The access catheter includes at least a distal section having an adjustable portion along a length thereof configured to transition to a pre-defined arcuate shape to provide directional control over the distal end of the catheter as it is navigated through a vessel (e.g., bile duct). The handle assembly includes additional elements configured to allow a clinician to maneuver and manipulate the distal end of the access catheter.

16 Claims, 38 Drawing Sheets

Related U.S. Application Data continuation-in-part of application No. 13/297,766, filed on Nov. 16, 2011, now Pat. No. 9,332,973, which is a continuation-in-part of application No. 13/029,593, filed on Feb. 17, 2011, now abandoned, which is a continuation-in-part of application No. 12/607,636, filed on Oct. 28, 2009, now Pat. No. 8,968,210, which is a continuation-in-part of application No. 12/243,367, filed on Oct. 1, 2008, now Pat. No. 9,186,128.

(60) Provisional application No. 61/305,304, filed on Feb. 17, 2010, provisional application No. 61/305,396, filed on Feb. 17, 2010, provisional application No. 61/117,966, filed on Nov. 26, 2008, provisional application No. 61/152,741, filed on Feb. 16, 2009.

(51) Int. Cl.
*A61B 17/34* (2006.01)
*A61B 10/02* (2006.01)
*A61B 10/04* (2006.01)
A61B 17/00 (2006.01)
A61B 90/00 (2016.01)

(52) U.S. Cl.
CPC ...... *A61B 17/3403* (2013.01); *A61B 17/3415* (2013.01); *A61B 17/3423* (2013.01); *A61B 17/3478* (2013.01); *A61B 2010/045* (2013.01); *A61B 2017/00469* (2013.01); *A61B 2017/00477* (2013.01); *A61B 2017/00991* (2013.01); *A61B 2017/3413* (2013.01); *A61B 2017/3425* (2013.01); *A61B 2090/0801* (2016.02); *A61B 2090/3925* (2016.02); *A61M 2210/1021* (2013.01); *A61M 2210/1075* (2013.01)

(58) Field of Classification Search
CPC ............ A61B 17/3415; A61B 17/3423; A61B 17/3478
See application file for complete search history.

(56) References Cited

U.S. PATENT DOCUMENTS

| | | |
|---|---|---|
| 4,096,860 A | 6/1978 | McLaughlin |
| 4,249,541 A | 2/1981 | Pratt |
| 4,356,828 A | 11/1982 | Jamshidi |
| 4,467,816 A | 8/1984 | Schluter et al. |
| 4,655,226 A | 4/1987 | Lee |
| 4,819,637 A | 4/1989 | Dormandy, Jr. et al. |
| 4,838,280 A | 6/1989 | Haaga |
| 4,861,341 A | 8/1989 | Woodburn |
| 4,893,635 A | 1/1990 | de Groot et al. |
| 4,903,523 A | 2/1990 | Flynn |
| 4,966,162 A | 10/1990 | Wang |
| 4,995,866 A | 2/1991 | Amplatz et al. |
| 5,054,310 A | 10/1991 | Flynn |
| 5,057,085 A | 10/1991 | Kopans |
| 5,111,829 A | 5/1992 | Alvarez de Toledo |
| 5,131,393 A | 7/1992 | Ishiguro et al. |
| 5,167,239 A | 12/1992 | Cohen et al. |
| 5,215,528 A | 6/1993 | Purdy et al. |
| 5,257,628 A | 11/1993 | Ishiguro et al. |
| 5,266,359 A | 11/1993 | Spielvogel |
| 5,277,199 A | 1/1994 | DuBois et al. |
| 5,281,408 A | 1/1994 | Unger |
| 5,320,627 A | 6/1994 | Sorensen et al. |
| 5,333,613 A | 8/1994 | Tickner et al. |
| 5,368,036 A | 11/1994 | Tanaka et al. |
| 5,380,292 A | 1/1995 | Wilson |
| 5,385,561 A | 1/1995 | Cerny |
| 5,419,310 A | 5/1995 | Frassica et al. |
| 5,458,112 A | 10/1995 | Weaver |
| 5,470,308 A | 11/1995 | Edwards et al. |
| 5,471,988 A | 12/1995 | Fujio et al. |
| 5,480,389 A | 1/1996 | McWha et al. |
| 5,490,521 A | 2/1996 | Davis et al. |
| 5,526,822 A | 6/1996 | Burbank et al. |
| 5,595,562 A | 1/1997 | Grier |
| 5,595,724 A | 1/1997 | Deutsch et al. |
| 5,601,588 A | 2/1997 | Tonomura et al. |
| 5,607,389 A | 3/1997 | Edwards et al. |
| 5,609,850 A | 3/1997 | Deutsch et al. |
| 5,636,255 A | 6/1997 | Ellis |
| 5,681,348 A | 10/1997 | Sato |
| 5,688,490 A | 11/1997 | Tournier et al. |
| 5,695,491 A | 12/1997 | Silverstein |
| 5,775,333 A | 7/1998 | Burbank et al. |
| 5,800,445 A | 9/1998 | Ratcliff et al. |
| 5,801,057 A | 9/1998 | Smart et al. |
| 5,810,806 A | 9/1998 | Ritchart et al. |
| 5,810,835 A | 9/1998 | Ryan |
| 5,820,609 A | 10/1998 | Saito |
| 5,848,978 A | 12/1998 | Cecchi |
| 5,888,201 A | 3/1999 | Stinson et al. |
| 5,902,310 A | 5/1999 | Foerster et al. |
| 5,919,172 A | 7/1999 | Golba, Jr. |
| 5,921,933 A | 7/1999 | Sarkis et al. |
| 5,928,164 A | 7/1999 | Burbank et al. |
| 5,938,635 A | 8/1999 | Kuhle |
| 5,941,890 A | 8/1999 | Voegele et al. |
| 5,944,673 A | 8/1999 | Gregoire et al. |
| 5,947,964 A | 9/1999 | Eggers et al. |
| 5,964,740 A | 10/1999 | Ouchi |
| 5,967,988 A | 10/1999 | Briscoe et al. |
| 5,968,022 A | 10/1999 | Saito |
| 5,980,469 A | 11/1999 | Burbank et al. |
| 6,019,733 A | 2/2000 | Farascioni |
| 6,045,497 A | 4/2000 | Schweich, Jr. et al. |
| 6,080,115 A | 6/2000 | Rubinstein |
| 6,106,473 A | 8/2000 | Violante et al. |
| 6,106,524 A | 8/2000 | Eggers et al. |
| 6,117,108 A | 9/2000 | Woehr et al. |
| 6,126,633 A | 10/2000 | Kaji |
| 6,133,316 A | 10/2000 | Ostensen et al. |
| 6,149,598 A | 11/2000 | Tanaka |
| 6,161,034 A | 12/2000 | Burbank et al. |
| 6,168,779 B1 | 1/2001 | Barsky et al. |
| 6,171,249 B1 | 1/2001 | Chin et al. |
| 6,174,291 B1 | 1/2001 | McMahon et al. |
| 6,179,809 B1 | 1/2001 | Khairkhahan et al. |
| 6,190,360 B1 | 2/2001 | Iancea |
| 6,193,692 B1 | 2/2001 | Harris et al. |
| 6,203,507 B1 | 3/2001 | Wadsworth |
| 6,221,622 B1 | 4/2001 | Love |
| 6,228,039 B1 | 5/2001 | Binmoeller |
| 6,228,049 B1 | 5/2001 | Schroeder et al. |
| 6,231,515 B1 | 5/2001 | Moore et al. |
| 6,261,302 B1 | 7/2001 | Voegele et al. |
| 6,273,861 B1 | 8/2001 | Bates et al. |
| 6,280,399 B1 | 8/2001 | Rossin et al. |
| 6,287,304 B1 | 9/2001 | Eggers et al. |
| 6,312,428 B1 | 11/2001 | Eggers et al. |
| 6,323,335 B1 | 11/2001 | Huang |
| 6,328,701 B1 | 12/2001 | Terwilliger |
| 6,333,155 B1 | 12/2001 | Lockhart et al. |
| 6,334,067 B1 | 12/2001 | Brabrand |
| 6,336,812 B1 | 1/2002 | Cooper et al. |
| 6,337,994 B1 | 1/2002 | Stoianovici et al. |
| 6,338,968 B1 | 1/2002 | Hefti |
| 6,340,563 B1 | 1/2002 | Finkelstein et al. |
| 6,340,565 B1 | 1/2002 | Oliner et al. |
| 6,340,568 B2 | 1/2002 | Hefti |
| 6,344,316 B1 | 2/2002 | Lockhart et al. |
| 6,344,317 B2 | 2/2002 | Urnovitz |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,350,583 B1 | 2/2002 | Cohen et al. |
| 6,351,660 B1 | 2/2002 | Burke et al. |

(56) References Cited

U.S. PATENT DOCUMENTS

| | | |
|---|---|---|
| 6,355,033 B1 | 3/2002 | Moorman et al. |
| 6,355,275 B1 | 3/2002 | Klein |
| 6,355,424 B1 | 3/2002 | Lorincz et al. |
| 6,356,782 B1 | 3/2002 | Sirimanne et al. |
| 6,361,499 B1 | 3/2002 | Bates et al. |
| 6,361,948 B1 | 3/2002 | Tricoli et al. |
| 6,364,526 B2 | 4/2002 | Ivan et al. |
| 6,365,362 B1 | 4/2002 | Terstappen et al. |
| 6,365,712 B1 | 4/2002 | Kelly |
| 6,368,280 B1 | 4/2002 | Cermak et al. |
| 6,368,292 B1 | 4/2002 | Ogden et al. |
| 6,368,792 B1 | 4/2002 | Billing-Medel et al. |
| 6,368,795 B1 | 4/2002 | Hefti |
| 6,368,799 B1 | 4/2002 | Chee |
| 6,369,195 B1 | 4/2002 | An et al. |
| 6,371,904 B1 | 4/2002 | Sirimanne et al. |
| 6,371,917 B1 | 4/2002 | Ferrara et al. |
| 6,372,431 B1 | 4/2002 | Cunningham et al. |
| 6,372,444 B1 | 4/2002 | Powers et al. |
| 6,374,135 B1 | 4/2002 | Bucholz |
| 6,375,634 B1 | 4/2002 | Carroll |
| 6,375,953 B1 | 4/2002 | Srivastava et al. |
| 6,376,258 B2 | 4/2002 | Hefti |
| 6,379,671 B1 | 4/2002 | Colpitts |
| 6,379,672 B1 | 4/2002 | Srivastava et al. |
| 6,383,484 B1 | 5/2002 | Achen et al. |
| 6,383,491 B1 | 5/2002 | Srivastava et al. |
| 6,383,492 B1 | 5/2002 | Srivastava et al. |
| 6,383,493 B1 | 5/2002 | Srivastava et al. |
| 6,387,056 B1 | 5/2002 | Kieturakis |
| 6,387,374 B1 | 5/2002 | Srivastava et al. |
| 6,387,629 B1 | 5/2002 | Schneider et al. |
| 6,391,306 B1 | 5/2002 | Srivastava et al. |
| 6,391,542 B1 | 5/2002 | Anderson et al. |
| 6,391,543 B2 | 5/2002 | Billing-Medel et al. |
| 6,394,965 B1 | 5/2002 | Klein |
| 6,395,480 B1 | 5/2002 | Hefti |
| 6,398,737 B2 | 6/2002 | Moore et al. |
| 6,399,069 B1 | 6/2002 | Srivastava et al. |
| 6,399,070 B1 | 6/2002 | Srivastava et al. |
| 6,399,371 B1 | 6/2002 | Falduto et al. |
| 6,402,701 B1 | 6/2002 | Kaplan et al. |
| 6,403,095 B1 | 6/2002 | Srivastava et al. |
| 6,405,733 B1 | 6/2002 | Fogarty et al. |
| 6,407,125 B1 | 6/2002 | Fernandez-Pol |
| 6,409,664 B1 | 6/2002 | Kattan et al. |
| 6,410,028 B1 | 6/2002 | Srivastava |
| 6,410,229 B1 | 6/2002 | Lockhart et al. |
| 6,413,751 B1 | 7/2002 | Benkovic et al. |
| 6,416,484 B1 | 7/2002 | Miller et al. |
| 6,421,559 B1 | 7/2002 | Pearlman |
| 6,423,081 B1 | 7/2002 | Lee et al. |
| 6,423,313 B1 | 7/2002 | Esmon et al. |
| 6,423,489 B1 | 7/2002 | Anderson et al. |
| 6,423,494 B1 | 7/2002 | Jin et al. |
| 6,423,503 B1 | 7/2002 | Mikolajczyk et al. |
| 6,426,195 B1 | 7/2002 | Zhong et al. |
| 6,426,367 B1 | 7/2002 | Das |
| 6,427,081 B1 | 7/2002 | Burbank et al. |
| 6,427,089 B1 | 7/2002 | Knowlton |
| 6,428,463 B1 | 8/2002 | Ravins et al. |
| 6,428,479 B1 | 8/2002 | Aksnes et al. |
| 6,428,487 B1 | 8/2002 | Burdorff et al. |
| 6,432,035 B1 | 8/2002 | Ravins et al. |
| 6,432,053 B1 | 8/2002 | Fecht et al. |
| 6,432,065 B1 | 8/2002 | Burdorff et al. |
| 6,432,700 B1 | 8/2002 | Henderson et al. |
| 6,434,415 B1 | 8/2002 | Foley et al. |
| 6,436,054 B1 | 8/2002 | Viola et al. |
| 6,436,120 B1 | 8/2002 | Meglin |
| 6,436,394 B1 | 8/2002 | Henderson et al. |
| 6,436,404 B1 | 8/2002 | Srivastava et al. |
| 6,436,411 B1 | 8/2002 | Riordan et al. |
| 6,440,086 B1 | 8/2002 | Hohenberg |
| 6,440,147 B1 | 8/2002 | Lee et al. |
| 6,440,151 B1 | 8/2002 | Cragg et al. |
| 6,440,153 B2 | 8/2002 | Cragg et al. |
| 6,443,960 B1 | 9/2002 | Brabrand |
| 6,445,767 B1 | 9/2002 | Karellas |
| 6,447,477 B2 | 9/2002 | Burney et al. |
| 6,447,534 B2 | 9/2002 | Cragg et al. |
| 6,447,780 B1 | 9/2002 | Srivastava et al. |
| 6,447,781 B1 | 9/2002 | Srivastava |
| 6,447,997 B1 | 9/2002 | Los et al. |
| 6,448,020 B1 | 9/2002 | Toftgard et al. |
| 6,450,973 B1 | 9/2002 | Murphy |
| 6,455,027 B1 | 9/2002 | Barsky et al. |
| 6,455,048 B1 | 9/2002 | Srivastava et al. |
| 6,455,251 B1 | 9/2002 | Waldman |
| 6,459,925 B1 | 10/2002 | Nields et al. |
| 6,461,615 B1 | 10/2002 | Srivastava |
| 6,463,319 B1 | 10/2002 | Bucholz |
| 6,464,648 B1 | 10/2002 | Nakamura |
| 6,465,181 B2 | 10/2002 | Billing-Medel et al. |
| 6,465,183 B2 | 10/2002 | Wolber |
| 6,468,985 B1 | 10/2002 | Huang |
| 6,470,217 B1 | 10/2002 | Fenn et al. |
| 6,471,659 B2 | 10/2002 | Eggers et al. |
| 6,471,700 B1 | 10/2002 | Burbank et al. |
| 6,471,709 B1 | 10/2002 | Fawzi et al. |
| 6,472,518 B1 | 10/2002 | Ribot et al. |
| 6,475,732 B1 | 11/2002 | Shayesteh et al. |
| 6,475,789 B1 | 11/2002 | Cech et al. |
| 6,477,426 B1 | 11/2002 | Fenn et al. |
| 6,482,182 B1 | 11/2002 | Carroll et al. |
| 6,482,599 B1 | 11/2002 | Mikolajczyk et al. |
| 6,485,308 B1 | 11/2002 | Goldstein |
| 6,485,436 B1 | 11/2002 | Truckai et al. |
| 6,485,905 B2 | 11/2002 | Hefti |
| 6,488,636 B2 | 12/2002 | Bryan et al. |
| 6,489,097 B2 | 12/2002 | Hirose et al. |
| 6,489,113 B1 | 12/2002 | Traish |
| 6,490,467 B1 | 12/2002 | Bucholz et al. |
| 6,491,699 B1 | 12/2002 | Henderson et al. |
| 6,491,702 B2 | 12/2002 | Heilbrun et al. |
| 6,492,115 B1 | 12/2002 | Guida et al. |
| 6,494,844 B1 | 12/2002 | Van Bladel et al. |
| 6,494,859 B2 | 12/2002 | Love et al. |
| 6,494,879 B2 | 12/2002 | Lennox et al. |
| 6,495,130 B1 | 12/2002 | Henderson et al. |
| 6,496,717 B2 | 12/2002 | Cox et al. |
| 6,497,706 B1 | 12/2002 | Burbank et al. |
| 6,500,622 B2 | 12/2002 | Bruchez, Jr. et al. |
| 6,500,938 B1 | 12/2002 | Au-Young et al. |
| 6,505,125 B1 | 1/2003 | Ho |
| 6,506,156 B1 | 1/2003 | Jones et al. |
| 6,506,607 B1 | 1/2003 | Shyjan |
| 6,507,748 B2 | 1/2003 | Selland |
| 6,508,755 B1 | 1/2003 | Ravins et al. |
| 6,508,789 B1 | 1/2003 | Sinnott et al. |
| 6,509,458 B1 | 1/2003 | Afar et al. |
| 6,509,514 B1 | 1/2003 | Kneteman et al. |
| 6,514,248 B1 | 2/2003 | Eggers et al. |
| 6,514,251 B1 | 2/2003 | Ni et al. |
| 6,514,685 B1 | 2/2003 | Moro |
| 6,514,695 B1 | 2/2003 | Barsky et al. |
| 6,517,498 B1 | 2/2003 | Burbank et al. |
| 6,521,211 B1 | 2/2003 | Unger et al. |
| 6,524,800 B2 | 2/2003 | Lockhart et al. |
| 6,527,731 B2 | 3/2003 | Weiss et al. |
| 6,530,888 B2 | 3/2003 | Smith et al. |
| 6,535,756 B1 | 3/2003 | Simon et al. |
| 6,537,761 B1 | 3/2003 | Shayesteh et al. |
| 6,538,119 B2 | 3/2003 | Billing-Medel et al. |
| 6,540,694 B1 | 4/2003 | Van Bladel et al. |
| 6,540,695 B1 | 4/2003 | Burbank et al. |
| 6,544,236 B1 | 4/2003 | Cragg et al. |
| 6,544,544 B2 | 4/2003 | Hunter et al. |
| 6,546,787 B1 | 4/2003 | Schiller et al. |
| 6,548,257 B2 | 4/2003 | Lockhart et al. |
| 6,551,255 B2 | 4/2003 | Van Bladel et al. |
| 6,551,784 B2 | 4/2003 | Fodor et al. |
| 6,552,164 B1 | 4/2003 | Colpitts et al. |
| 6,552,181 B1 | 4/2003 | Dean et al. |

(56) References Cited

U.S. PATENT DOCUMENTS

| | | |
|---|---|---|
| 6,554,779 B2 | 4/2003 | Viola et al. |
| 6,558,407 B1 | 5/2003 | Ivanko et al. |
| 6,558,916 B2 | 5/2003 | Veerapandian et al. |
| 6,562,562 B2 | 5/2003 | Casu' et al. |
| 6,564,087 B1 | 5/2003 | Pitris et al. |
| 6,564,806 B1 | 5/2003 | Fogarty et al. |
| 6,566,078 B1 | 5/2003 | Raitano et al. |
| 6,566,079 B2 | 5/2003 | Hefti |
| 6,567,214 B2 | 5/2003 | Lorincz |
| 6,567,689 B2 | 5/2003 | Burbank et al. |
| 6,568,941 B1 | 5/2003 | Goldstein |
| 6,572,551 B1 | 6/2003 | Smith et al. |
| 6,572,578 B1 | 6/2003 | Blanchard |
| 6,577,904 B1 | 6/2003 | Zhang et al. |
| 6,579,891 B1 | 6/2003 | Fernandez-Pol |
| 6,580,938 B1 | 6/2003 | Acker |
| 6,582,368 B2 | 6/2003 | Holdaway et al. |
| 6,582,426 B2 | 6/2003 | Moorman et al. |
| 6,585,968 B2 | 7/2003 | Little et al. |
| 6,586,713 B2 | 7/2003 | Essenfeld et al. |
| 6,587,578 B2 | 7/2003 | Godik et al. |
| 6,589,240 B2 | 7/2003 | Hinchliffe |
| 6,592,508 B1 | 7/2003 | Ravins et al. |
| 6,592,530 B1 | 7/2003 | Farhadi |
| 6,599,247 B1 | 7/2003 | Stetten |
| 6,602,659 B1 | 8/2003 | Waldman et al. |
| 6,604,404 B2 | 8/2003 | Paltieli et al. |
| 6,605,294 B2 | 8/2003 | Sawhney |
| 6,607,561 B2 | 8/2003 | Brannon |
| 6,608,191 B1 | 8/2003 | Anderson et al. |
| 6,608,310 B2 | 8/2003 | Soluri et al. |
| 6,610,016 B1 | 8/2003 | Violante et al. |
| 6,610,499 B1 | 8/2003 | Fulwyler et al. |
| 6,610,839 B1 | 8/2003 | Morin et al. |
| 6,612,991 B2 | 9/2003 | Sauer et al. |
| 6,613,740 B1 | 9/2003 | Gozes et al. |
| 6,614,921 B1 | 9/2003 | Chung et al. |
| 6,617,110 B1 | 9/2003 | Chech et al. |
| 6,617,137 B2 | 9/2003 | Dean et al. |
| 6,623,437 B2 | 9/2003 | Hinchliffe et al. |
| 6,626,832 B1 | 9/2003 | Paltieli et al. |
| 6,626,848 B2 | 9/2003 | Neuenfeldt |
| 6,626,850 B1 | 9/2003 | Kupec et al. |
| 6,626,903 B2 | 9/2003 | McGuckin, Jr. et al. |
| 6,626,930 B1 | 9/2003 | Allen et al. |
| 6,627,414 B2 | 9/2003 | Billing-Medel et al. |
| 6,627,461 B2 | 9/2003 | Chapman et al. |
| 6,629,959 B2 | 10/2003 | Kuracina et al. |
| 6,631,204 B1 | 10/2003 | Smith |
| 6,632,183 B2 | 10/2003 | Bowman et al. |
| 6,638,234 B2 | 10/2003 | Burbank et al. |
| 6,638,719 B1 | 10/2003 | Gunderson et al. |
| 6,638,727 B1 | 10/2003 | Hung et al. |
| 6,645,731 B2 | 11/2003 | Terstappen et al. |
| 6,647,285 B2 | 11/2003 | Da Silva et al. |
| 6,649,420 B1 | 11/2003 | Cantor |
| 6,652,520 B2 | 11/2003 | Moorman et al. |
| 6,652,859 B1 | 11/2003 | Afar et al. |
| 6,653,080 B2 | 11/2003 | Bruchez et al. |
| 6,653,129 B1 | 11/2003 | Bander et al. |
| 6,654,120 B2 | 11/2003 | Ban |
| 6,654,629 B2 | 11/2003 | Montegrande |
| 6,656,132 B1 | 12/2003 | Ouchi |
| 6,659,105 B2 | 12/2003 | Burbank et al. |
| 6,660,834 B2 | 12/2003 | Billing-Medel et al. |
| 6,662,041 B2 | 12/2003 | Burbank et al. |
| 6,663,560 B2 | 12/2003 | MacAulay et al. |
| 6,666,811 B1 | 12/2003 | Good |
| 6,670,122 B2 | 12/2003 | Rosenow et al. |
| 6,673,023 B2 | 1/2004 | Pflueger |
| 6,673,914 B1 | 1/2004 | Hoon |
| 6,675,037 B1 | 1/2004 | Tsekos |
| 6,676,610 B2 | 1/2004 | Morton et al. |
| 6,676,658 B2 | 1/2004 | Burbank et al. |
| 6,676,935 B2 | 1/2004 | Henderson et al. |
| 6,676,984 B1 | 1/2004 | Sharp et al. |
| 6,677,157 B1 | 1/2004 | Cohen |
| 6,678,545 B2 | 1/2004 | Bucholz |
| 6,678,552 B2 | 1/2004 | Perlman |
| 6,679,851 B2 | 1/2004 | Burbank et al. |
| 6,680,178 B2 | 1/2004 | Harris et al. |
| 6,689,062 B1 | 2/2004 | Mesallum |
| 6,689,065 B2 | 2/2004 | Aksnes et al. |
| 6,689,067 B2 | 2/2004 | Sauer et al. |
| 6,689,071 B2 | 2/2004 | Burbank et al. |
| 6,689,072 B2 | 2/2004 | Kaplan et al. |
| 6,689,073 B2 | 2/2004 | Quay |
| 6,689,744 B2 | 2/2004 | Gao et al. |
| 6,689,787 B1 | 2/2004 | McKearn et al. |
| 6,690,371 B1 | 2/2004 | Okerlund et al. |
| 6,690,966 B1 | 2/2004 | Rava et al. |
| 6,690,976 B2 | 2/2004 | Fenn et al. |
| 6,692,467 B2 | 2/2004 | McFarlane |
| 6,692,724 B1 | 2/2004 | Yang et al. |
| 6,692,736 B2 | 2/2004 | Yu et al. |
| 6,695,779 B2 | 2/2004 | Sauer et al. |
| 6,697,665 B1 | 2/2004 | Rava et al. |
| 6,699,205 B2 | 3/2004 | Fulton, III et al. |
| 6,702,749 B2 | 3/2004 | Paladini et al. |
| 6,702,761 B1 | 3/2004 | Damadian et al. |
| 6,702,831 B2 | 3/2004 | Lee et al. |
| 6,703,216 B2 | 3/2004 | Parsons et al. |
| 6,705,994 B2 | 3/2004 | Vortman et al. |
| 6,709,408 B2 | 3/2004 | Fisher |
| 6,709,816 B1 | 3/2004 | Huang et al. |
| 6,712,773 B1 | 3/2004 | Viola |
| 6,712,785 B2 | 3/2004 | Morton et al. |
| 6,714,808 B2 | 3/2004 | Klimberg et al. |
| 6,716,179 B2 | 4/2004 | Burbank et al. |
| 6,722,371 B1 | 4/2004 | Fogarty et al. |
| 6,723,052 B2 | 4/2004 | Mills |
| 6,723,106 B1 | 4/2004 | Charles et al. |
| 6,723,498 B1 | 4/2004 | Shyjan et al. |
| 6,725,080 B2 | 4/2004 | Melkent et al. |
| 6,725,083 B1 | 4/2004 | Burbank et al. |
| 6,725,095 B2 | 4/2004 | Fenn et al. |
| 6,726,651 B1 | 4/2004 | Robinson et al. |
| 6,728,334 B1 | 4/2004 | Zhao |
| 6,730,042 B2 | 5/2004 | Fulton et al. |
| 6,730,045 B2 | 5/2004 | Finer |
| 6,731,966 B1 | 5/2004 | Spigelman et al. |
| 6,733,969 B2 | 5/2004 | Mack |
| 6,738,663 B2 | 5/2004 | Schroeppel et al. |
| 6,746,844 B2 | 6/2004 | Oliner et al. |
| 6,750,015 B2 | 6/2004 | Horwitz et al. |
| 6,752,154 B2 | 6/2004 | Fogarty et al. |
| 6,752,767 B2 | 6/2004 | Turovskiy et al. |
| 6,752,768 B2 | 6/2004 | Burdorff et al. |
| 6,752,769 B2 | 6/2004 | Alberico |
| 6,753,138 B1 | 6/2004 | Schneider et al. |
| 6,758,848 B2 | 7/2004 | Burbank et al. |
| 6,764,449 B2 | 7/2004 | Lee et al. |
| 6,764,495 B2 | 7/2004 | Lee et al. |
| 6,766,186 B1 | 7/2004 | Hoyns et al. |
| 6,767,704 B2 | 7/2004 | Waldman et al. |
| 6,768,925 B2 | 7/2004 | Fenn et al. |
| 6,770,066 B1 | 8/2004 | Weaver et al. |
| 6,770,070 B1 | 8/2004 | Balbierz |
| 6,770,435 B1 | 8/2004 | Billing-Medel et al. |
| 6,770,770 B1 | 8/2004 | Baumann et al. |
| 6,773,903 B2 | 8/2004 | Bova |
| 6,776,757 B2 | 8/2004 | Larson et al. |
| 6,780,984 B2 | 8/2004 | Wang et al. |
| 6,785,410 B2 | 8/2004 | Vining et al. |
| 6,786,870 B2 | 9/2004 | Miyaki et al. |
| 6,788,977 B2 | 9/2004 | Fenn et al. |
| 6,790,185 B1 | 9/2004 | Fisher et al. |
| 6,797,477 B2 | 9/2004 | Guida et al. |
| 6,805,669 B2 | 10/2004 | Swanbom |
| 6,805,869 B2 | 10/2004 | Guo |
| 6,806,712 B2 | 10/2004 | Akgun |
| 6,807,444 B2 | 10/2004 | Tu et al. |
| 6,808,878 B1 | 10/2004 | Gray et al. |
| 6,818,184 B2 | 11/2004 | Fulwyler et al. |

(56) References Cited

U.S. PATENT DOCUMENTS

| | | |
|---|---|---|
| 6,818,750 B2 | 11/2004 | Reed |
| 6,819,785 B1 | 11/2004 | Vining et al. |
| 6,821,725 B1 | 11/2004 | Carrasco et al. |
| 6,824,780 B1 | 11/2004 | Devaux et al. |
| 6,824,974 B2 | 11/2004 | Pisharody et al. |
| 6,824,995 B1 | 11/2004 | Wu |
| 6,827,692 B2 | 12/2004 | Castellacci |
| 6,831,059 B2 | 12/2004 | Donovan |
| 6,832,111 B2 | 12/2004 | Tu et al. |
| 6,833,373 B1 | 12/2004 | McKearn et al. |
| 6,833,438 B1 | 12/2004 | Afar et al. |
| 6,835,183 B2 | 12/2004 | Lennox et al. |
| 6,835,572 B1 | 12/2004 | Mountford et al. |
| 6,838,243 B2 | 1/2005 | Lai et al. |
| 6,840,952 B2 | 1/2005 | Saker et al. |
| 6,841,350 B2 | 1/2005 | Ogden et al. |
| 6,843,980 B2 | 1/2005 | Green |
| 6,844,153 B2 | 1/2005 | Waldman et al. |
| 6,846,320 B2 | 1/2005 | Ashby et al. |
| 6,846,650 B2 | 1/2005 | Recipon et al. |
| 6,846,911 B2 | 1/2005 | Kelly |
| 6,847,841 B1 | 1/2005 | El Hatw |
| 6,849,080 B2 | 2/2005 | Lee et al. |
| 6,850,588 B2 | 2/2005 | Arenson et al. |
| 6,852,528 B2 | 2/2005 | Yu et al. |
| 6,855,517 B2 | 2/2005 | Salceda et al. |
| 6,855,554 B2 | 2/2005 | Fritsche et al. |
| 6,858,412 B2 | 2/2005 | Willis et al. |
| 6,858,598 B1 | 2/2005 | McKearn et al. |
| 6,858,711 B2 | 2/2005 | McGall et al. |
| 6,859,049 B2 | 2/2005 | Khatchatrian et al. |
| 6,860,855 B2 | 3/2005 | Shelby et al. |
| 6,860,860 B2 | 3/2005 | Viola |
| 6,863,676 B2 | 3/2005 | Lee et al. |
| 6,864,224 B1 | 3/2005 | Sedivy et al. |
| 6,866,630 B2 | 3/2005 | Larson et al. |
| 6,866,993 B1 | 3/2005 | Williamson |
| 6,866,994 B2 | 3/2005 | Morton |
| 6,867,016 B1 | 3/2005 | Billing-Medel et al. |
| 6,867,753 B2 | 3/2005 | Chinthammit et al. |
| 6,871,086 B2 | 3/2005 | Nevo et al. |
| 6,872,184 B2 | 3/2005 | Brannon |
| 6,872,185 B2 | 3/2005 | Fisher |
| 6,872,389 B1 | 3/2005 | Faris |
| 6,875,182 B2 | 4/2005 | Wardle et al. |
| 6,875,184 B2 | 4/2005 | Morton et al. |
| 6,883,194 B2 | 4/2005 | Corbeil et al. |
| 6,883,958 B2 | 4/2005 | Mayer |
| 6,884,578 B2 | 4/2005 | Warrington et al. |
| 6,884,605 B2 | 4/2005 | Hermonat et al. |
| 6,887,210 B2 | 5/2005 | Quay |
| 6,888,919 B2 | 5/2005 | Graf |
| 6,890,308 B2 | 5/2005 | Islam |
| 6,890,309 B2 | 5/2005 | Fisher |
| 6,890,311 B2 | 5/2005 | Love et al. |
| 6,890,749 B2 | 5/2005 | Billing-Medel et al. |
| 6,893,818 B1 | 5/2005 | Afar et al. |
| 6,893,868 B2 | 5/2005 | Packard et al. |
| 6,894,026 B1 | 5/2005 | Quay |
| 6,899,696 B2 | 5/2005 | Morton et al. |
| 6,900,015 B2 | 5/2005 | Avihingsanon et al. |
| 6,900,049 B2 | 5/2005 | Yu et al. |
| 6,901,278 B1 | 5/2005 | Notelovitz |
| 6,904,305 B2 | 6/2005 | Tsekos |
| 6,904,309 B2 | 6/2005 | Derendorf et al. |
| 6,905,475 B2 | 6/2005 | Hauschild et al. |
| 6,908,440 B2 | 6/2005 | Fisher |
| 6,913,882 B2 | 7/2005 | Glynne et al. |
| 6,914,130 B2 | 7/2005 | Gao et al. |
| 6,916,800 B2 | 7/2005 | McKearn et al. |
| 6,916,918 B2 | 7/2005 | Yu et al. |
| 6,918,881 B2 | 7/2005 | Miller et al. |
| 6,919,176 B2 | 7/2005 | Yang et al. |
| 6,920,347 B2 | 7/2005 | Simon et al. |
| RE38,776 E | 8/2005 | Bauer |
| 6,923,809 B2 | 8/2005 | Eggers et al. |
| 6,924,094 B1 | 8/2005 | Gingeras et al. |
| 6,925,389 B2 | 8/2005 | Hitt et al. |
| 6,926,893 B1 | 8/2005 | Hansen |
| 6,927,032 B2 | 8/2005 | Lockhart et al. |
| 6,933,105 B2 | 8/2005 | Jin |
| 6,936,014 B2 | 8/2005 | Vetter et al. |
| 6,936,416 B2 | 8/2005 | Zhu et al. |
| 6,936,687 B1 | 8/2005 | Komoriya et al. |
| 6,942,985 B2 | 9/2005 | Waldman |
| 6,943,236 B2 | 9/2005 | Xu et al. |
| 6,944,505 B2 | 9/2005 | Zhang et al. |
| 6,945,942 B2 | 9/2005 | Van Bladel et al. |
| 6,947,584 B1 | 9/2005 | Avila et al. |
| 6,949,357 B2 | 9/2005 | Billing-Medel et al. |
| 6,953,691 B2 | 10/2005 | Reed et al. |
| 6,954,667 B2 | 10/2005 | Treado et al. |
| 6,955,653 B2 | 10/2005 | Eggers |
| 6,965,793 B2 | 11/2005 | Treado et al. |
| 6,994,712 B1 | 2/2006 | Fisher et al. |
| D518,175 S | 3/2006 | Hardin, Jr. et al. |
| 7,014,610 B2 | 3/2006 | Koulik |
| 7,025,765 B2 | 4/2006 | Balbierz et al. |
| 7,067,111 B1 | 6/2006 | Yang et al. |
| 7,067,274 B2 | 6/2006 | Fairbrother et al. |
| 7,070,816 B2 | 7/2006 | Newmark et al. |
| 7,072,704 B2 | 7/2006 | Bucholz |
| 7,074,600 B2 | 7/2006 | Dean et al. |
| 7,077,842 B1 | 7/2006 | Cosman |
| 7,079,132 B2 | 7/2006 | Sauer et al. |
| 7,081,340 B2 | 7/2006 | Baker et al. |
| 7,083,547 B2 | 8/2006 | LaStayo et al. |
| 7,083,985 B2 | 8/2006 | Hefti et al. |
| 7,087,393 B2 | 8/2006 | Billing-Medel et al. |
| 7,089,121 B1 | 8/2006 | Wang |
| 7,090,845 B2 | 8/2006 | Fong et al. |
| 7,090,862 B2 | 8/2006 | Barrett-Reis et al. |
| 7,091,047 B2 | 8/2006 | Serrero |
| 7,094,233 B2 | 8/2006 | Desinger |
| 7,101,663 B2 | 9/2006 | Godfrey et al. |
| 7,101,862 B2 | 9/2006 | Cochrum et al. |
| 7,108,969 B1 | 9/2006 | Warrington et al. |
| 7,115,368 B2 | 10/2006 | Powers et al. |
| 7,118,876 B2 | 10/2006 | Tyner et al. |
| 7,118,910 B2 | 10/2006 | Unger et al. |
| 7,122,011 B2 | 10/2006 | Clifford et al. |
| 7,122,653 B2 | 10/2006 | Cohen et al. |
| 7,125,836 B2 | 10/2006 | Woodward |
| 7,125,969 B1 | 10/2006 | Benz et al. |
| 7,128,877 B2 | 10/2006 | Quay et al. |
| 7,128,893 B2 | 10/2006 | Leamon et al. |
| 7,129,048 B2 | 10/2006 | Bruchez et al. |
| 7,131,951 B2 | 11/2006 | Angel |
| 7,135,333 B1 | 11/2006 | Waldman et al. |
| 7,139,601 B2 | 11/2006 | Bucholz et al. |
| 7,141,019 B2 | 11/2006 | Pearlman |
| 7,144,950 B2 | 12/2006 | Bazan et al. |
| 7,153,700 B1 | 12/2006 | Pardee et al. |
| 7,156,814 B1 | 1/2007 | Williamson, IV et al. |
| 7,156,815 B2 | 1/2007 | Leigh et al. |
| 7,160,292 B2 | 1/2007 | Moorman et al. |
| 7,161,057 B2 | 1/2007 | Kneteman et al. |
| 7,169,114 B2 | 1/2007 | Krause |
| 7,172,558 B2 | 2/2007 | Olson, Jr. |
| 7,172,739 B2 | 2/2007 | Maughan |
| 7,175,839 B1 | 2/2007 | Hiserodt |
| 7,183,251 B1 | 2/2007 | Russo et al. |
| D538,933 S | 3/2007 | Andrade |
| 7,186,522 B2 | 3/2007 | Lapen et al. |
| 7,189,206 B2 | 3/2007 | Quick et al. |
| 7,189,207 B2 | 3/2007 | Viola |
| 7,190,378 B2 | 3/2007 | Sauer et al. |
| 7,192,570 B2 | 3/2007 | Maecke et al. |
| 7,195,774 B2 | 3/2007 | Carvalho et al. |
| 7,195,868 B2 | 3/2007 | Iartchouk et al. |
| 7,195,911 B2 | 3/2007 | Cech et al. |
| 7,196,182 B2 | 3/2007 | Reed et al. |
| 7,198,896 B2 | 4/2007 | Rush et al. |
| 7,199,234 B2 | 4/2007 | Morin et al. |

(56) References Cited

U.S. PATENT DOCUMENTS

| | | |
|---|---|---|
| 7,204,988 B2 | 4/2007 | Cheung |
| 7,207,985 B2 | 4/2007 | Duong et al. |
| 7,208,146 B2 | 4/2007 | Denney, Jr. |
| 7,208,267 B2 | 4/2007 | Salceda et al. |
| 7,211,398 B2 | 5/2007 | Astle et al. |
| 7,214,489 B2 | 5/2007 | Bazan et al. |
| 7,217,276 B2 | 5/2007 | Henderson et al. |
| 7,217,394 B2 | 5/2007 | Studer |
| 7,218,959 B2 | 5/2007 | Alfano et al. |
| 7,220,258 B2 | 5/2007 | Myhr |
| 7,220,891 B2 | 5/2007 | Barsky et al. |
| 7,223,238 B2 | 5/2007 | Swanborn |
| 7,223,380 B2 | 5/2007 | Yang et al. |
| 7,223,540 B2 | 5/2007 | Pourmand et al. |
| 7,223,542 B2 | 5/2007 | Raitano et al. |
| 7,226,731 B1 | 6/2007 | Chuaqui et al. |
| 7,227,009 B2 | 6/2007 | Craik et al. |
| 7,229,413 B2 | 6/2007 | Violante et al. |
| 7,229,417 B2 | 6/2007 | Foerster et al. |
| 7,229,439 B2 | 6/2007 | Burbank et al. |
| 7,229,604 B2 | 6/2007 | Yang et al. |
| 7,229,774 B2 | 6/2007 | Chinnaiyan et al. |
| 7,231,015 B2 | 6/2007 | Kumakhov |
| 7,235,047 B2 | 6/2007 | MacAulay et al. |
| 7,236,816 B2 | 6/2007 | Kumar et al. |
| 7,241,736 B2 | 7/2007 | Hunter et al. |
| 7,244,619 B2 | 7/2007 | Contreras et al. |
| 7,245,748 B2 | 7/2007 | Degani et al. |
| 7,245,958 B1 | 7/2007 | Navab et al. |
| 7,247,426 B2 | 7/2007 | Yakhini et al. |
| 7,250,180 B2 | 7/2007 | Arellano |
| 7,250,264 B2 | 7/2007 | Fong et al. |
| 7,250,551 B2 | 7/2007 | Tsai et al. |
| 7,251,352 B2 | 7/2007 | Sauer et al. |
| 7,251,568 B2 | 7/2007 | Pittman et al. |
| 7,252,935 B2 | 8/2007 | Sidransky |
| 7,252,946 B2 | 8/2007 | Szasz |
| 7,252,948 B2 | 8/2007 | Gingeras et al. |
| 7,258,973 B2 | 8/2007 | Astle et al. |
| 7,261,712 B2 | 8/2007 | Burbank et al. |
| 7,261,875 B2 | 8/2007 | Li et al. |
| 7,262,288 B1 | 8/2007 | Cech et al. |
| 7,264,947 B2 | 9/2007 | Gozes et al. |
| 7,270,956 B2 | 9/2007 | Bazan et al. |
| 7,271,187 B2 | 9/2007 | Neuberger et al. |
| 7,274,810 B2 | 9/2007 | Reeves et al. |
| 7,314,481 B2 | 1/2008 | Karpiel |
| 7,608,056 B2 | 10/2009 | Kennedy, II |
| 8,109,953 B1 | 2/2012 | King, III et al. |
| D657,461 S | 4/2012 | Schembre et al. |
| 8,162,958 B2 | 4/2012 | Takahashi et al. |
| 8,187,203 B2 | 5/2012 | McClellan |
| 8,262,680 B2 | 9/2012 | Swain et al. |
| 8,328,772 B2 | 12/2012 | Kinast et al. |
| 8,357,193 B2 | 1/2013 | Phan et al. |
| 8,361,041 B2 | 1/2013 | Fang et al. |
| 8,454,632 B2 | 6/2013 | Binmoeller et al. |
| 8,486,010 B2 | 7/2013 | Nomura |
| D690,009 S | 9/2013 | Schembre et al. |
| 8,968,210 B2 | 3/2015 | Mugan et al. |
| 9,782,565 B2 * | 10/2017 | McWeeney ....... A61M 25/0136 |
| 2001/0007925 A1 | 7/2001 | Ritchart et al. |
| 2001/0023322 A1 | 9/2001 | Esposito et al. |
| 2001/0047183 A1 | 11/2001 | Privitera et al. |
| 2001/0056218 A1 | 12/2001 | Hogendijk et al. |
| 2002/0035324 A1 | 3/2002 | Sirimanne et al. |
| 2002/0082519 A1 | 6/2002 | Miller et al. |
| 2002/0156395 A1 | 10/2002 | Stephens et al. |
| 2002/0169418 A1 | 11/2002 | Menzi et al. |
| 2003/0078502 A1 | 4/2003 | Miyaki et al. |
| 2003/0093007 A1 | 5/2003 | Wood |
| 2003/0105488 A1 | 6/2003 | Chu |
| 2003/0139752 A1 | 7/2003 | Pasricha |
| 2003/0163142 A1 | 8/2003 | Paltieli et al. |
| 2003/0181823 A1 | 9/2003 | Gatto |
| 2003/0195436 A1 | 10/2003 | Van Bladel et al. |
| 2003/0204137 A1 | 10/2003 | Chesbrough et al. |
| 2003/0208134 A1 | 11/2003 | Secrest et al. |
| 2003/0208219 A1 | 11/2003 | Aznoian et al. |
| 2003/0212394 A1 | 11/2003 | Pearson et al. |
| 2003/0233101 A1 | 12/2003 | Lubock et al. |
| 2004/0073219 A1 | 4/2004 | Skiba et al. |
| 2004/0077948 A1 | 4/2004 | Violante et al. |
| 2004/0153005 A1 | 8/2004 | Krueger |
| 2004/0167429 A1 | 8/2004 | Roshdieh et al. |
| 2004/0236212 A1 | 11/2004 | Jones et al. |
| 2004/0249278 A1 | 12/2004 | Krause |
| 2004/0249395 A1 | 12/2004 | Mikkaichi et al. |
| 2004/0260199 A1 | 12/2004 | Hardia et al. |
| 2004/0260274 A1 | 12/2004 | Hardin |
| 2005/0021003 A1 | 1/2005 | Caso et al. |
| 2005/0022493 A1 | 2/2005 | Olinger et al. |
| 2005/0061697 A1 | 3/2005 | Moberg |
| 2005/0090801 A1 | 4/2005 | Racz et al. |
| 2005/0113715 A1 | 5/2005 | Schwindt et al. |
| 2005/0143753 A1 | 6/2005 | Whitmore et al. |
| 2005/0159676 A1 | 7/2005 | Taylor et al. |
| 2005/0192535 A1 | 9/2005 | Takagi et al. |
| 2005/0197623 A1 | 9/2005 | Leeflang |
| 2005/0228311 A1 | 10/2005 | Beckman et al. |
| 2005/0228312 A1 | 10/2005 | Surti |
| 2005/0228413 A1 | 10/2005 | Binmoeller et al. |
| 2005/0251111 A1 | 11/2005 | Saito et al. |
| 2005/0256426 A1 | 11/2005 | Brugge |
| 2005/0272975 A1 | 12/2005 | McWeeney et al. |
| 2006/0052750 A1 | 3/2006 | Lenker et al. |
| 2006/0100654 A1 | 5/2006 | Fukuda et al. |
| 2006/0116605 A1 | 6/2006 | Nakao |
| 2006/0142789 A1 | 6/2006 | Lehman et al. |
| 2006/0155210 A1 | 7/2006 | Beckman et al. |
| 2006/0167416 A1 | 7/2006 | Mathis et al. |
| 2006/0189891 A1 | 8/2006 | Waxman et al. |
| 2006/0235298 A1 | 10/2006 | Kotmel et al. |
| 2006/0247530 A1 | 11/2006 | Hardin et al. |
| 2006/0258955 A1 | 11/2006 | Hoffman et al. |
| 2006/0264919 A1 | 11/2006 | Schaaf |
| 2007/0023304 A1 | 2/2007 | Joyce et al. |
| 2007/0032741 A1 | 2/2007 | Hibner et al. |
| 2007/0038089 A1 | 2/2007 | Hatano et al. |
| 2007/0055173 A1 | 3/2007 | DeLonzor et al. |
| 2007/0056360 A1 | 3/2007 | Grant et al. |
| 2007/0060837 A1 | 3/2007 | Cho et al. |
| 2007/0118049 A1 | 5/2007 | Viola |
| 2007/0123799 A1 | 5/2007 | Meireles |
| 2007/0123800 A1 | 5/2007 | Nishtala et al. |
| 2007/0149893 A1 | 6/2007 | Heske et al. |
| 2007/0177009 A1 | 8/2007 | Bayer et al. |
| 2007/0179403 A1 | 8/2007 | Heske et al. |
| 2007/0185411 A1 | 8/2007 | Hibner |
| 2007/0213633 A1 | 9/2007 | McClellan |
| 2007/0213634 A1 | 9/2007 | Teague |
| 2007/0260258 A1 | 11/2007 | Sommerich |
| 2007/0282358 A1 | 12/2007 | Remiszewski |
| 2007/0299306 A1 | 12/2007 | Parasher et al. |
| 2008/0058637 A1 | 3/2008 | Fischell et al. |
| 2008/0097344 A1 | 4/2008 | McKinnon et al. |
| 2008/0097572 A1 | 4/2008 | Sheldon et al. |
| 2008/0146962 A1 | 6/2008 | Ritchie et al. |
| 2008/0147010 A1 | 6/2008 | Nakajima et al. |
| 2008/0200912 A1 | 8/2008 | Long |
| 2008/0294111 A1 | 11/2008 | Tal et al. |
| 2008/0300462 A1 | 12/2008 | Intoccia et al. |
| 2008/0319341 A1 | 12/2008 | Taylor et al. |
| 2009/0054773 A1 | 2/2009 | Shizuka |
| 2009/0064999 A1 | 3/2009 | Marten |
| 2009/0069679 A1 | 3/2009 | Hibi |
| 2009/0099414 A1 | 4/2009 | Goto et al. |
| 2009/0177114 A1 | 7/2009 | Chin et al. |
| 2009/0182200 A1 | 7/2009 | Golden et al. |
| 2009/0264794 A1 | 10/2009 | Kodama |
| 2009/0312645 A1 | 12/2009 | Weitzner |
| 2010/0081965 A1 | 4/2010 | Mugan et al. |
| 2010/0121218 A1 | 5/2010 | Mugan et al. |
| 2010/0274085 A1 | 10/2010 | Mugan et al. |

(56) References Cited

U.S. PATENT DOCUMENTS

| | | |
|---|---|---|
| 2011/0054381 A1 | 3/2011 | Van Dam et al. |
| 2011/0071350 A1 | 3/2011 | Van Dam et al. |
| 2011/0137394 A1 | 6/2011 | Lunsford et al. |
| 2011/0152886 A1 | 6/2011 | Sato et al. |
| 2012/0029278 A1 | 2/2012 | Sato et al. |
| 2012/0116248 A1 | 5/2012 | McWeeney et al. |
| 2012/0136426 A1 | 5/2012 | Phan et al. |
| 2012/0157880 A1 | 6/2012 | Haselby et al. |
| 2012/0172896 A1 | 7/2012 | Takahashi et al. |
| 2012/0245486 A1 | 9/2012 | Melchiorri et al. |
| 2012/0253228 A1 | 10/2012 | Schembre et al. |
| 2012/0296257 A1 | 11/2012 | Van Dam et al. |
| 2013/0041286 A1 | 2/2013 | Theobald et al. |
| 2013/0110141 A1 | 5/2013 | Chmura |
| 2013/0131547 A1 | 5/2013 | Hardert et al. |
| 2013/0131548 A1 | 5/2013 | McGhie et al. |
| 2013/0253546 A1 | 9/2013 | Sander et al. |
| 2013/0253550 A1 | 9/2013 | Beisel et al. |
| 2013/0310833 A1 | 11/2013 | Brown et al. |
| 2013/0325038 A1 | 12/2013 | Sato |
| 2014/0005478 A1 | 1/2014 | Kennedy, II et al. |
| 2014/0088684 A1 | 3/2014 | Paskar |

FOREIGN PATENT DOCUMENTS

| | | | |
|---|---|---|---|
| EP | 0739640 A1 | | 10/1996 |
| EP | 1870051 | | 12/2007 |
| EP | 2030574 A2 | | 3/2009 |
| EP | 09818508 | | 4/2010 |
| JP | 6-189965 A | | 7/1994 |
| JP | 7-116169 A | | 5/1995 |
| JP | 8-38482 A | | 2/1996 |
| JP | 9-135836 A | | 5/1997 |
| JP | 2003-245358 | | 9/2003 |
| JP | 2005-58431 | | 3/2005 |
| JP | 2006218070 | | 3/2006 |
| JP | 2007-513692 | | 5/2007 |
| JP | 2007-513692 A1 | | 5/2007 |
| JP | 201339219 | | 2/2013 |
| JP | 201494241 | | 5/2014 |
| WO | 86/005324 A1 | | 9/1986 |
| WO | 92/000039 A1 | | 1/1992 |
| WO | 92/04062 A1 | | 3/1992 |
| WO | 00/009178 A1 | | 2/2000 |
| WO | 00/33909 A1 | | 6/2000 |
| WO | 00/046626 A1 | | 8/2000 |
| WO | 2004/066828 A2 | | 8/2004 |
| WO | 2004/066829 A2 | | 8/2004 |
| WO | 2004/073509 A1 | | 9/2004 |
| WO | 2005/020905 A2 | | 3/2005 |
| WO | 2005060835 A2 | | 7/2005 |
| WO | 2005/081032 A1 | | 9/2005 |
| WO | 2005/081033 A1 | | 9/2005 |
| WO | 2005/096953 A2 | | 10/2005 |
| WO | 2005/096963 A2 | | 10/2005 |
| WO | 2005/112797 A1 | | 12/2005 |
| WO | 2005/120345 A2 | | 12/2005 |
| WO | 2006/014011 A1 | | 2/2006 |
| WO | 2006/028281 A1 | | 3/2006 |
| WO | 2006/057443 A1 | | 6/2006 |
| WO | 2006/064972 A1 | | 6/2006 |
| WO | 2007/021904 A2 | | 2/2007 |
| WO | 2007/021904 A3 | | 2/2007 |
| WO | 2007/081039 A2 | | 7/2007 |
| WO | 2007-081041 A1 | | 7/2007 |
| WO | 2007/081050 A1 | | 7/2007 |
| WO | 2007/081056 A1 | | 7/2007 |
| WO | 2008/020157 A1 | | 2/2008 |
| WO | 2008/020439 A2 | | 2/2008 |
| WO | 2008/024684 A2 | | 2/2008 |
| WO | 2008/044013 A2 | | 4/2008 |
| WO | 2010/039955 A2 | | 4/2010 |
| WO | 2010/062895 A2 | | 6/2010 |
| WO | 2012/112202 A1 | | 8/2012 |
| WO | 2013/074653 A1 | | 5/2013 |

OTHER PUBLICATIONS

Iglesias-Garcia, 2011, Feasibility and Yield of a New EUS Histology Needle; Results from a Multicenter, Pooled Cohort Study, Gastrointestinal Endoscopy 73(6); 1189-1196.

Iwashita, 2013, High Single-pass diagnostic yield of a New 25-gauge core biopsy needle for EUS-guided FNA biopsy in solid pancreatic lesions, Gastrointestinal Endoscopy 77(6); 909-915.

Kahaleh, 2013, Endoscopic Ultrasonography Guided biliary drainage: Summary of consortium meeting; May 7, 2011, Chicago, World Journal of Gastroenterology, 19(9); 1372-1379.

Khashab, 2013, EUS-guided biliary drainage by using a standardized approach for malignant biliary obstruction: rendezvous versus direct transluminal techniques, Gastrointestinal Endoscopy; 1-8.

Park, 2011, EUS-guided biliary drainage with transluminal stenting after failed ERCP: predictors of adverse events and long-term results, Gastrointestinal Endoscopy 74(6); 1276-1284.

Park, 2013, Prospective evaluation of a treatment algorithm with enhanced guidewire manipulation protocol for EUS-guided biliary drainage after failed ERCP, Gastrointestinal Endoscopy 78(1); 92-101.

Pelaez-Luna, 2008, Interventional EUS guided cholangiography. First description in Mexico of a novel, secure and feasible technique. A case report, Caso Clinico.

Examiner's Report for Canadian Application No. 2,995,281 dated Oct. 19, 2018.

\* cited by examiner

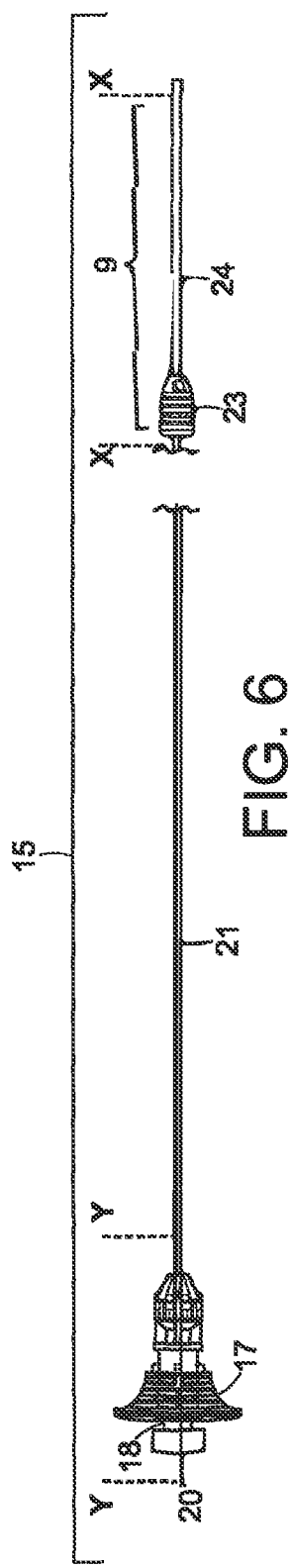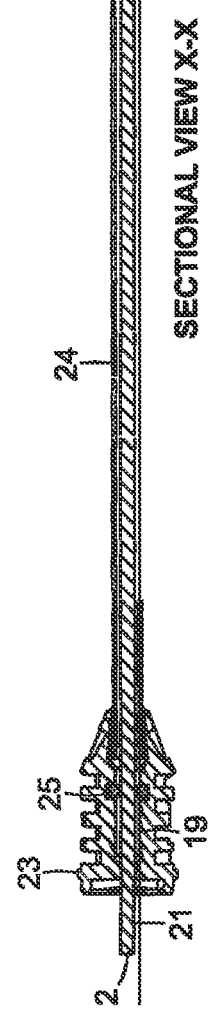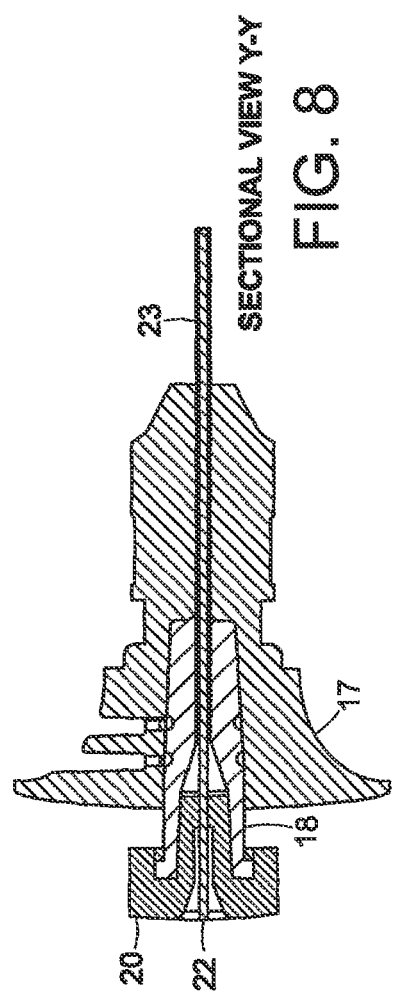
FIG. 6
SECTIONAL VIEW X-X
FIG. 7
SECTIONAL VIEW Y-Y
FIG. 8

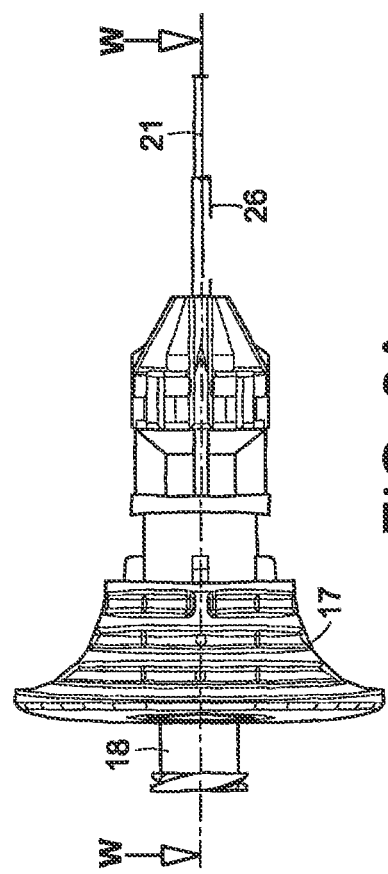
FIG. 8A
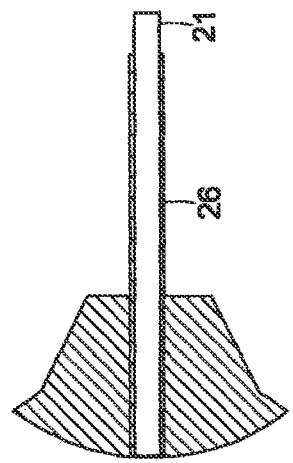
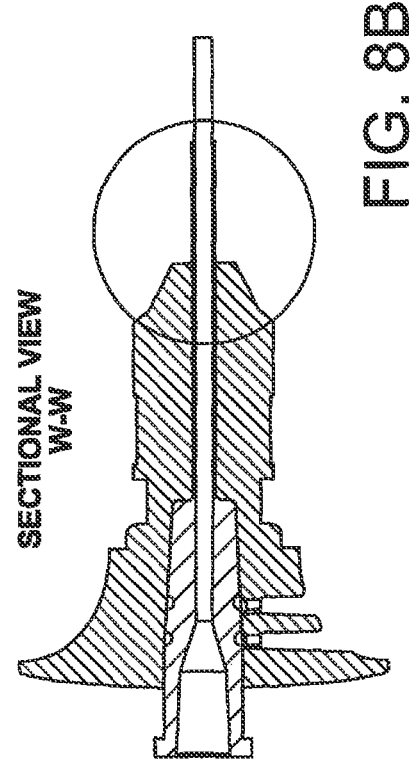
FIG. 8B

DETAIL C

DETAIL D

DETAIL E

SECTION A-A

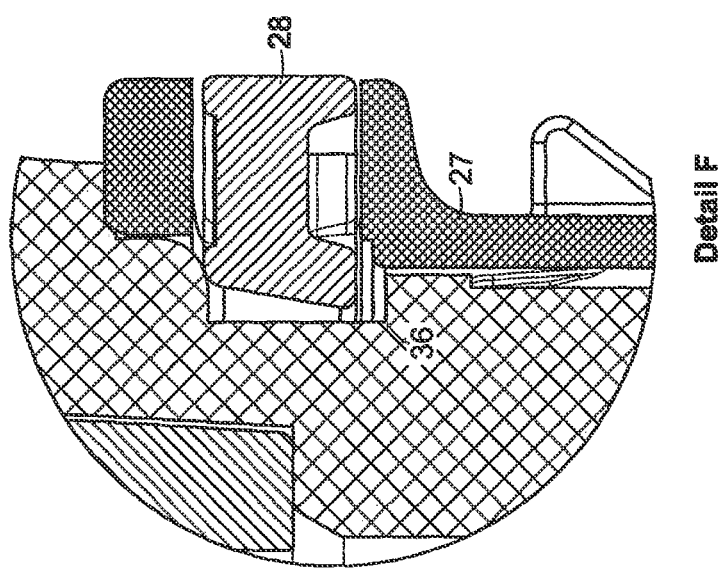
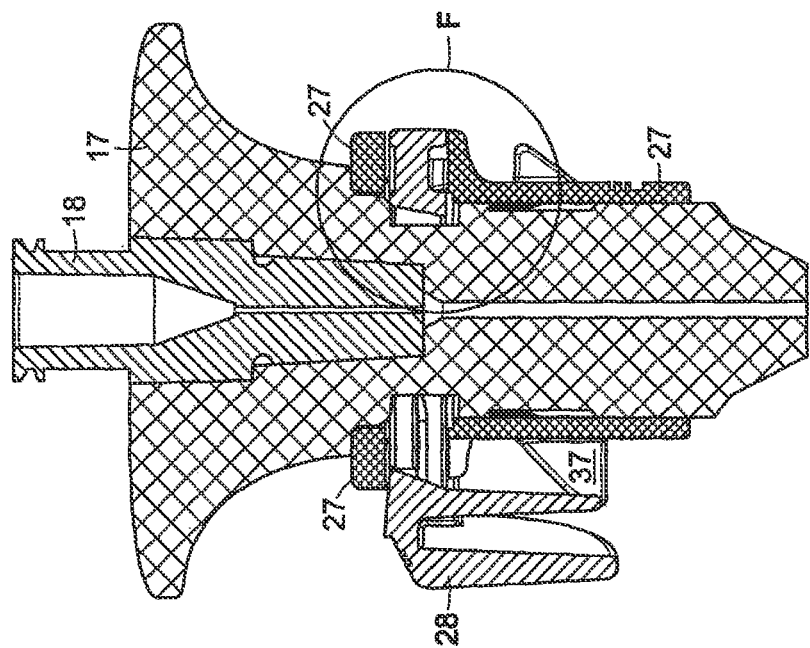
FIG. 23

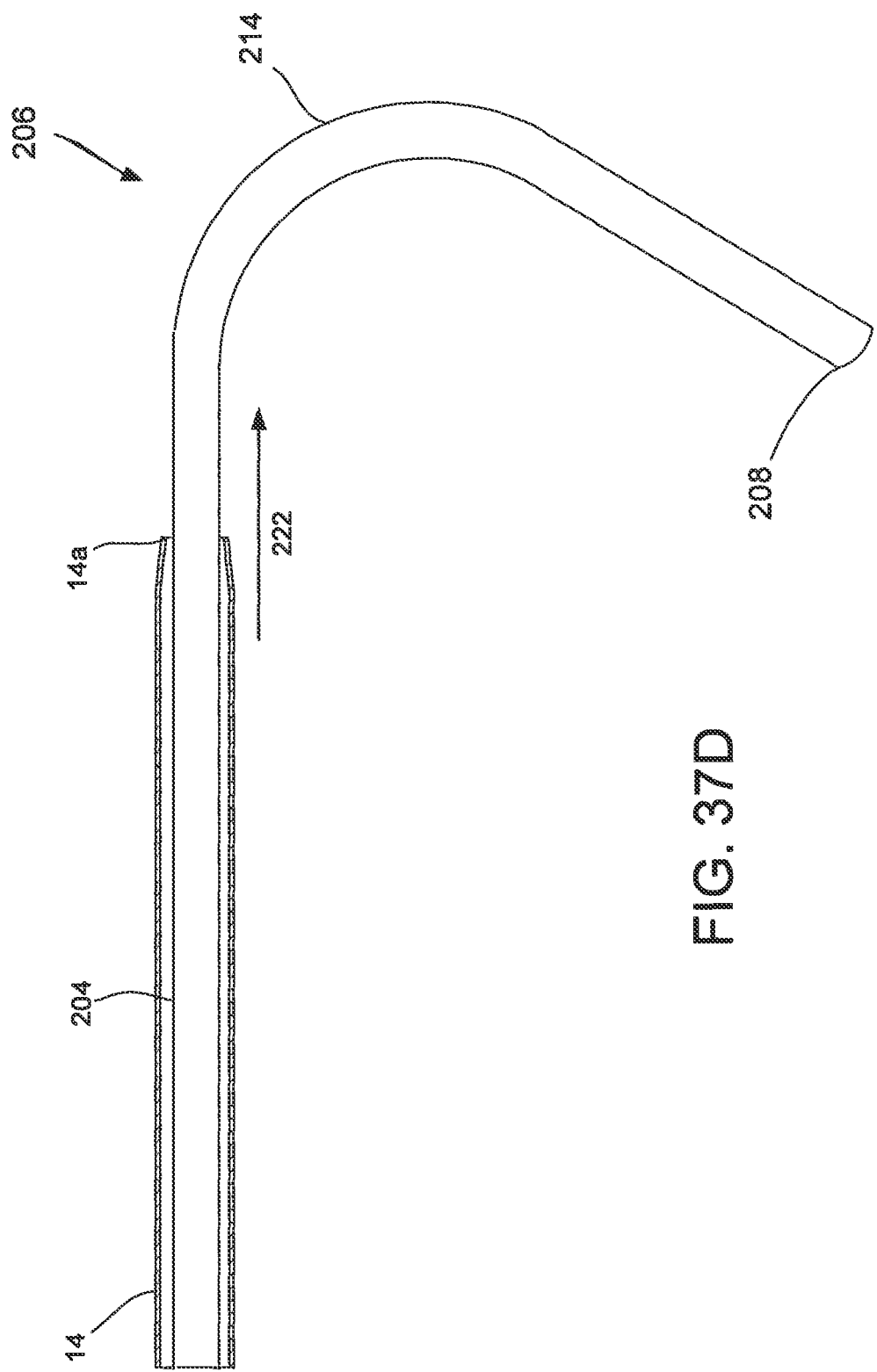

ENDOSCOPIC ULTRASOUND-GUIDED BILIARY ACCESS SYSTEM

CROSS-REFERENCE TO RELATED APPLICATIONS

This patent application is a continuation of U.S. patent application Ser. No. 14/494,685, filed Sep. 24, 2014, now U.S. Pat. No. 9,782,565, issued Oct. 10, 2017, which is a continuation-in-part of U.S. patent application Ser. No. 13/297,766, filed Nov. 16, 2011, now U.S. Pat. No. 9,332,973, issued May 10, 2016, which is a continuation-in-part of U.S. patent application Ser. No. 13/029,593, filed Feb. 17, 2011, which claims priority to and benefit of U.S. Provisional Application Ser. No. 61/305,304, filed Feb. 17, 2010, and U.S. provisional Application Ser. No. 61/305,396, filed Feb. 17, 2010.

U.S. patent application Ser. No. 13/029,593, filed Feb. 17, 2011, is also a continuation-in-part of U.S. patent application Ser. No. 12/607,636, filed Oct. 28, 2009, now U.S. Pat. No. 8,968,210, issued Mar. 3, 2015, which claims priority to and benefit of U.S. Provisional Application Ser. No. 61/117,966, filed Nov. 26, 2008.

U.S. patent application Ser. No. 13/029,593, filed Feb. 17, 2011, also claims priority to and benefit of U.S. Provisional Application Ser. No. 61/152,741, filed Feb. 16, 2009.

U.S. patent application Ser. No. 12/607,636, filed Oct. 28, 2009, now U.S. Pat. No. 8,968,210, issued Mar. 3, 2015, is also a continuation-in-part of U.S. patent application Ser. No. 12/243,367, filed Oct. 1, 2008, now U.S. Pat. No. 9,186,128, issued Nov. 17, 2015.

The entire contents of each of the above-mentioned applications are incorporated by reference herein in their entirety.

FIELD OF THE INVENTION

The present disclosure generally relates to minimally invasive access devices, and, more particularly, to an endoscopic ultrasound (EUS)-guided access system having a maneuverable catheter assembly configured for providing access to and navigating a desired vessel for subsequent treatment thereof.

BACKGROUND

Diseases and disorders of the gallbladder, pancreas, and bile ducts (e.g., pancreaticobiliary system) are associated with significant morbidity, mortality, and impaired quality of life. Obstructions, tumors, injuries, leakages, and lesions can occur in these structures, which can eventually lead to conditions such as biliary colic, cholecystitis, choledocholithiasis, cholelithiasis, pancreatitis, pancreatic duct stone formations, and chronic abdominal pain. In addition, diseases/disorders of the pancreaticobiliary system may be associated with nutritional disorders, such as malnutrition, obesity, as well as high cholesterol.

FIG. 1 illustrates a portion of the human body, including the pancreaticobiliary system. The liver 100 produces bile, a fluid vital for the digestion of fatty foods. Bile contains salts, cholesterol, various pigments, and waste products such as bilirubin. Bile serves at least two main functions: to get rid of certain waste products; and to aid in digestion by assisting in the emulsification and absorption of fats from the intestines. Bile is collected by a network of ducts that converge at the common hepatic duct 102. While a small quantity of bile drains directly into the lumen of the duodenum 120 (an upper part of the small intestine immediately downstream of the stomach), most bile travels through the common hepatic duct 102 and accumulates within the gallbladder 104. Contraction of the gallbladder 104 forces bile to flow from the gallbladder 104, through the cystic duct 106, and into a large bile duct known as the common bile duct 108. From the common bile duct 108, bile flows through the ampulla of Vater 118 and into the duodenum 120, where the bile mixes and reacts with digesting food.

The pancreas 114 is both an endocrine gland (producing several important hormones, including insulin, glucagon, and somatostatin), as well as an exocrine gland, secreting pancreatic juices containing digestive enzymes that pass to the small intestine. The pancreatic duct 112 joins the common bile duct 108 just prior to the ampulla of Vater 118. Accordingly, pancreatic juices drain through the ampulla of Vater 118 and into the duodenum to further aid in digestion.

The common bile duct and pancreatic duct are essential for providing drainage from the liver, gallbladder, and pancreas. However, in some cases, these ducts may become obstructed as a result of cysts, enlarged lymph nodes, gallstones, inflammation, stricture, or narrowing, of the ducts from scarring, injury from surgery, tumors, or other causes, which can lead to inadequate drainage of bile and/or pancreatic juices.

For example, as shown in FIG. 2, a common problem that arises in the biliary system is the formation of gallstones, a condition called cholelithiasis. Gallstones can form in the gallbladder 104, cystic duct 106, and/or the common bile duct 108. By themselves, gallstones 110 do not necessarily result in disease states. However, stones can cause infection and inflammation, a condition known as cholecystitis, which is generally the result of restricting or blocking the flow of bile from the gallbladder 104 and common bile duct 108, or the fluids secreted by the pancreas 114. When gallstones 110' become lodged in the common bile duct 108, the condition is known as choledocholithiasis. Symptoms for this condition include pain, nausea and vomiting, and some patients develop jaundice, have dark urine and/or lighter stools, rapid heartbeat, and experience an abrupt drop in blood pressure. Blockages in the bile ducts may also be caused by other obstructions, including, but not limited to, tumors, inflammation due to trauma or illness, such as pancreatitis, infection, improper opening of sphincter valves, lesions and/or scarring within the ducts, and/or pseudocysts (accumulations of fluid and tissue debris).

Complications from blockages within the bile ducts can very serious, and include infection of the common bile duct 108 (cholangitis) and inflammation of the pancreas 114 (pancreatitis) and potentially lead to death. Accordingly, it is important to address such a blockage so as to restore adequate drainage through the affected duct. In some cases, the obstruction may not be amenable to a surgical cure or bypass, and, instead, requires a palliative drainage procedure. A palliative drainage procedure is designed to prolong the life of the patient and to make the patient more comfortable when the condition of the patient is incurable.

In cases where a patient may have a biliary obstruction, Endoscopic Retrograde Cholangiopancreatography (ERCP) has been used by clinicians as the standard procedure to perform palliative biliary drainage over the more invasive Percutaneous Transhepatic Biliary Drainage ("PTBD") approach. The ERCP approach is an endoscopic procedure that combines upper gastrointestinal (GI) endoscopy and x-rays to treat problems of the bile and pancreatic ducts. For example, as shown in FIG. 3, during an ERCP procedure, an endoscope 122 is inserted into a patient's mouth, down the esophagus, into the stomach, passing into the lumen of the duodenum 120 to a position adjacent the ampulla of Vater 118. The endoscope 122 provides the initial access and direct visualization of the general area of treatment.

The endoscope 122 generally includes a proximal end (not shown), a distal end 124, and at least one lumen extending the length thereof. The distal end 124 of endoscope 120 generally includes a side opening in fluid communication with the lumen, such that additional medical devices may emerge from endoscope 122 from this side opening. It is these additional medical devices, which pass through endoscope 122, which are used to navigate and treat the abnormal pathologies within the desired duct. In particular, a biliary catheter 126 is advanced through endoscope 122 until the distal tip of biliary catheter 126 emerges from the endoscope 122 side opening and is advanced to the ampulla of Vater 118 leading to the common bile duct 108 and the pancreatic duct 112.

A guidewire (not shown) may be used in conjunction with biliary catheter 126 to aid in accessing a desired location within the biliary tree 128. For example, the guidewire is inserted in an opening at a proximal end of biliary catheter 126 and guided through the catheter lumen until it emerges from the distal end of the biliary catheter 126. The biliary catheter 126 is then advanced over the guidewire until the distal end of the catheter is positioned in the biliary tree 128 at the desired location. The biliary catheter 126 is now in a position for delivery of contrast media within the desired duct, wherein the contrast media allows for fluoroscopic visualization of anatomical detail within the biliary tree 128. The fluoroscopic visualization may reveal abnormalities and/or blockages within the common bile duct 108 that may require treatment, such as biliary drainage.

While ERCP enjoys a high success rate, biliary cannulation fails in approximately 5 to 20% of cases. For example, cannulation of the ampulla of Vater can be a daunting task for the clinician. In order to gain access to the ducts, the clinician must gently press the tip of the biliary catheter, or guidewire, into and through the opening of the ampulla of Vater. However, despite the best efforts of the clinician, cannulation of the ampulla of Vater will not occur through traditional "push-pull" techniques due to endoscopist inexperience, a distorted anatomy of the ampulla of Vater due to tumor invasion of the duodenum or ampulla, surgically altered anatomy, and/or complex biliary structures. In these instances, a clinician may probe the ampulla for an extended period of time with little success. Prolonged probing may further cause inflammation of the ampulla, wherein each attempt at cannulation increases trauma to the surrounding tissue, and subsequently, increases the discomfort experienced by the patient.

Advancements in the field of gastrointestinal endoscopy have provided clinicians with the ability to perform Endoscopic Ultrasound Guided Biliary Drainage (EUS-BD) in cases where traditional ERCP has failed or may not be administered. In particular, Endoscopic Ultrasound-Guided Fine-Needle Aspiration (EUS-FNA) has been used to cannulate a biliary duct via an EUS/ERCP rendezvous technique. For example, as shown in FIG. 4, under a rendezvous technique, a clinician may advance an EUS endoscope 122 into the lumen of a patient's duodenum 120 to a position in which bile ducts may be visualized (e.g., via endosonography). The clinician may then advance an FNA needle 130 into the common bile duct 108 under EUS guidance by puncturing trans-duodenally, as indicated by arrow 132. After confirmation of bile duct puncture, a guidewire 134 may then be advanced distally through the bile duct 108 and across the ampulla of Vater 118. When the guide wire has passed through the ampulla into the duodenum 120, an endoscope exchange is performed, wherein the EUS scope 122 is withdrawn, leaving the guidewire 134 in place, and a side-viewing endoscope (e.g., duodenoscope) is then passed into the duodenum 120 adjacent the EUS-placed guidewire 134. The guidewire 134 is then grasped with a snare or forceps for subsequent over-the-wire cannulation (e.g., via biliary catheter), upon which access to the common bile duct 108 is achieved and a standard ERCP procedure can then be performed (e.g., open blocked ducts, break up or remove gallstones, remove tumors in the ducts, insert stents, and/or endoscopic sphincterotomy). It should be noted that, in other EUS/ERCP rendezvous procedures, access to the common bile duct 108 is not limited to trans-duodenal access, as illustrated in FIG. 4. For example, access to the common bile duct 108 may be achieved trans-gastrically, such that the FNA needle 130 is advanced through the gastric wall of the stomach and into the common bile duct 108 under EUS guidance.

The EUS/ERCP rendezvous technique may be a preferred approach for many endoscopists because of the less invasive nature it provides, particularly for biliary drainage. However, this approach may have many drawbacks. For example, the rendezvous technique generally requires significant skill on behalf of the clinician due to a lack of currently available tools designed specifically for successful guidewire tracking. Specifically, current needle designs are rigid, thereby severely limiting the clinician's ability to direct the guidewire. Furthermore, biliary drainage via the rendezvous technique may not be possible if the guidewire is unable to be advanced through the ampulla because of difficult angulation or a tight distal biliary stricture. Accordingly, biliary drainage by needle rendezvous technique may require repeat punctures with different angles often resulting in a prolonged, labor-intensive procedure with the risk of shearing the guidewire and/or biliary leakage. Further difficulties currently observed by clinicians performing the EUS/ERCP rendezvous technique are difficulties advancing or directing the guidewire across an obstruction, difficulty achieving penetration into the biliary duct, clinical complications, such as pancreatitis, due to ductal trauma. Furthermore, the required scope exchange between EUS endoscope and an ERCP scope for guidewire retrieval can be cumbersome and plagued with difficulties.

SUMMARY

The present disclosure provides an endoscopic ultrasound (EUS)-guided access system having a maneuverable catheter assembly configured for providing access to and navigating a desired vessel for subsequent treatment thereof. In embodiments described herein, the access system is configured for providing access to one or more tissues/organs associated with the pancreaticobiliary system for the purpose of providing treatment. In particular, the access system described herein is configured to provide access to at least the common biliary duct via an Endoscopic Ultrasound-Guided Fine-Needle Aspiration (EUS-FNA) technique and to further allow procedures to treat narrowed areas or blockages within the bile duct, including palliative drainage procedures. Accordingly, the access system is configured to provide Endoscopic Ultrasound Guided Biliary Drainage (EUS-BD). However, it should be noted that the access system of the present invention is not limited to the pancreaticobiliary system. The access system of the present invention can be used to provide access to a variety of different systems of the human body, particularly where maneuverability and accuracy is desirable.

The access system of the present invention includes an adjustable delivery handle assembly and an access catheter subassembly configured to be delivered to a desired site and to further gain access to the site. The access catheter subassembly includes an access catheter having at least a distal section having an adjustable portion along a length thereof configured to transition to a pre-defined arcuate shape, particularly once deployed into a desired site, such as the common biliary duct. The pre-defined arcuate shape is configured to provide a clinician with directional control over the distal end of the catheter as it is navigated through the duct, wherein the internal anatomy of the duct may be complicated and narrow. In some embodiments, the access catheter may further include one or more cutting elements, such as a dielectric cautery ring and/or cutting knife configured to allow the clinician to ablate/cut through tissue so as to widen an obstructed pathway and/or completely remove a tumor or other obstruction (e.g., gallstone). Additionally, or alternatively, the access catheter may also have steerable functionality. For example, one or more control, or steering, wires may be positioned within and anchored to at least the distal section, such that a force applied to the one or more control wires results in manipulation of at least the distal end.

The handle assembly includes one or more elements configured to allow a clinician to maneuver and manipulate the distal end of the access catheter while navigating the vessel. In one embodiment, the handle assembly includes inner hub housing having a first plurality of radially-spaced barbs disposed on an inner diameter thereof and the access catheter subassembly further includes a catheter hub configured for insertion into the inner hub housing. The catheter hub has a second plurality of radially-spaced barbs disposed on an outer diameter thereof, wherein each of the second plurality of barbs are configured for selective engagement with a corresponding one of the first plurality of barbs to permit incremental rotation of the catheter hub relative to the inner hub housing. The access catheter is coupled to the catheter hub, such that, the distal section of the access catheter is configured to incrementally rotate about a longitudinal axis defined by the lumen of the catheter body in conjunction with incremental rotation of the catheter hub. Upon a clinician removing rotational force, engagement between the first and second barbs ensures that the distal section, particularly the adjustable portion, remains fixed the desired location and does not whip. As such, a clinician may remove their grip from the handle assembly, while the position of the distal section is maintained.

Accordingly, the access system of the present invention provides a clinician with the ability manipulate the adjustable portion of the distal section, particularly when the adjustable portion is in the pre-defined arcuate shape, thereby providing an increased overall range of motion to allow improved manipulation during navigation of a vessel. Thus, the access system of the present invention provides access to the appropriate vessel (e.g., biliary duct), allows manipulation of the catheter, as well as other tools (e.g., guidewire) into position so as to achieve trans-papillary placement (across the ampulla of Vater), and further achieve internal drainage of the biliary duct (e.g., via antegrade placement of a stent), all without having to perform a scope exchange (as current techniques require US scope to ERCP scope exchanges during rendezvous procedure for biliary duct drainage).

The access system of the present invention overcomes many of the drawbacks associated with the EUS/ERCP rendezvous technique. In particular, the pre-defined arcuate shape of the access catheter of the present invention provides improved initial access to the biliary duct, due in part to the initial trans-duodenal puncture, which occurs in a relatively orthogonal angle to the lumen of the biliary duct. Accordingly, upon initially accessing the biliary duct with the catheter, the pre-defined arcuate shape of the distal section results in the distal end of the catheter being aligned with the lumen of the biliary duct, such that guidewire advancement is improved and decreases the risk of injury to surrounding tissue when advancing a guidewire. Furthermore, the increased mobility of the access catheter, particularly the increased flexibility of the distal end, as well as improved manipulation of the distal end, not only in a rotational manner, but also in left, right, front, and back directions relative to the longitudinal axis of the catheter, improves the clinician's ability to navigate the lumen of the duct, and further advance past obstructions that may have been otherwise impassable with conventional catheters used in EUS/ERCP rendezvous technique.

In certain aspects, the present disclosure provides a system for providing access to a vessel. The system includes an adjustable delivery handle system including a delivery handle assembly, at least a portion of which includes an inner lumen configured to receive one of a plurality of exchangeable subassemblies. The delivery handle subassembly further includes a sheath coupled to a distal end of the handle assembly and having a lumen in fluid communication with the inner lumen of the delivery handle assembly. The system further includes an access catheter subassembly removably disposed within the inner lumen of the delivery handle assembly and lumen of the sheath. The access catheter includes an access catheter having an elongate tubular body having a proximal section having a proximal end, a distal section having a distal end, an outer surface, and an inner surface defining a lumen extending from the proximal end to the distal end. The distal section includes an adjustable portion along a length thereof configured to transition between a pre-defined arcuate shape and a substantially linear shape.

In some embodiments, when disposed within the lumen of the sheath, the adjustable portion of the distal section of the access catheter is configured to maintain a substantially linear shape. Upon extension from the lumen of the sheath, the adjustable portion of the distal section of the access catheter is configured to transition to the pre-defined arcuate shape. When in the pre-defined arcuate shape, the adjustable portion forms at least one angle relative to a longitudinal axis defined by the lumen of the catheter body, wherein the at least one angle is between 0 and 170 degrees.

In some embodiments, the system further includes a stylette member removably disposed within the inner lumen of the delivery handle assembly, lumen of the sheath, and lumen of the access catheter. The stylette member has a distal end configured to pierce tissue of a vessel to provide access to an interior of the vessel. When the stylette member is disposed within lumen of the adjustable portion of the distal section of the access catheter, the adjustable portion is configured to maintain a substantially linear shape. Upon removal of the stylette member from within the lumen of the adjustable portion, the adjustable portion is configured to transition to the pre-defined arcuate shape.

In some embodiments, the proximal section and the distal section of the access catheter have different levels of stiffness. For example, the proximal section has a greater level of stiffness than the distal section.

In some embodiments, the distal section of the access catheter further includes a portion adjacent the distal end having enhanced echogenicity or acoustic reflection, which may be particularly helpful in locating the distal section via ultrasound techniques. In some embodiments, the distal section of the access catheter has a metallic distal tip at a distal end.

The metallic distal tip may provide sufficient durability and strength for allowing the distal end to puncture through relatively tough and/or fibrous tissue, in which the distal end would deflect from without the metallic distal tip. In some embodiments, the distal section of the access catheter includes a tubular body formed from densely packed tubular coil. An interior surface of the lumen of the distal section has a liner disposed thereon having a relatively low coefficient of friction. Such a coiled configuration is configured to enhance flexibility for access catheter advancement while also enhancing torque transmission during manipulation.

In some embodiments, the delivery handle assembly further includes an inner hub housing coupled thereto. The inner hub housing having a first plurality of radially-spaced barbs disposed on an inner diameter thereof. The access catheter subassembly further includes a catheter hub configured for insertion into the inner hub housing, the catheter hub having a second plurality of radially-spaced barbs disposed on an outer diameter thereof. Each of the second plurality of barbs is configured for selective engagement with a corresponding one of the first plurality of barbs to permit incremental rotation of the catheter hub relative to the inner hub housing. The proximal section of the access catheter is coupled to the catheter hub, such that the distal section of the access catheter is configured to incrementally rotate about a longitudinal axis defined by the lumen of the catheter body in conjunction with incremental rotation of the catheter hub.

In some embodiments, the access catheter further includes a cutting element positioned on the distal section adjacent to the distal end. The cutting element may include a cautery ring or a cutting knife, or the like. In some embodiments, the access catheter further includes at least one control element configured to cause movement of at least the distal end relative to a longitudinal axis defined by the lumen of the catheter body upon application of force thereto. For example, the distal section of the catheter may be steerable upon application of force (e.g., tension) on control wires.

BRIEF DESCRIPTION OF THE DRAWINGS

FIG. 6 is a drawing of the aspiration needle sub-assembly of the present invention.

FIG. 7 is a cross sectional drawing of the needle protector embodiment of the present invention shown in FIG. 6.

FIG. 8 is a cross sectional drawing of the proximal end of the aspiration needle sub-assembly shown in FIG. 6.

FIG. 8A is a drawing of an alternate preferred embodiment of the proximal end of the aspiration needle sub-assembly with strain relief.

FIG. 8B is a cross sectional drawing of the proximal end of the aspiration needle sub-assembly with strain relief.

FIG. 23 is a cross-sectional drawing of locking functionality between the needle hub, thumb latch and hub housing components.

FIG. 37D is a side view, partly in section, of further extension of the access catheter from the sheath of FIG. 34, illustrating the adjustable portion transitioning to a predefined arcuate shape.

DETAILED DESCRIPTION

Figure 1:
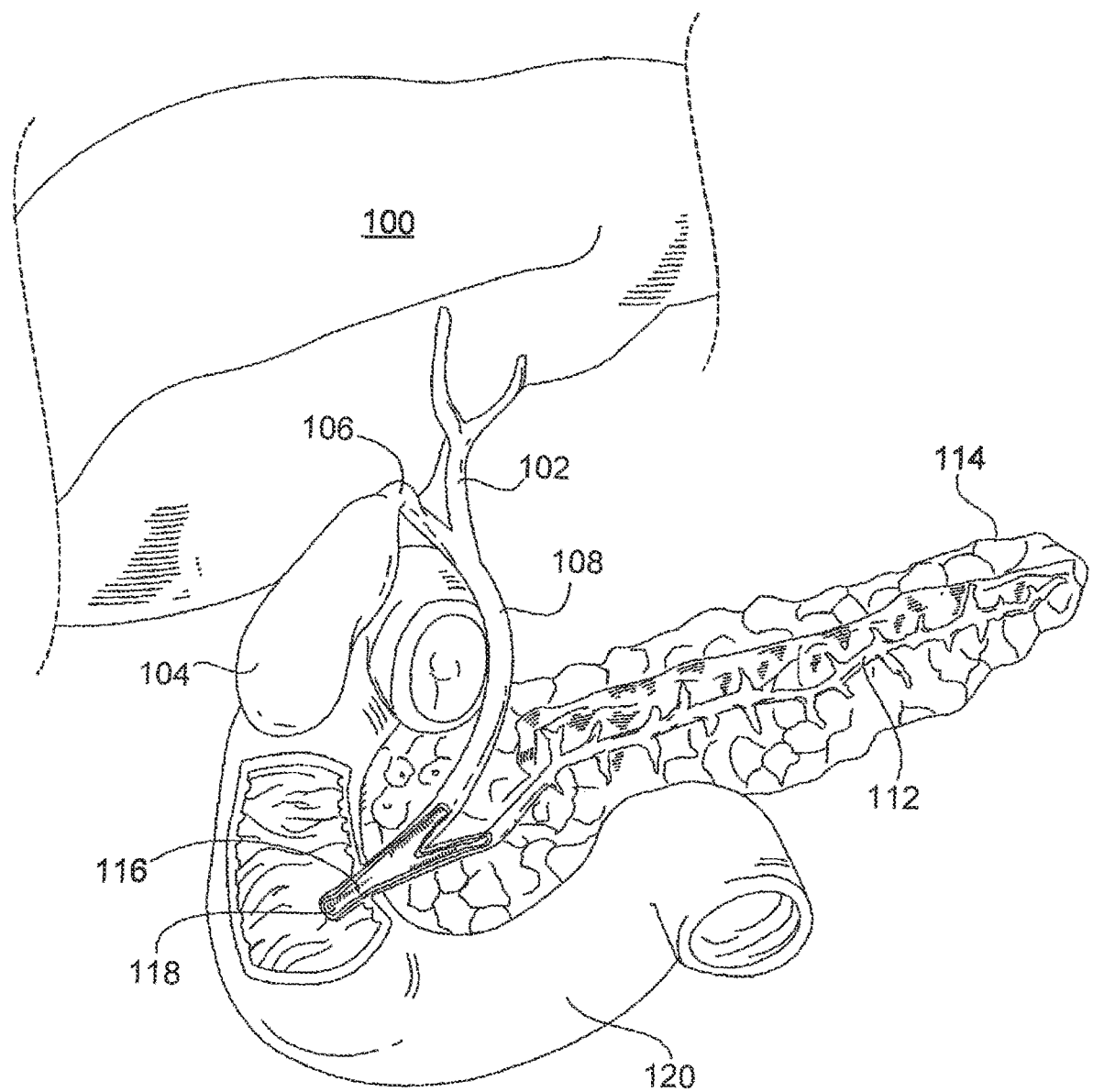
FIG. 1 illustrates an overview of an exemplary biliary system.
Figure 2:
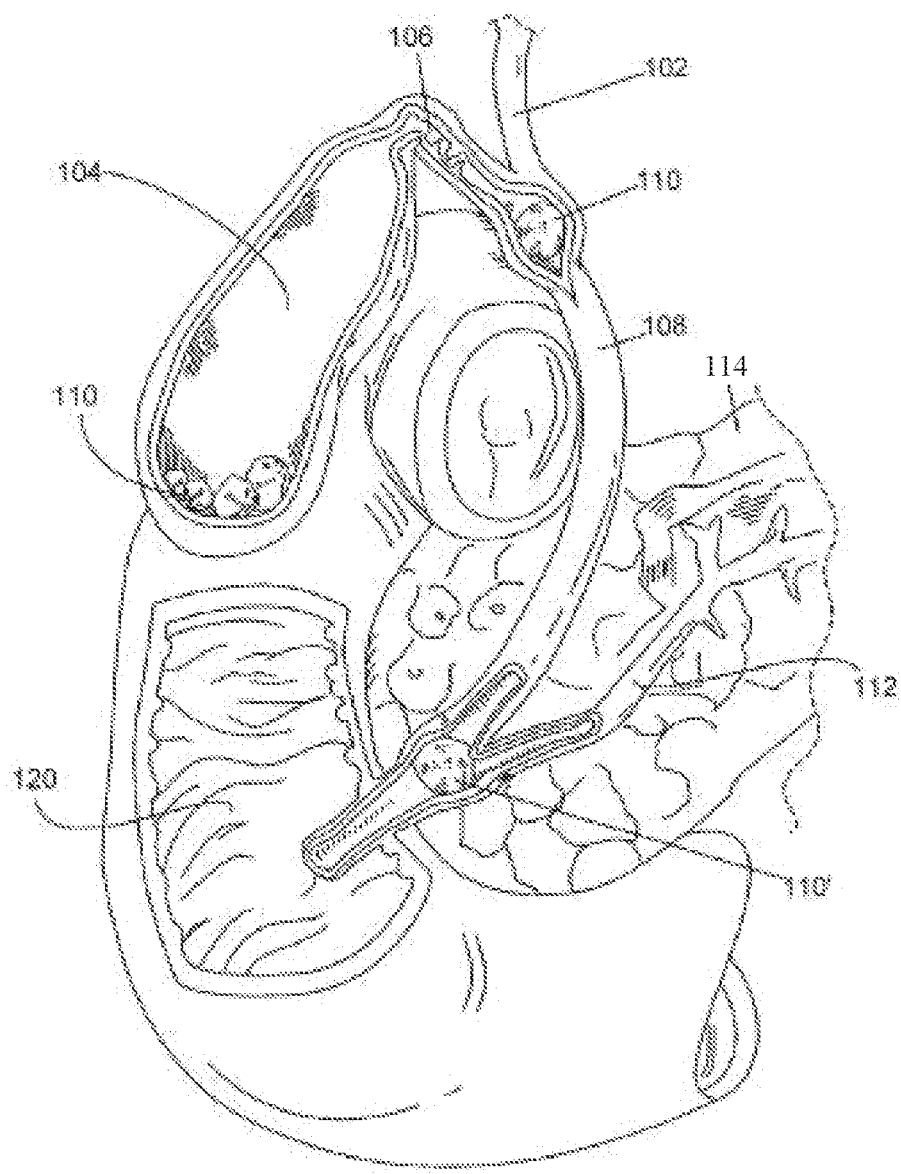
FIG. 2 illustrates the biliary system of FIG. 1 with one or more obstructions in a biliary duct.
Figure 3:
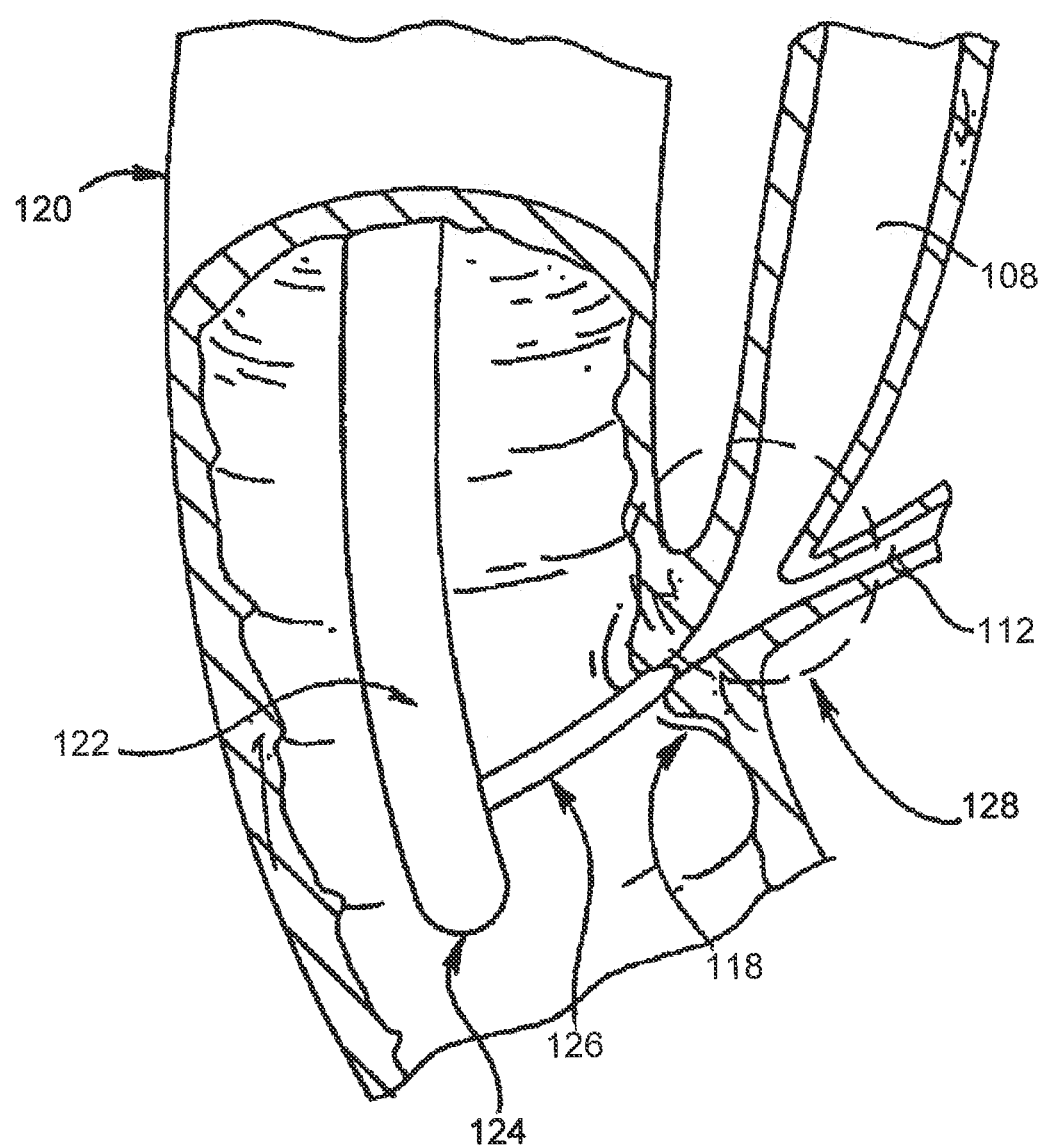
FIG. 3 illustrates the advancement of an endoscope through the duodenum to a position adjacent the ampulla of Vater.
Figure 4:
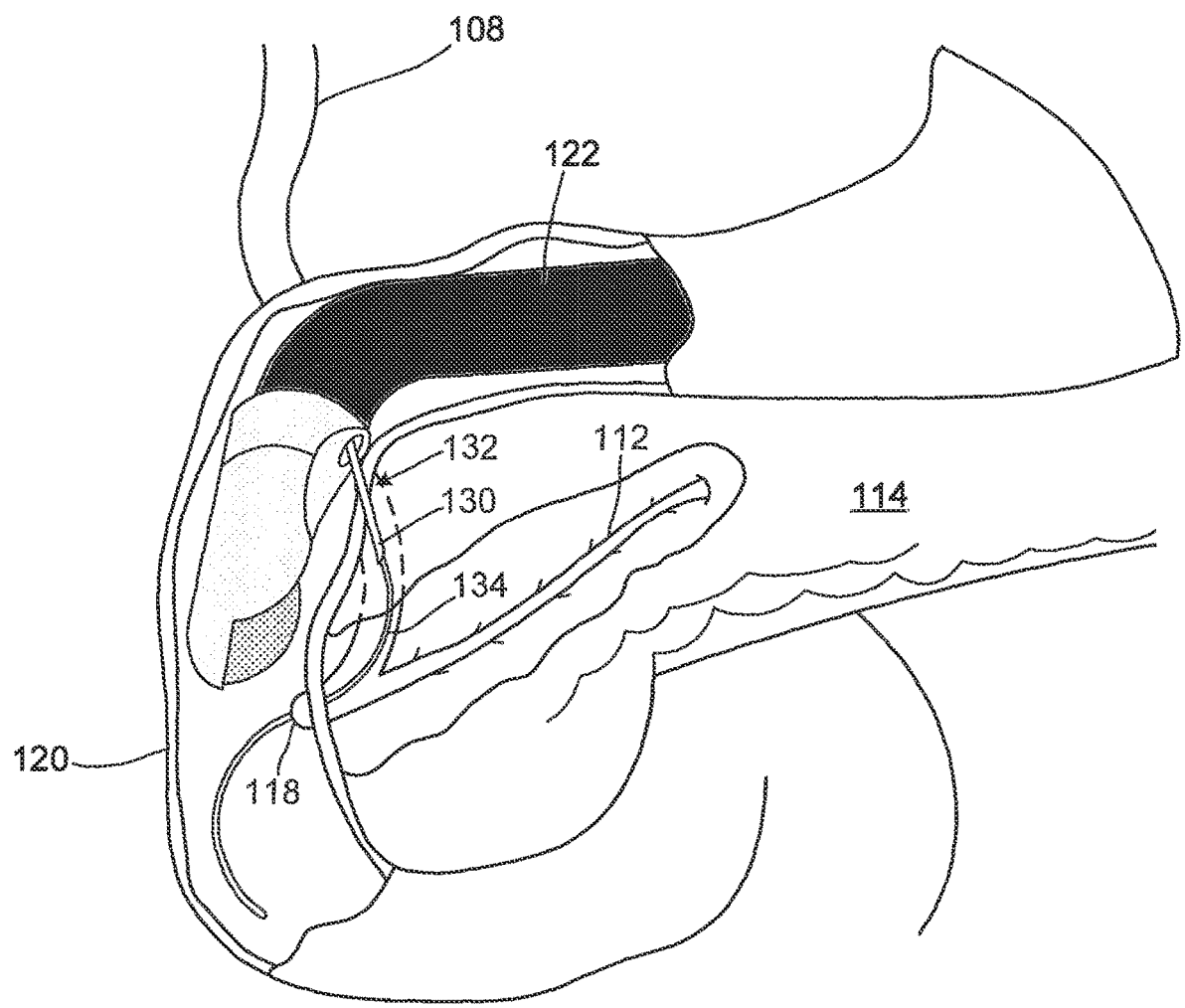
FIG. 4 illustrates an endoscopic ultrasound guided rendezvous technique for achieving biliary drainage.

By way of overview, the present disclosure is generally directed to an access system having a maneuverable catheter assembly configured for providing access to and navigating a desired vessel for subsequent treatment thereof. In embodiments described herein, the access system is guided via endoscopic ultrasound (EUS) and configured for to provide access to one or more tissues/organs associated with the pancreaticobiliary system for the purpose of providing treatment. In particular, the access system described herein is configured to provide access to at least the common biliary duct via an Endoscopic Ultrasound-Guided Fine-Needle Aspiration (EUS-FNA) technique and to further allow procedures to treat narrowed areas or blockages within the bile duct, including palliative drainage procedures. Accordingly, the access system is configured to provide Endoscopic Ultrasound Guided Biliary Drainage (EUS-BD). However, it should be noted that the access system of the present invention is not limited to the pancreaticobiliary system. The access system of the present invention can be used to provide access to a variety of different systems of the human body, particularly where maneuverability and accuracy is desirable.

Embodiments of the present disclosure are now described in detail with reference to the drawings in which like reference numerals designate identical or corresponding elements in each of the several views. As used herein, the term "clinician" refers to a doctor, nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The access catheter assembly of the present disclosure may be used in conjunction with minimally-invasive procedures, such as endoscopic biopsy procedures. For example, the access catheter may be compatible with an endoscopic biopsy device, such as needle biopsy delivery device configured for endoscopic ultrasound procedures. For example, the access catheter may be compatible for use with exemplary endoscopic delivery systems and methods discussed in Needle Biopsy Device with Exchangeable Needle and Integrated Needle Protection, U.S. Pub. 2012/0116248, Rapid Exchange FNA Biopsy Device with Diagnostic and Therapeutic Capabilities, U.S. Pub. 2011/0190662, Device for Needle Biopsy with Integrated Needle Protection, U.S. Pub. 2010/0121218, and Needle Biopsy Device, U.S. Pub. 2010/0081965, the contents of each of which are hereby incorporated by reference in their entirety.

Figure 5:
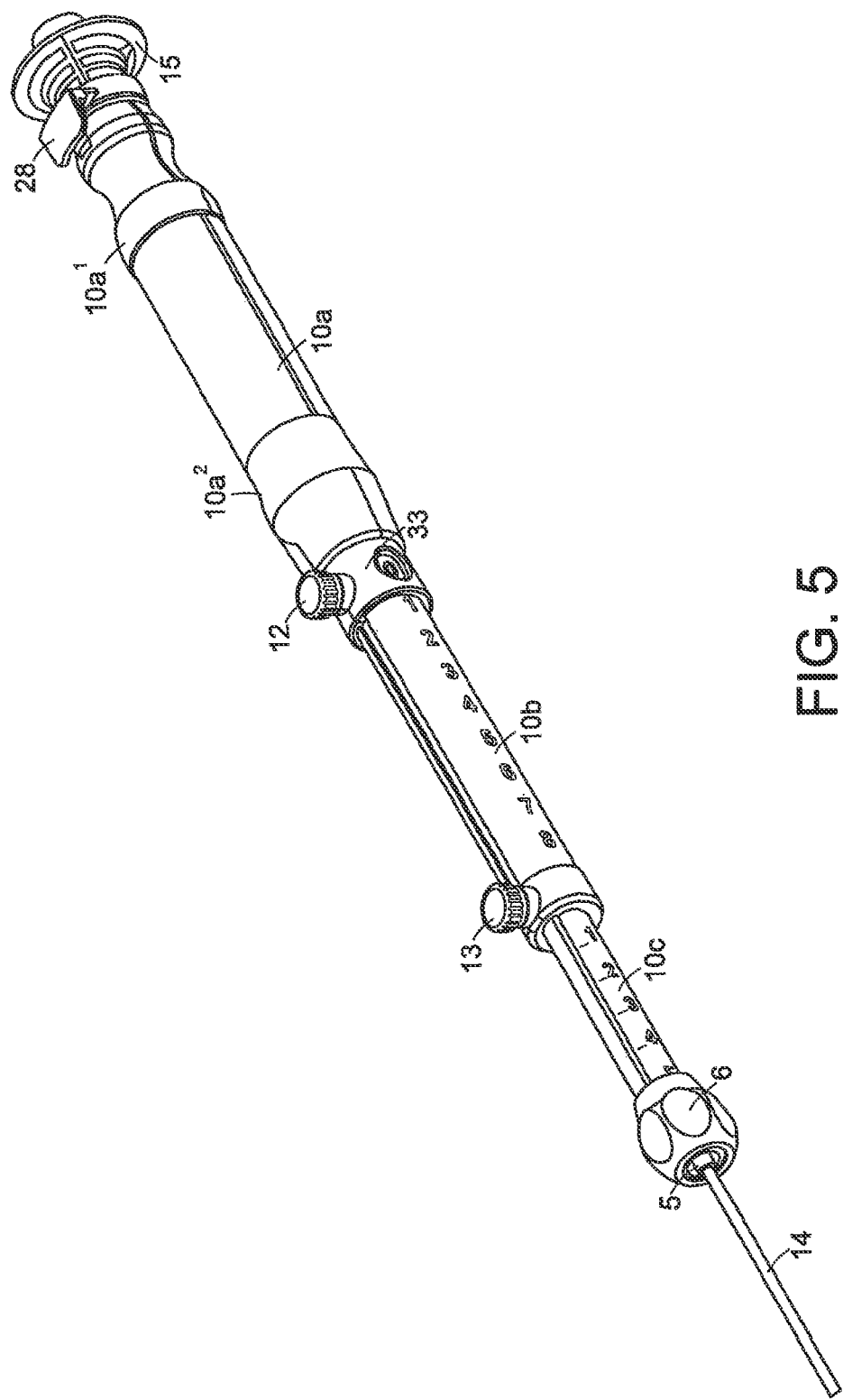
FIG. 5 is an assembly drawing depicting the present invention incorporating the delivery system handle, catheter sheath and aspiration needle for the intended field of use.

An exemplary embodiment of an endoscopic delivery device for use with an access catheter of the present disclosure is illustrated in FIG. 5. The device design consists of a handle mechanism (delivery system handle 10) and aspiration needle sub-assembly 15. The delivery system handle 10 includes a proximal handle member 10a, a middle handle member 10b, and a distal handle member 10c. The proximal, middle and distal handle members each include an inner lumen and are coupled together to define a longitudinal axis such that the inner lumens are in constant communication and extends throughout the length of the coupled handle members. Proximal handle member 10a is slideably disposed over at least a portion of the middle handle member 10b, and middle handle member 10b is slideably disposed over at least a portion of distal handle member 10c. The proximal handle member 10a includes proximal handle grip 10a1 a distal handle grip 10a2. The delivery handle system 10 further includes an inner handle member 10d disposed within the inner lumen of the middle handle member 10b (shown in FIGS. 9 and 11). The delivery system handle 10 also incorporates a catheter sheath 14 component coupled to the distal end of the distal handle member 10c. This component provides a conduit between the delivery system handle 10 and the target sampling site during the exchange of aspiration needles. The device design is modular in that the aspiration needle sub-assembly 15 can be detached from the proximal handle member 10a of the device for each individual "pass" or aspirated sample taken by the endoscopist at the site of the lesion or abnormality.

The delivery system handle 10 incorporates two length adjustment features actuated via adjustment of two thumb-screw locking mechanisms. A threaded proximal thumbscrew 12 and locking ring 33 are moveably disposed around the middle handle member 10b; the proximal thumbscrew 12 is loosened to loosen locking ring 33, locking ring 33 is moved distally along the middle handle member 10b and tightened in the desired position along middle handle member 10b via proximal thumbscrew 12 to allow the user to establish a set depth of needle penetration beyond the end of the catheter sheath 14. A threaded distal thumbscrew 13 is transversely disposed at the distal portion of the middle handle member 10b; the distal thumbscrew 13 is loosened to move the middle handle member 10b distally and/or proximally and tightened to allow the user to establish a set depth of catheter sheath 14 extension beyond the end of the endoscope.

The aspiration needle sub-assembly 15 consists of the needle shaft 21 (which can range in length from 500 mm up to 2500 mm, but which more preferably ranges in length between 1640 mm to 1680 mm) and is beveled at the distal needle end to enhance tissue penetration during sample acquisition; needle hub 17; needle luer 18; needle collet 19; needle protection sub-assembly 9; stylette hub 20 and stylette shaft 22. The needle component itself can be manufactured from a number of metallic based (Stainless steel or alloys thereof; Nitinol or Alloys thereof etc. . . . ) or Polymeric Based materials including, but not limited to Poly-ether-ether ketone, Polyamide, Poyethersulfone, Polyurethane, Ether block amide copolymers, Polyacetal, Polytetrafluoroethylene and/or derivatives thereof).

FIG. 6 illustrates the aspiration needle sub-assembly 15 of the present invention. This sub-assembly is inserted into and removed from the lumen of the delivery system handle 10 in acquiring tissue samples. The aspiration needle sub-assembly 15 consists of a stylette hub 20 and stylette shaft 22 components which are securely locked on the needle luer 18 of the aspiration needle via conventional internal luer threads. The stylette hub 20 may be attached to the stylette shaft 22 via a number of processing techniques such as adhesive bonding or insert injection molding. The female luer of the aspiration needle incorporates a mating luer thread detail, onto which the stylette hub 20 may be tightened. The needle luer 18 element of the present invention may be attached to the proximal end of the needle shaft via a number of processing techniques such as adhesive bonding or insert injection molding.

Figure 14A:
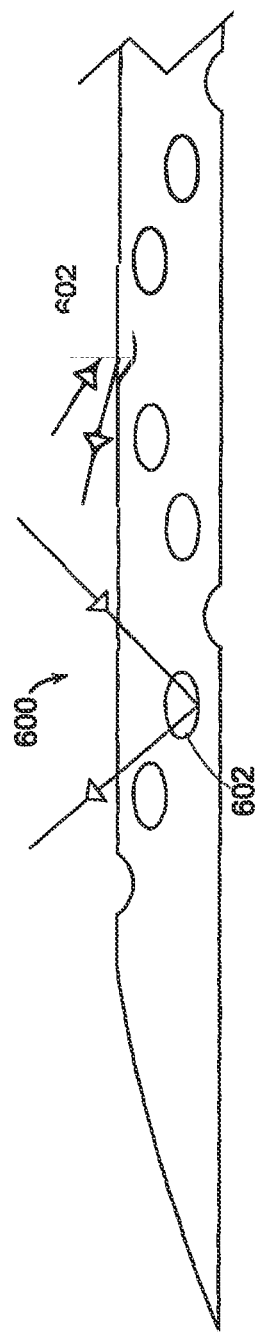
FIGS. 14A through 14O depict exemplary embodiments of an echogenically enhanced region at the distal end of an aspiration needle for use in the devices of the invention.
Figure 14B:
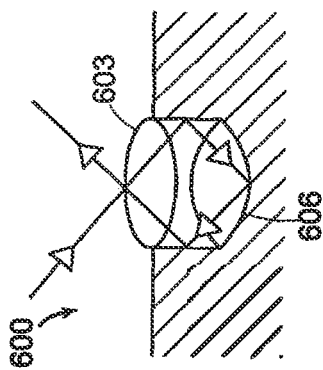
FIG. 14 is a drawing of the distal end of the needle with mounted needle collet.
Figure 14C:
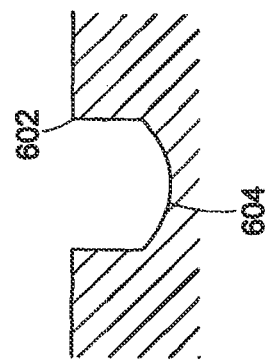
Figure 14D:
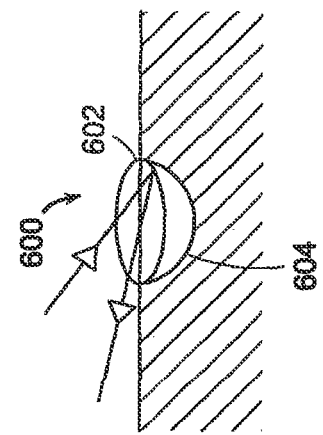
Figure 14E:
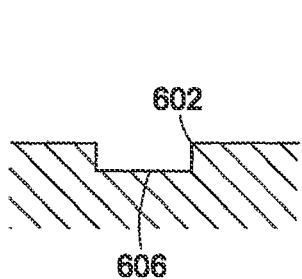
Figure 14F:
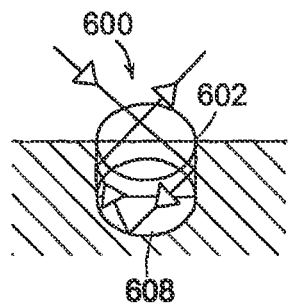
Figure 14G:
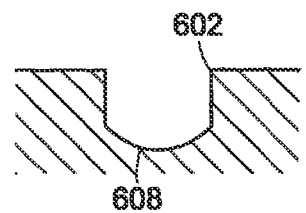
Figure 14H:
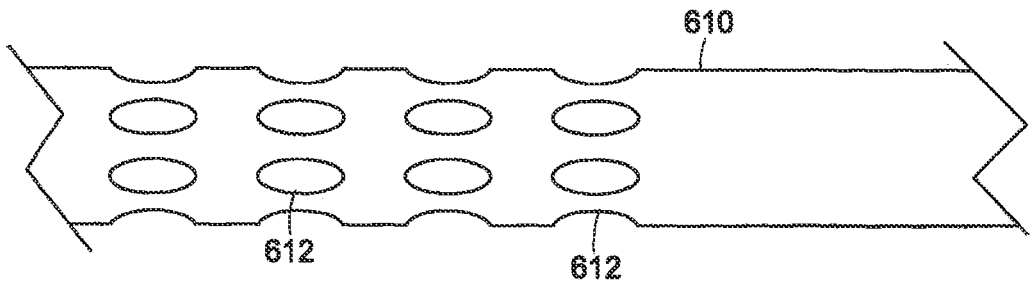
Figure 14I:
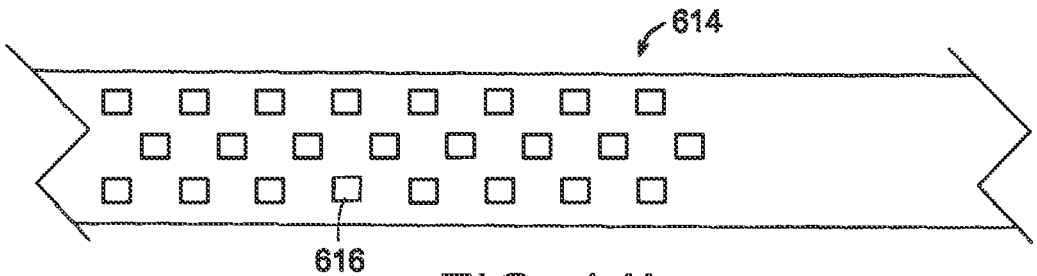
Figure 14J:
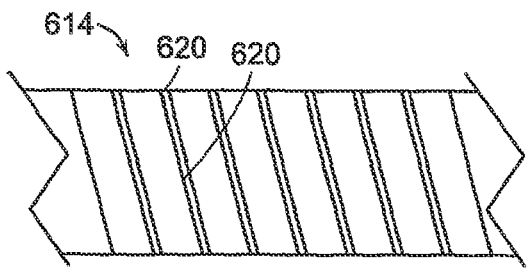
Figure 14K:
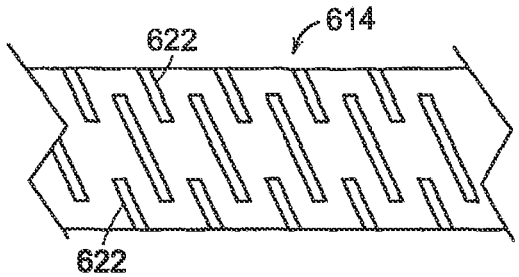
Figure 14L:
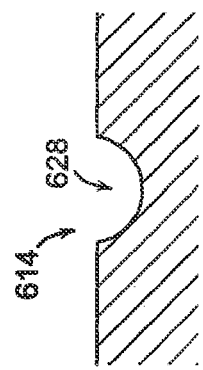
Figure 14M:
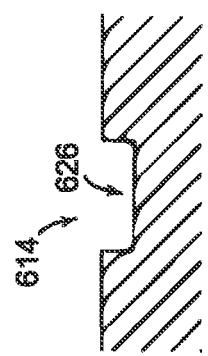
Figure 14N:
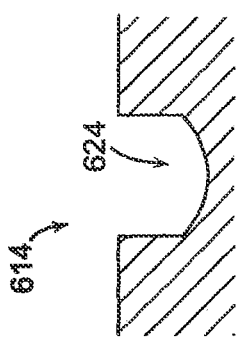
Figure 14O:
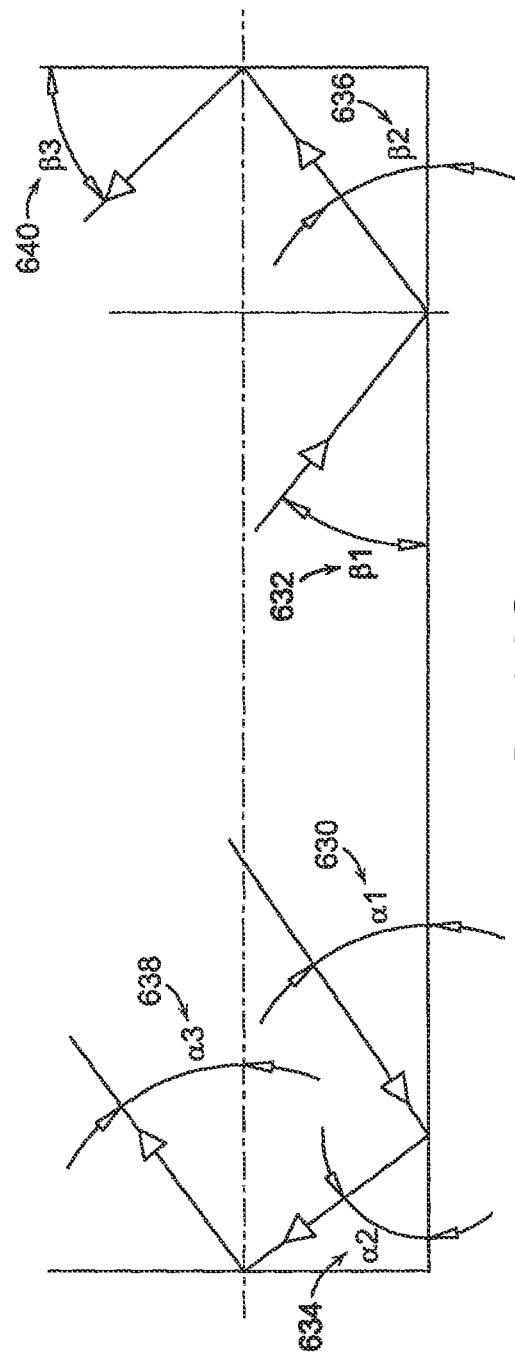
Figure 14:
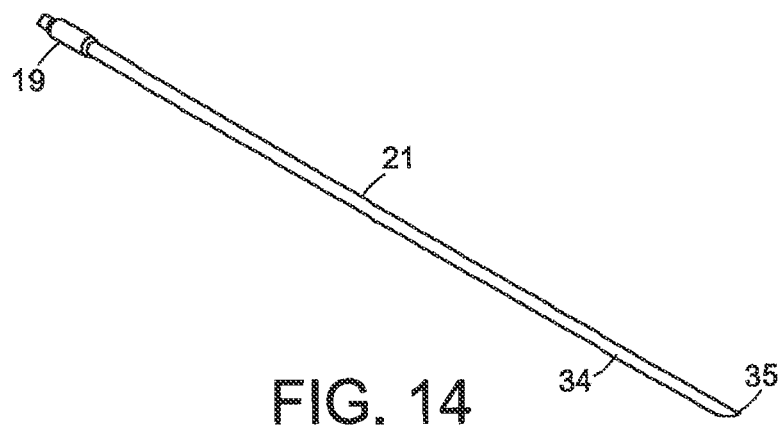

The aspiration needle sub-assembly 15 also incorporates a needle collet 19 (previously described as "needle protrusion(s) and shown in FIGS. 7 and 14 of Applicant's co-pending application (U.S. Ser. No. 12/243,367, published as US2010/0081965). The function of this needle collet 19 is to (1) provide a means to center the needle shaft component in the catheter sheath of the delivery system during needle exchange (2) provide a mechanism or securing and locking the needle protector sub-assembly to the distal end of the aspiration needle once the needle has been unlocked and withdrawn from the delivery system handle. The needle collet 19 of the present invention may be attached to the distal end of the needle shaft 21 via a number of processing techniques such as adhesive bonding, laser welding, resistance welding, or insert injection molding. The needle collet 19 may be fabricated from metals materials such as stainless steel, nickel titanium or alloys thereof or polymer materials such as, but not limited to, Polyacetal, polyamide, polyether-block-amide, polystyrene, Acrylonitrile butadiene styrene or derivatives thereof. The needle collet 19 is located at a set point distance from the extreme distal end of the beveled needle. The distance from the extreme distal end of the needle bevel to the proximal collet position on the needle may be within the range of 6 cm to 12 cm but is more preferably in the range of 7 cm to 9 cm and more preferably is located 8 cm from the end of the needle. This ensures that when the needle is extended to a maximum extension distance relative to the distal end of the catheter sheath (i.e. 8 cm), the needle collet 19 does not exit the end of catheter sheath 14.

Figure 18:
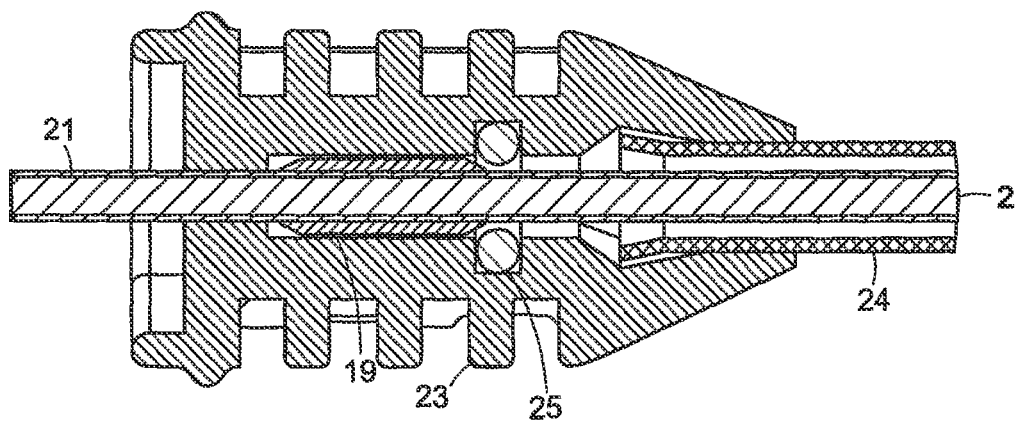
FIG. 18 is a cross sectional drawing of the proximal end of the needle protector hub sub-assembly.

FIGS. 7 and 18 illustrate the needle protection sub-assembly 9 design embodiment of the current invention, in the locked position at the distal end of the needle. The needle protection sub-assembly 9 consists of two needle protector (NP) hub halves (collectively 23), which are adhesively bonded to each other, on the proximal end of the needle protector (NP) needle protector sheath 24. Alternately, these needle protector hub halves 23 may be snap fit together or may be insert injection molded over the needle protector sheath 24 to provide a secure bond/attachment between these components in the assembly. The needle protection sub-assembly 9 also incorporates a needle protector (NP) hub O-ring 25. This component resides in a recessed cut-out in the center of the assembled needle protector hub halves 23. This NP hub O-ring 25, in conjunction with the needle collet 19 which is securely attached to the distal end of the needle shaft 21 of the needle protection sub-assembly 9, provides a mechanism for locking the needle protection sub-assembly 9 onto the end of the needle. In this way, the bevel of the needle is protected, covered and shielded once the needle has been removed from the delivery system handle. It is desired that the needle protector sheath 24 of the present invention be manufactured from a translucent polymer such as, but not limited to polyurethane, polyamide and derivatives thereof.

The needle hub 17 embodiment of the aspiration needle sub-assembly as shown in FIG. 6 and FIG. 8 of the present invention, provides a mechanism which (1) locks the aspiration needle sub-assembly 15 into the delivery system handle 10 by means of the inner hub housing 27 and thumb latch 28 components (as will be described later in this disclosure) and (2) provides a means to lock the needle protection sub-assembly 9 embodiment shown in FIG. 7, into the delivery system device handle 10, as will be described later. As shown in FIG. 8, the needle hub 17 is securely attached to the needle luer 18 and needle shaft 21 components of the aspiration needle sub-assembly 15. The needle hub 17 of the present invention may be attached to the distal end of the needle luer 18 via a number of processing techniques such as adhesive bonding or insert injection molding.

An alternate preferred embodiment of the proximal end of the aspiration needle sub-assembly 15 is shown in FIGS. 8A and 8B. This embodiment incorporates a strain relief component 26, which extends from the distal end of the needle luer 18, through the body of the needle hub 17, to extend beyond the distal end of the needle hub 17. This tubular strain relief component 26 is intended to provide a more gradual stiffness transition between the needle hub 17 and needle shaft 21 components, particularly in the case of smaller needle gauge sizes (such as 22 AWG and 25 AWG). This strain relief component 26 may range in length from 10 mm to 50 mm but is more preferably in the range of 25 mm to 35 mm. The diameter of this strain relief component 26 must be sufficiently small so that it fits through the proximal end of the needle protection sub-assembly 9 (as shown in FIG. 7) and does not impair the ability for the needle protection sub-assembly 9 to slide back and forth on same. This strain relief component 26 may range in outer diameter from 0.020 inches to 0.060 inches but is more preferably in the range of 0.026 inches to 0.045 inches. This tubular strain relief component 26 may be fabricated from metal based materials, such as but not limited to stainless steel, nickel titanium or alloys thereof or polymer materials such as, but not limited to, Polyacetal, polyamide, poly-ether-block-amide, polystyrene, Acrylonitrile butadiene styrene or derivatives thereof.

Figure 9:
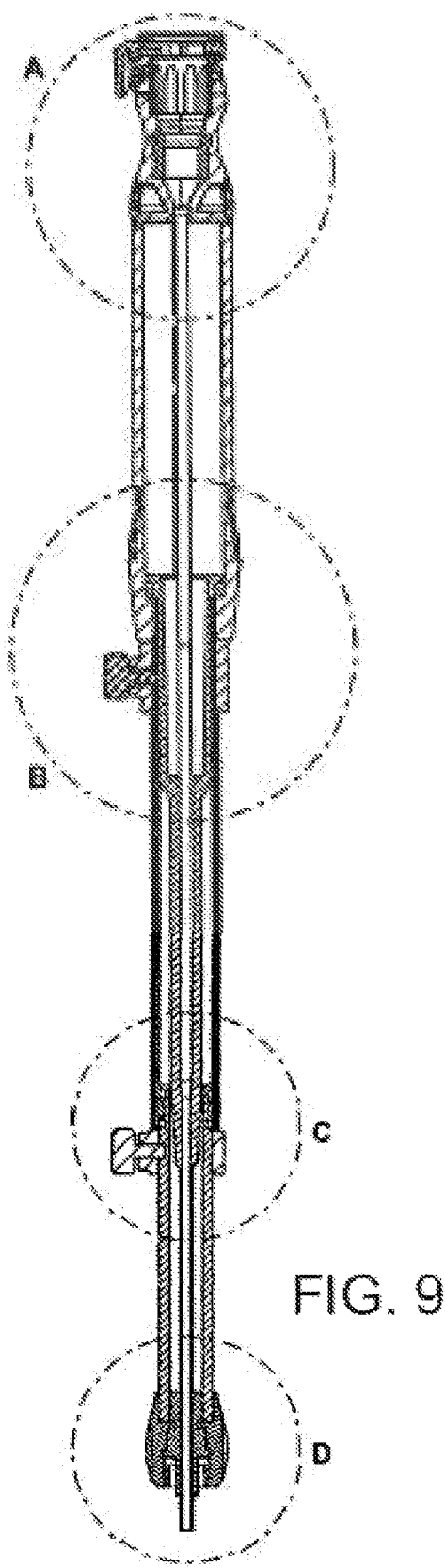
FIG. 9 is a cross sectional drawing of the delivery system handle of the present invention.
Figure 10:
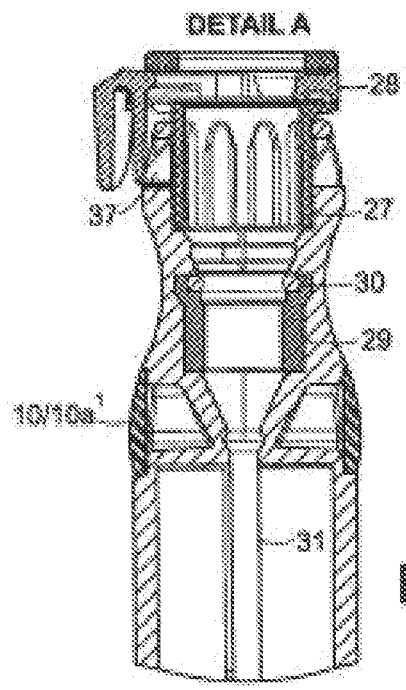
FIG. 10 is an enlarged view of encircled Portion A shown in FIG. 9, and depicts a cross sectional drawing of the needle locking mechanism of the delivery system handle of the present invention.

FIG. 9 is a sectional view of the delivery system handle 10 for the present invention, without the aspiration needle sub-assembly 15 loaded therein. FIG. 10 (Detail A from FIG. 9) illustrates a sectional view of the proximal end 10a of the assembled device handle. This proximal portion of the handle (also shown in FIG. 20 and FIG. 22) contains elements to ensure secure, yet releasable locking of the aspiration needle sub-assembly 15 in the delivery system handle 10. The inner hub housing 27 is secured to the proximal delivery system handle halves 10a via adhesive bonding or ultrasonic welding techniques. The thumb latch 28 is securely locked into the inner hub housing 27 via a one-way keying action. Once the thumb latch 28 is inserted into the inner hub housing 27, the thumb latch 28 cannot be disassembled and may only be moved in the transverse direction to actuate the assembled mechanism.

Figure 9A:
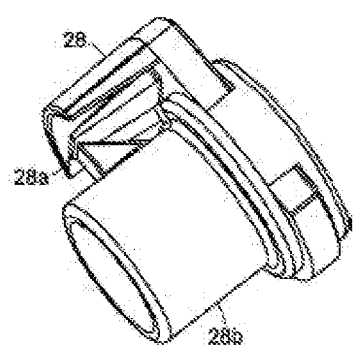
FIGS. 9A through 9D depict various enlarged views of a thumb latch included in the proximal portion of the delivery system handle of the invention.
Figure 9C:
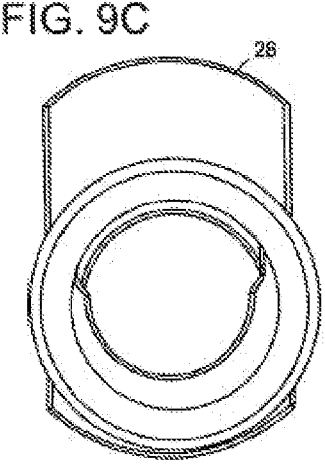
Figure 9B:
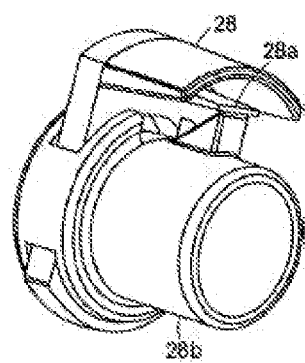
Figure 9D:
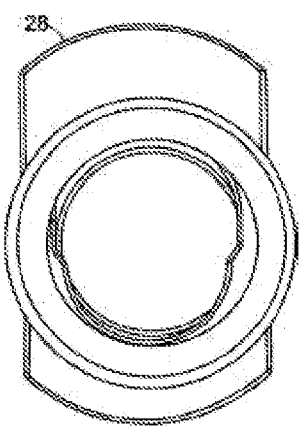

FIGS. 9A, 9B, 9C, and 9D depict various views of an exemplary embodiment of the thumb latch 28 of the delivery system handle 10. The thumb latch 28 represents a mechanism to releasably lock the needle hub 17 of aspiration needle sub-assembly 15 within the inner hub housing 27 of the proximal handle member 10a of the delivery device. Thumb latch 28 may be, for example, a push-button, that activates the use of a deflectable hinge member 28a to provide for a return to the "home" position once external force is not applied to release thumb latch 28. Deflectable hinge member 28a can elastically deform to provide for the opening and closing of the "lock" during removal of the aspiration needle sub-assembly 15 from the delivery system handle 10. In one embodiment, thumb latch 28 incorporates an external coupler housing 28b and a push button design mechanism. FIGS. 9C and 9D illustrate thumb latch 28 in the CLOSED and OPEN positions during a typical actuation cycle.

Referring to FIGS. 9A and 9B, thumb latch 28 and external coupler housing 28b may be manufactured from a range of rigid, non-deformable, thermoplastic or thermoset materials such as, acrylonitrile butadiene styrene (ABS), styrene acrylonitrile (SAN), polystyrene or rigid derivatives thereof, polyamide, polyethylene, polyurethane, and polycarbonate. In an embodiment, the materials of manufacture have a durometer in the range of 35-120 Shore D, but more preferably in the range of 80-110 Shore D.

Deflectable hinge member 28a may be manufactured from a range of rigid, thermoplastic or thermoset materials such as, acrylonitrile butadiene styrene (ABS), styrene acrylonitrile (SAN), polystyrene or rigid derivatives thereof, polyamide, polyethylene, polyurethane, and polycarbonate. In an embodiment, the materials of manufacture shall be capable of deformation in bending under the application of an applied load, such as is encountered during a typical "Open and Close" cycle for the needle biopsy device without crazing, fatigue or cracking.

The proximal portion of the proximal handle member 10a of the delivery system handle 10, incorporates a retention collar 29 and a retention collar O-ring component 30. The retention collar 29 resides in a cut out nest in the proximal handle half, and is in communication with inner hub housing 27. The retention collar 29 is a cylindrical component, which is internally tapered and recessed to provide an internal, recessed shelf. The retention collar O-ring component 30 resides in this recessed shelf and is secured in position through the assembly of both halves of the delivery system handle halves. The purpose of this retention collar O-ring component 30 is to provide a method to lock and maintain the needle protector hub sub-assembly 9 of the aspiration needle sub-assembly 15, securely in the handle 10 of the delivery system while the tissue sample site is being accessed by the clinician, as described in detail below. The functionality and operation of this retention collar O-ring component 30 is the same as described in FIGS. 41 and 42 and associated abstract of the specification of Applicant's patent application U.S. Ser. No. 12/607,636 (published as US2010/0121218).

As shown in FIG. 10, the delivery system handle assembly 10 of the present invention incorporates an inner hypotube component 31. It is the design intent of this component to provide a conduit between the proximal handle member 10a of the delivery system, and the outer hypotube component 32 shown in FIG. 11. The inner hypotube component 31 may be fabricated from metal based materials, such as but not limited to stainless steel, nickel titanium or alloys thereof or polymer materials such as, but not limited to, Polyacetal, polyamide, poly-ether-block-amide, polystyrene, Acrylonitrile butadiene styrene or derivatives thereof. The inner hypotube component 31 is secured to the assembled handle halves of the device via adhesive bonding or insert injection molding techniques. During needle advancement, the proximal handle member 10a of the delivery system is distally advanced, in order to advance the distal end of the needle into the desired tissue sampling site. When the proximal handle member 10a is distally advanced, the inner hypotube component 31 is also advanced in unison in a distal direction. The inner hypotube component 31 is in constant longitudinal communication with the outer hypotube component 32 and is designed to telescope inside the outer hypotube component 32 at all times. This ensures that needle passage during needle exchange into and out of the delivery system, is not impaired.

Figure 11:
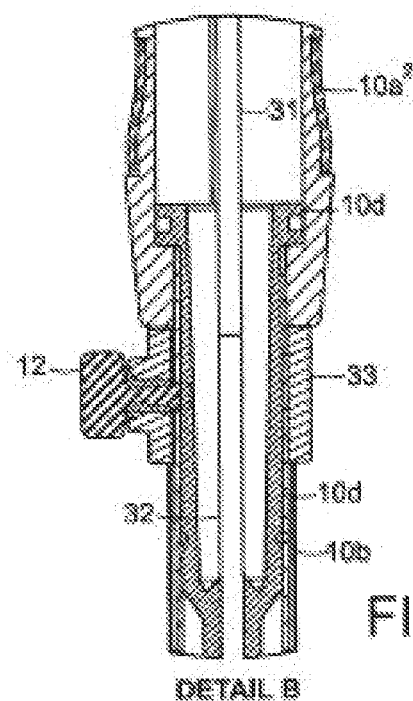
FIG. 11 is an enlarged view of encircled Portion B shown in FIG. 9, and depicts cross sectional drawing of the needle extension length adjustment mechanism of the delivery system handle of the present invention.

Referring now to FIG. 11 (Detail B from FIG. 9), a cross sectional view of the distal end of the proximal handle member 10a and the middle handle member 10b is illustrated. During a typical EUS FNA procedure, the locking ring 33 is loosened via proximal thumbscrew 12, moved distally and set to a pre-established depth by the clinician, dependent upon depth of needle penetration required. Once the locking ring 33 has been moved distally (via the proximal thumbscrew) and locked to the required depth of penetration, the proximal handle member 10a of the delivery system is advanced. During advancement, the proximal handle member 10a moves in a longitudinal direction over the middle handle member 10b and inner handle member 10d. The inner handle member 10d and middle handle member 10b components are securely bonded to each via adhesive bonding or ultrasonic welding techniques and remain in a stationary, locked position during needle advancement via proximal handle member 10a actuation in a distal direction.

As shown in FIG. 11, the outer hypotube component 32 is also in constant communication with the catheter sheath 14 of the delivery system. The proximal end of the catheter sheath 14 is flared in an outward direction. The distal end of the outer hypotube component 32 is inserted into flared end of the catheter sheath 14 and secured thereto via adhesive bonding or insert injection molding techniques. The inner handle member 10d is bonded to both the proximal end of the catheter sheath 14/outer hypotube component 32 assembly via adhesive bonding or insert injection molding techniques. In this way, the inner hypotube component 31, outer hypotube component 32 and catheter sheath 14 are in constant communication, ensuring for smooth needle passage during needle exchange. This design embodiment, also ensures that the catheter sheath 14 may be advanced through the distal handle member 10c as required.

Figure 12:
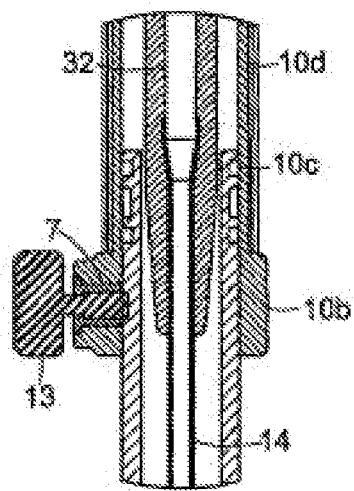
FIG. 12 is an enlarged view of encircled Portion C shown in FIG. 9, and depicts a cross sectional drawing of the catheter sheath extension length adjustment mechanism of the delivery system handle of the present invention.
Figure 13:
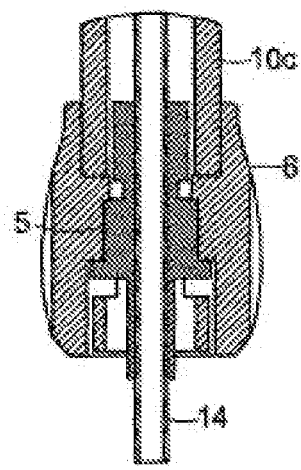
FIG. 13 is an enlarged view of encircled Portion D shown in FIG. 9, and depicts a cross sectional drawing of the distal end of the assembled delivery system handle of the present invention, incorporating the mechanism for attachment to the endoscope.

FIGS. 12 and 13 illustrate the design assembly embodiments for catheter sheath extension length adjustment in the case of the present invention. Referring to FIG. 12, the distal end of the middle handle member 10b incorporates a threaded insert 7 and distal thumbscrew 13. The catheter sheath extension distance beyond the end of the endoscope may be adjusted by loosening the distal thumbscrew 13 and advancing the middle handle member 10b in a distal direction over the distal handle member 10c. The distal handle member 10c and middle handle member 10b are in constant longitudinal communication with each other.

Referring to FIG. 13, the distal end of the delivery system handle assembly 10 is illustrated. The distal handle member 10c is secured to a recess in the distal luer holder 6 via adhesive bonding or ultrasonic welding techniques. The distal luer holder 6 is securely attached to the scope luer lock 5 via adhesive bonding or insert injection molding techniques. The distal handle member 10c is designed in such a way that once the device handle is attached to the working channel port of the endoscope, the assembly cannot rotate independently of assembled scope luer lock 5 and distal luer holder 6 components. Once the entire delivery system handle 10 (as shown in FIG. 5 and cross sectional view FIG. 9) has been locked onto the endoscope via the scope luer lock 5, the catheter sheath length and needle penetration extension length may be established as previously described.

FIG. 14 is an illustration of the distal end of the aspiration needle of the present invention, with needle collet (referred to as "needle protrusions" in Applicant's patent application U.S. Ser. No. 12/607,636, published as US2010/0121218) secured on the needle. It is preferable that the length of this needle collet 19 be in the range of 2 mm to 10 mm, but more preferably in the range of 3.5 mm to 5 mm. It is preferable that the outer diameter of the needle collet 19 be in the range of 0.030 inches to 0.080 inches, but more preferably in the range of 0.040 inches to 0.070 inches. This needle collet 19 (see also FIG. 18 and FIG. 30) is also chamfered at the proximal and distal ends of same. It is preferable that the chamfer angle of the needle collet be in the range of 15 degrees to 80 degrees, but more preferably in the range of 30 degrees to 60 degrees. This chamfer on both ends of the needle collet 19 is intended to provide smooth locking and unlocking with the needle protector sub-assembly 9 during needle exchanges.

As depicted in FIG. 14, and FIGS. 14A through 14O, the distal end of the needle of the present invention incorporates an embodiment to enhance the echogenic signature of the needle. In the case of the present invention, this echogenically enhanced region 34 can be fabricated by, but not limited to roughening the end of the needle over a predefined length close to proximal end of the needle bevel 35. It is preferable that the length of this echogenically enhanced region 34 be in the range of 2 mm to 20 mm, but is more preferably in the range of 10 mm to 15 mm. In the case of the present invention, the echogenic enhanced pattern is imparted to the needle via a micro-blasting process which roughens the surface of the needle over a specific length, improving the visibility of the needle under endoscopic ultrasound.

In certain aspects of the invention, the echogenically enhanced region of the needle is achieved through the removal of material from the surface of the needle to provide greater reflectivity and strengthened reflected signal. It is contemplated that the removal of material does not, however, reduce the performance of the needle from a pushability perspective or deter its ability to acquire a desired sample.

Referring now to FIG. 14A, a perspective view of an embodiment of a needle 600 is presented. Needle 600 is comprised of a plurality of depressions 602. Depressions 602 may be, but are not limited to, circular, concave, cylindrical, helical, oval, rectangular, and square elements that take the form of indentations on the surface of needle 600. Depressions 602 may be arranged in a helical (spiral) fashion around the circumference of the distal needle end. These indentations may extend to the extreme end of the bevel or may end at a specific distance from the bevel of needle 600. The length of the distal end of needle 600 containing these depressions may be, for example, from one to twenty centimeters. In another embodiment, the length is between five to ten centimeters. Referring to FIGS. 14B and 14C, depression 602 have a concave detail 604. Referring to FIGS. 14D and 14E, depressions 602 have a square base edge 606. Referring to FIGS. 14F and 14G, depressions 602 have a hemispherical base detail 608.

Referring now to FIG. 14H, a perspective view of another embodiment of a needle 610 is presented. Needle 610 is comprised of elliptical depressions 612 around the circumference of the distal end of needle 610. Referring to FIG. 14I, a perspective view of an embodiment of a needle 614 having square depressions 616 is presented. Depressions 616 may extend to the extreme end of the bevel or may end at a specific distance from the bevel of needle 614. Referring to FIGS. 14J and 14K, embodiments of needle 614 including spiral depressions 620 and helical depressions 622 are presented. Referring to FIG. 14L, a depression 624 has a concave detail. Referring to FIG. 14M, a depression 626 has a square base edge. Referring to FIG. 14N, a depression 628 has a hemispherical base detail.

Referring now to FIG. 14O, a diagram of ultrasound waves impinging upon a needle depression at angles of $\alpha 1$ 630 and $\beta 1$ 632 respectively are presented. In an embodiment, a wave strikes the base of the depression and is reflected upwards at angle of reflection of $\alpha 2$ 634 and $\beta 2$ 636 respectively, which are equal to the angles of incidence of $\alpha 1$ 630 and $\beta 1$ 632 respectively. This reflected beam is reflected a second time off the adjacent wall of the depression at an angle of reflection of $\alpha 3$ 638 and $\beta 3$ 640 respectively, which are equal to the angles of incidence, α1 630 and β1 632 respectively and the angles of first reflection α2 634 and β2 636 respectively. In this manner, the reflected wave becomes reflected along the same angle of incidence as the initially propagated incident beam back to the transducer of the ultrasound device. In an embodiment, a square edge depression design may provide for more efficient remittance of ultrasound waves during the procedure.

Figure 15:
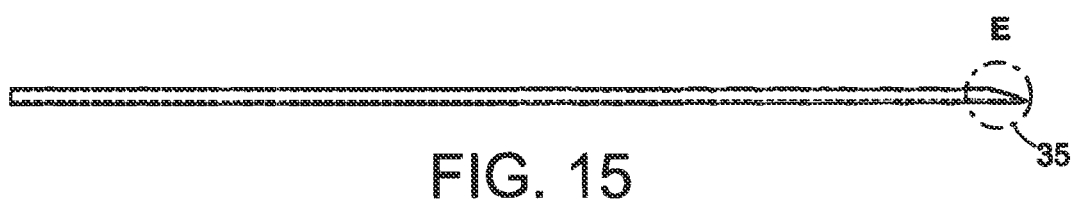
FIG. 15 is a drawing of the extreme distal end of the needle.
Figure 16:
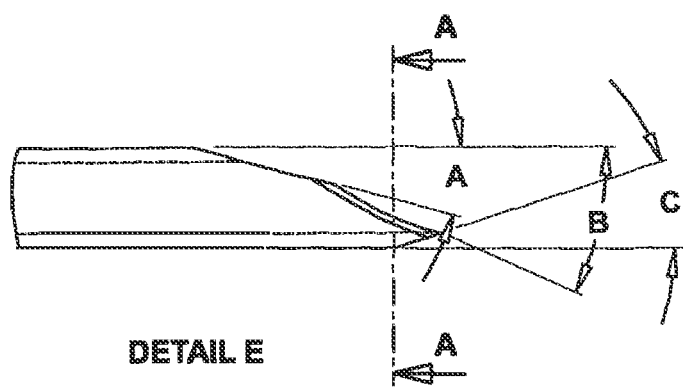
FIG. 16 is a drawing of the bevel detail of the needle of the present invention, incorporating primary angle, secondary angle, tertiary and back-cut angle elements.
Figure 17:
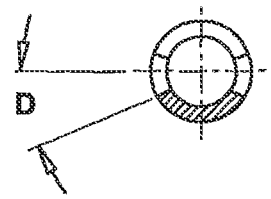
FIG. 17 is a cross sectional drawing of the bevel detail of the needle of the present invention, illustrating the tertiary angle of the grind detail.

FIGS. 15 and 16 are drawings of the distal end of the needle of the current invention. The distal end of the needle bevel 35 of the current invention is beveled to enhance the ability of the needle to penetrate tissue during sample acquisition. The needle bevel 35 of the present invention incorporates four angular bevel grinds, which, in addition to enhancing tissue penetration, also ensure the smooth passage of the needle down the catheter sheath of the delivery system during needle exchange. Referring to FIG. 16, the needle bevel grind of the current embodiment incorporates a primary angle ("A"), a secondary angle ("B"), a back-cut angle ("C") and tertiary angles ("D"), as shown in FIG. 17. It is preferable that the primary angle be in the range of 10 degrees to 25 degrees, but more preferably in the range of 12 degrees to 18 degrees. It is preferable that the secondary angle be in the range of 15 degrees to 35 degrees, but more preferably in the range of 22 degrees to 28 degrees. It is preferable that the tertiary angle be in the range of 15 degrees to 35 degrees, but more preferably in the range of 22 degrees to 28 degrees. It is preferable that the back-cut angle be in the range of 15 degrees to 70 degrees, but more preferably in the range of 25 degrees to 45 degrees.

During needle exchange, it is important that the aspiration needle (with pre-loaded stylette 2) can be passed through the internal diameter of the catheter sheath 14 without catching on the internal wall of same. In order to achieve this, the bevel grind of the current invention incorporates a back-cut grind detail. This back-cut detail acts as a "bumper" during needle passage through the sheath. As the needle advances, the heel of the back-cut comes in contact with the internal diameter of the sheath and reduces the friction between needle bevel 35 and catheter sheath 14 components. In this way, the needle can be smoothly tracked through the catheter sheath to exit the end of the catheter sheath 14.

Figure 19:
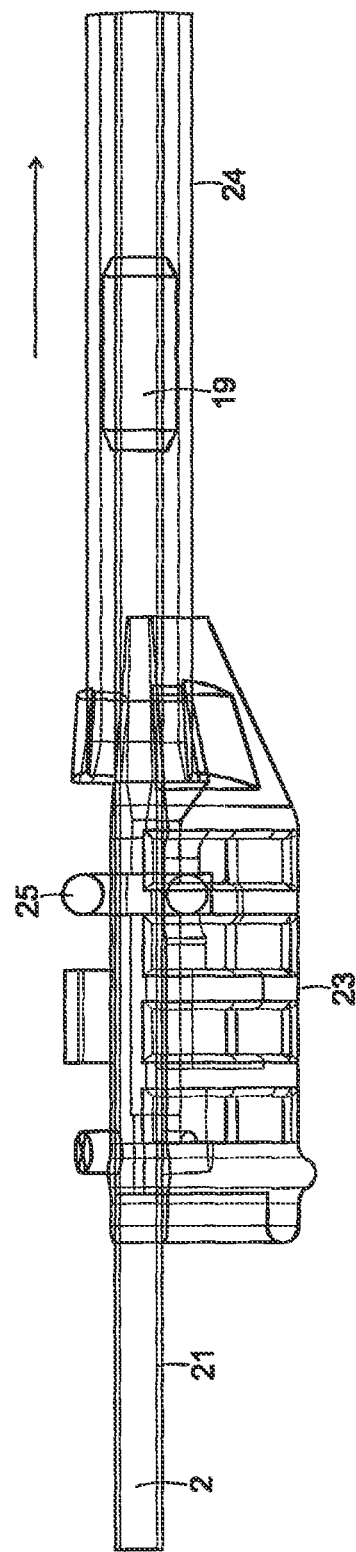
FIG. 19 is a drawing of the intended functionality of the needle protector assembly.
Figure 27:
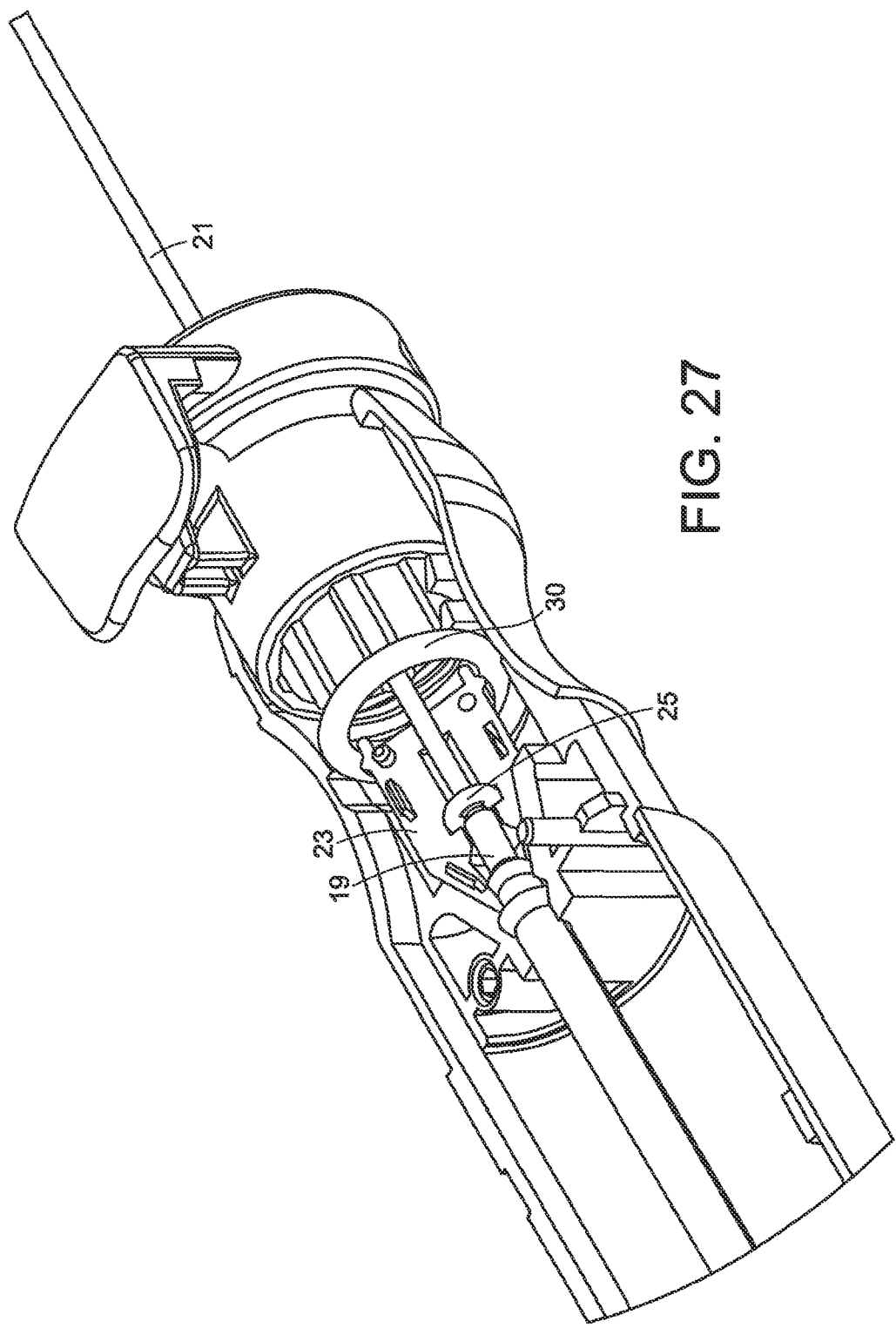
FIG. 27 is a drawing of the intended functionality of the needle collet during needle exchange and more specifically, during needle extraction from the device handle.

FIG. 18 and FIG. 19 illustrate the method of engagement and disengagement between the aspiration needle sub-assembly 15 with mounted needle collet 19 and the needle protector ("NP") sub-assembly 9. Referring to FIG. 18, the needle protector hub 23 is locked onto the needle collet 19 at the distal end of the needle shaft 21 by inserting the needle shaft 21 into the needle protector hub 23. As the needle/NP protector assembly is inserted into the handle of the delivery system, the needle shaft 21 and needle collet 19 are advanced such that the needle collet 19 traverses the deformable NP Hub O-ring 25. The internal diameter of the NP Hub O-ring 25 in the non-deformed state, is smaller than the outer diameter of the needle collet 19. Due to the soft durometer and elastic nature of the NP Hub O-ring 25, as the needle shaft 21 and attached needle collet 19 are moved distally, the NP hub O-ring 25 deforms allowing the collet to traverse the NP hub O-ring 25 under applied longitudinal force. Once the needle collet 19 has traversed the NP hub O-ring 25, the needle shaft 21 with pre-mounted needle collet 19 are tracked through the catheter sheath 14 to the intended target site. This aspect of the current invention is also illustrated in FIG. 27.

Figure 20:
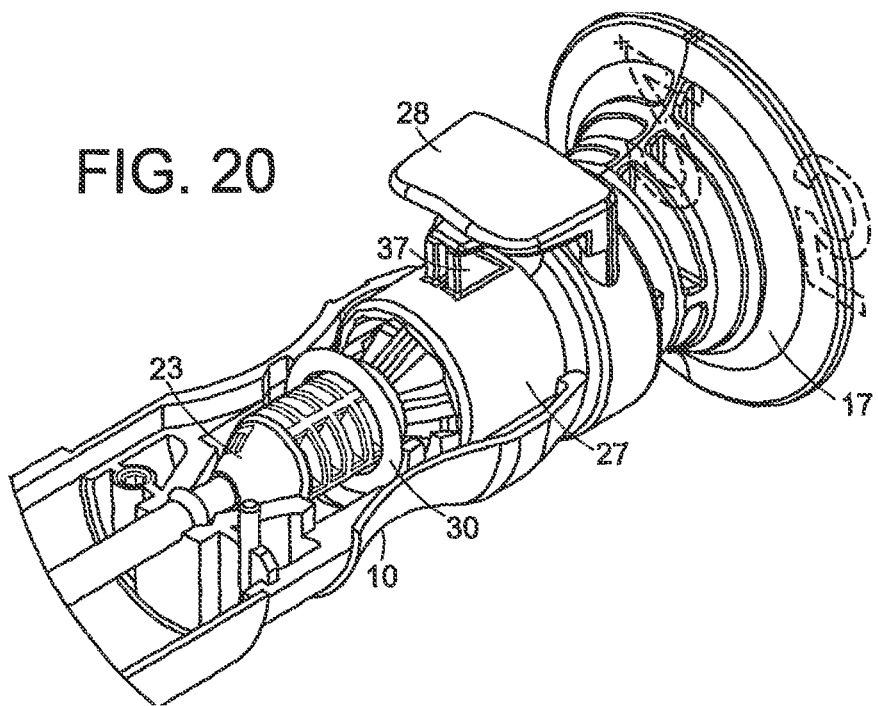
FIG. 20 is a drawing of the intended functionality of the needle protector and aspiration needle assemblies during needle exchange and more specifically, during needle insertion.
Figure 21:
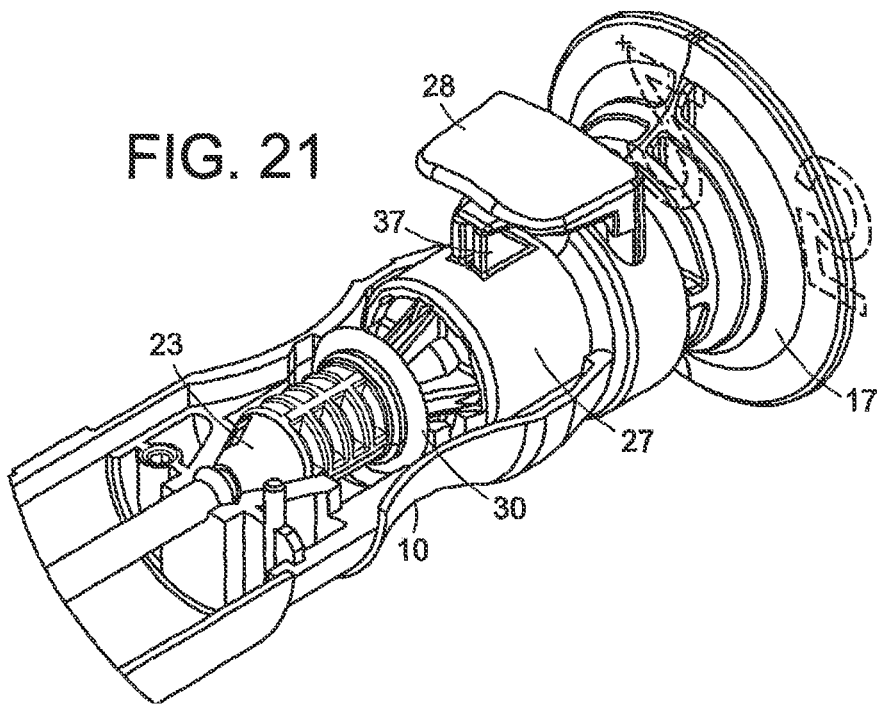
FIG. 21 is a drawing of the intended functionality of the needle protector and aspiration needle assemblies during needle exchange and more specifically, during needle insertion and locking in the device handle.
Figure 22:
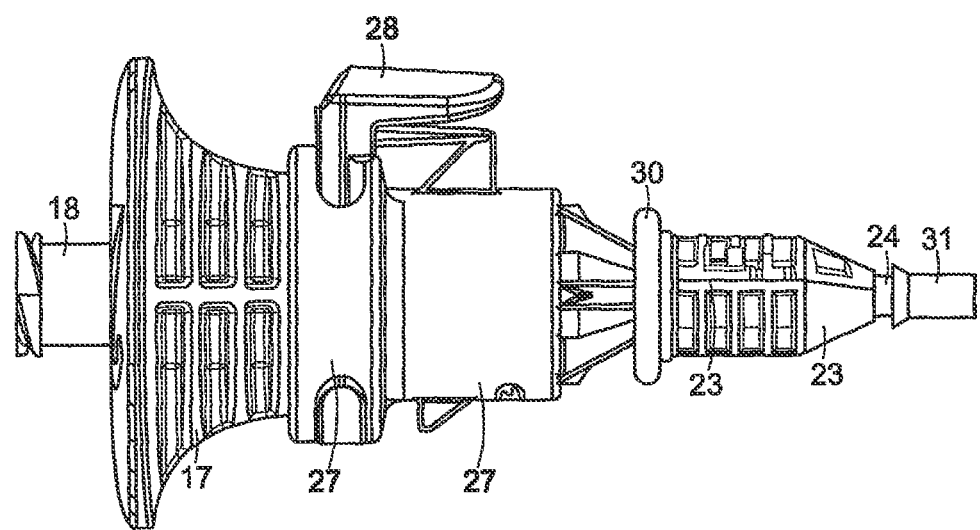
FIG. 22 is a drawing of the locking functionality of the needle protector and aspiration needle sub-assemblies in the hub housing components of the device handle.

FIGS. 20, 21, and 22 illustrate the mechanism by which the aspiration needle sub-assembly 15 is locked into the handle 10 of the delivery system. First, the aspiration needle sub-assembly 15 is pre-mounted with needle protection sub-assembly 9, as previously described. As shown in FIG. 20, at the start of a needle insertion cycle, the aspiration needle/protection assembly is inserted into the proximal handle member 10a of the delivery system handle 10. As the needle/protection assembly is advanced, the needle protector hub 23 contacts the retention collar O-ring component 30. Under application of additional force (as illustrated per FIGS. 18 and 19) the needle collet 19 traverses the internal NP Hub O-ring 25 and advances distally down the catheter sheath 14, as described above. As the needle hub 17 component is advanced into the inner hub housing 27 of the proximal handle member 10a, the distal end of the needle hub 17, contacts the proximal end of the NP sub-assembly 9. Continually inserting the needle hub 17, pushes the NP sub-assembly 9 forward so that the needle protector hub 23 traverses the deformable retention collar O-ring component 30 until it comes to rest. At this juncture, the needle protector hub 23 and sub-assembly 9 are locked in position within the proximal handle member 10a and do not move. Simultaneously, the needle hub 17 deflects the thumb latch 28. Once the NP sub-assembly 9 has traversed the retention collar O-ring component 30 (as shown in FIG. 22), the needle hub 17 is securely locked into the inner hub housing 27 by traversing an internal land ring 36 on the needle hub 17, as shown in Detail F of FIG. 23.

FIG. 23 illustrates a sectional view of the aspiration needle locked into the thumb latch 28/inner hub housing 27 components of the delivery system handle 10. As the needle hub 17 is advanced into the inner hub housing 27 in the handle, the needle hub 17 contacts the internal taper of the thumb latch 28 at the thumb latch distal end. This causes the thumb latch 28 distal end to move laterally and also causing the deflectable hinge member 28a of the thumb latch 28 (see FIG. 26 also) to deform under plastic deformation, against the hub housing barb 37. Once the needle hub 17 is completely advanced into the inner hub housing 27, the distal end portion of the thumb latch 28, returns to the home position. The interference between the internal land ring 36 on the needle hub 17 and the thumb latch distal end, ensures that the needle hub 17 will not move backwards.

Figure 26:
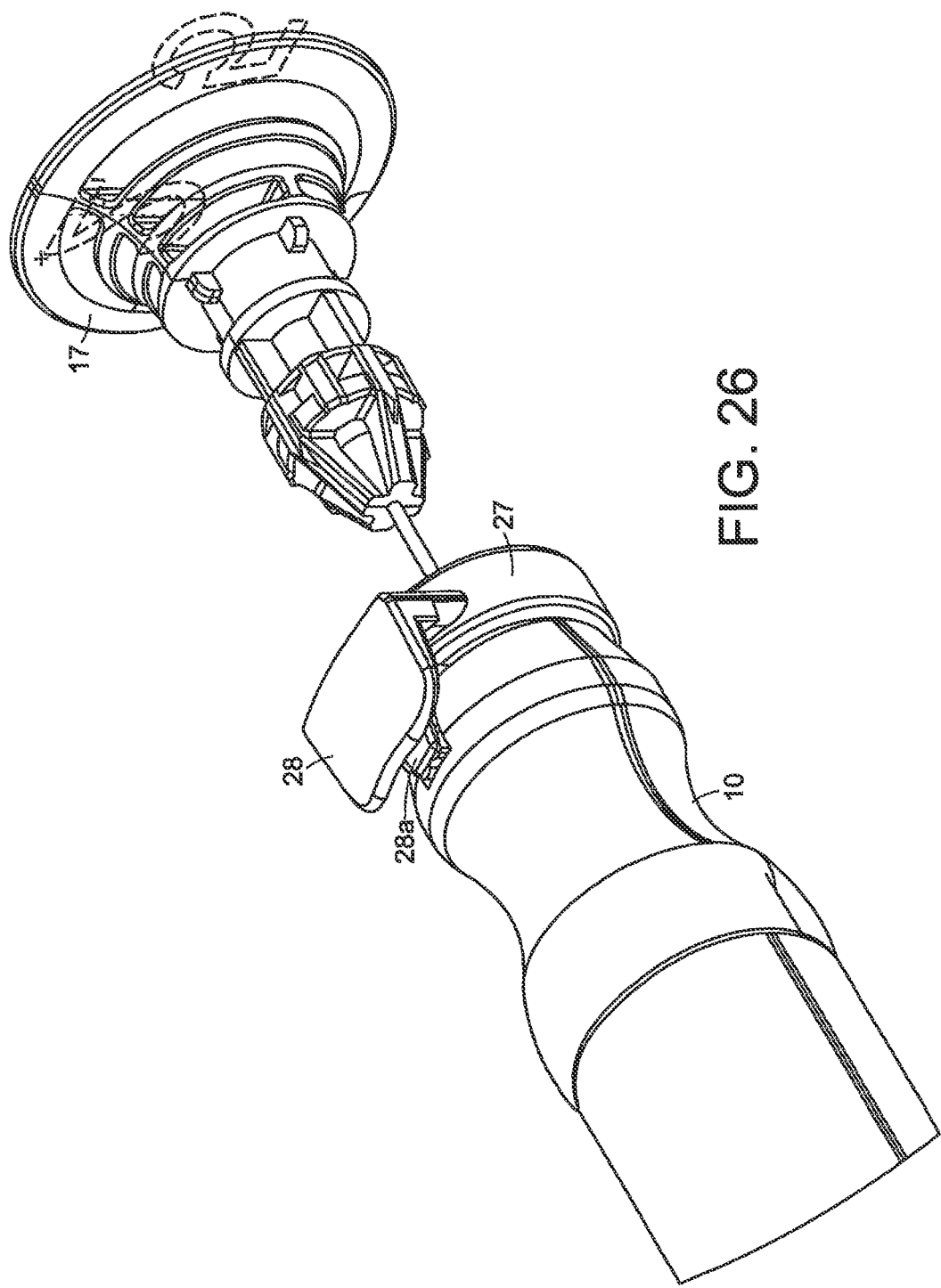
FIG. 26 is a drawing of the intended functionality of the present invention to withdraw the aspiration needle subassembly from the delivery system handle during needle exchange.

An intended functionality of thumb latch 28 is to prevent the aspiration needle subassembly 15 from being removed from the proximal handle member 10a without applying force to release thumb latch 28. As shown in FIG. 26, the aspiration needle may be exchanged or withdrawn from the delivery system handle 10 by depressing the thumb latch 28 and withdrawing the needle hub 17 from the inner hub housing 27. As the thumb latch 28 is depressed, the deflectable hinge member 28a of the thumb latch 28 contacts the hub housing barb 37. The thumb latch 28 moves in a lateral direction. This action clears the interference between the internal land ring 36 and distal end of the thumb latch 28. In this way, the aspiration needle can be removed un-impaired from the delivery system handle. Additionally, follow-up samples may be acquired using the same or a virgin aspiration needle sub-assembly.

Figure 24:
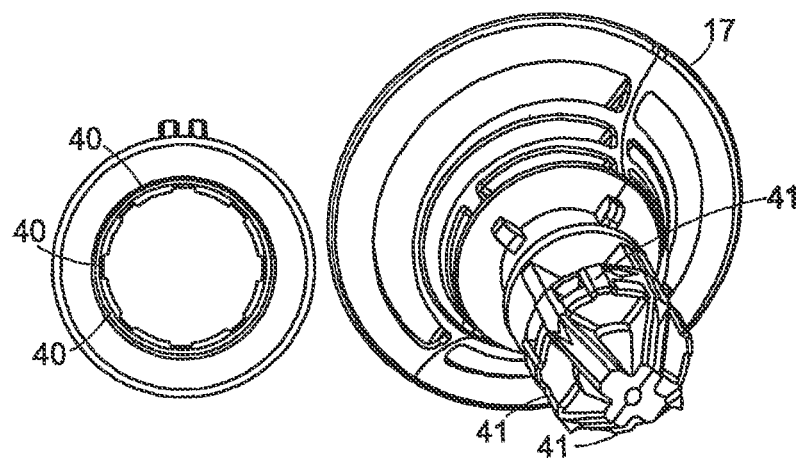
FIG. 24 is a drawing of the hub needle hub and hub housing with interlocking capability to ensure non-rotation.
Figure 25:
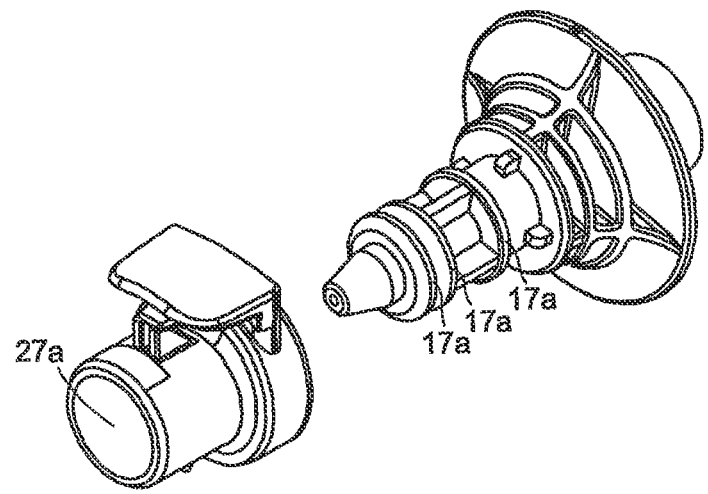
FIG. 25 is an alternate embodiment of the present invention, to facilitate rotation between needle hub and hub housing components.

FIG. 24 illustrates the preferred embodiments of the inner hub housing 27 and needle hub 17 embodiments of the present invention. In this instance, the inner hub housing 27 contains depressed female détentes 40 on the inner diameter of the inner hub housing 27. These détentes 40 are equispaced around the internal circumference of the hub housing body. It is preferable that the number of détente features be in the range of 2 to 15, but more preferably in the range of 6 to 10. These détente features provide a mechanical lock with corresponding interlocking barbs 41 on the external surface of the needle hub 17. Once the needle hub 17 is securely locked in the inner hub housing 27 in the device handle, the interlocking barbs 41 on the needle hub 17 become seated in the détentes 40 of the hub housing. This mechanical lock prevents the needle hub 17 from rotating relative to the inner hub housing 27 and delivery system handle 10, during a typical endoscopic ultrasound procedure. Alternatively, the inner surface of the inner hub housing 27 can be a smooth inner surface 27a. Likewise, the external surface of the needle hub 17 is smooth external surface 17a, to allow the needle hub 17 to rotate relative to the inner hub housing 27 and delivery handle system 10 during an endoscopic ultrasound procedures (FIG. 25).

Figure 28:
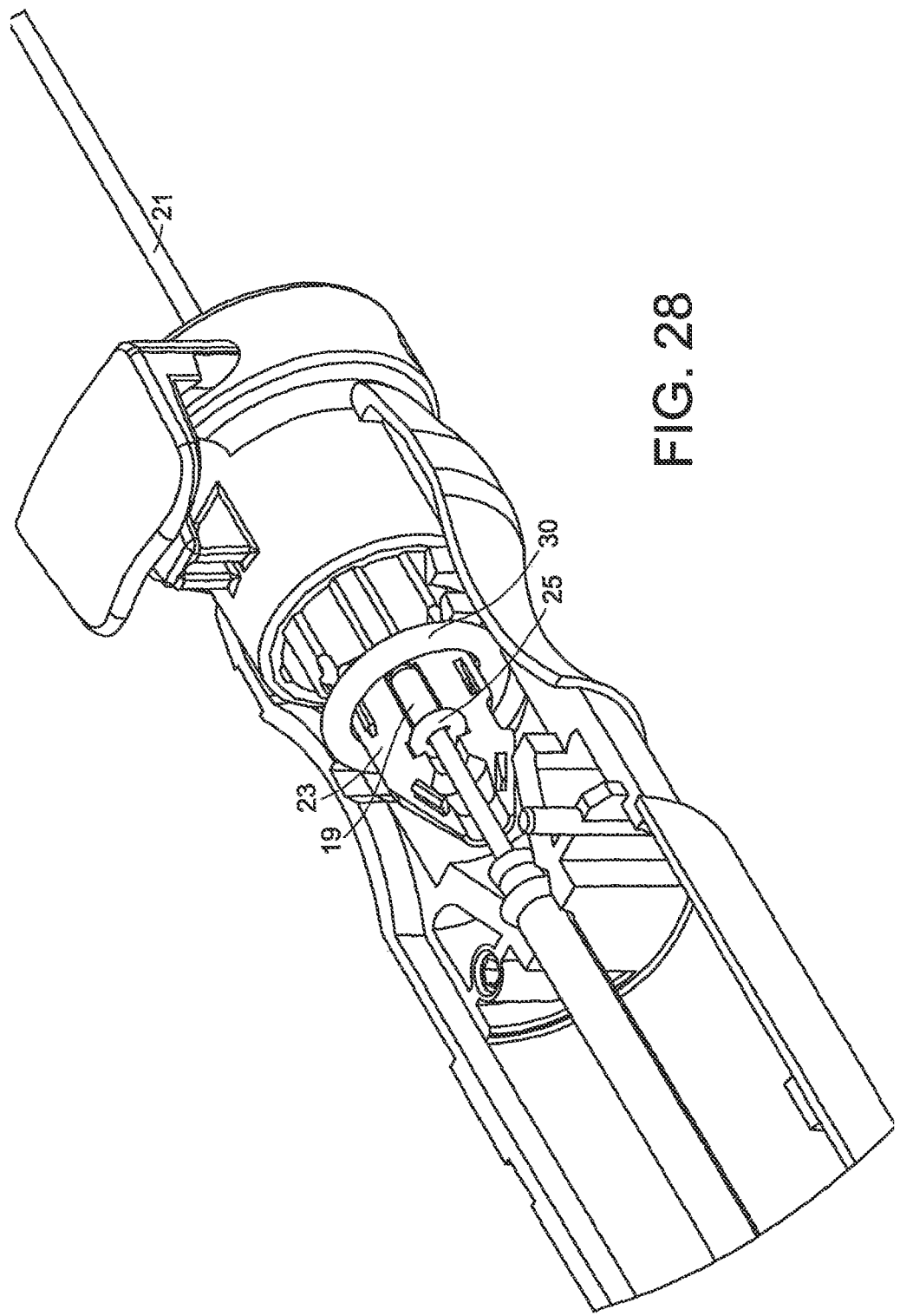
FIG. 28 is a drawing of the intended functionality of the needle collet during needle exchange and more specifically, during needle extraction from the device handle.

During aspiration needle exchange, and more specifically during needle insertion, the needle collet 19 disengages from the NP Hub O-ring 25 by traversing the NP Hub O-ring 25 as explained above. FIGS. 27 and 28 illustrate the engagement of the needle collet 19 with the needle protector sub-assembly 9 upon needle extraction post sample acquisition. As the aspiration needle is continually withdrawn from the delivery system handle 10, the needle collet 19 contacts the NP hub O-ring 25 as shown in FIG. 27. As the aspiration needle is continually withdrawn, the needle collet 19 traverses the NP hub O-ring 25 as shown in FIG. 28. As the needle is further withdrawn, the needle protector hub 23 traverses the retention collar O-ring component 30 and the needle can be completely removed from the system, with the needle protector sub-assembly 9 encasing the distal bevel of the needle bevel 35 to prevent inadvertent "needle sticking", as illustrated in FIG. 29 and Detail G.

Figure 29:
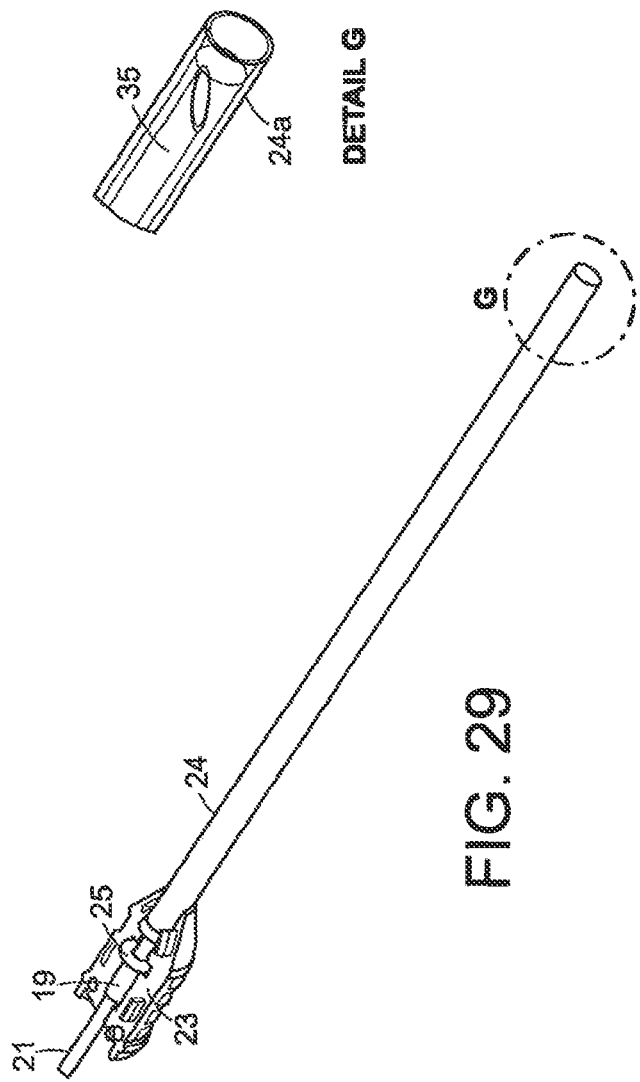
FIG. 29 is a drawing of the needle protector sub-assembly secured to the end of the aspiration needle, and the intended functionality of the needle sheath of the present invention.

In the case of the present invention, the needle protector sheath 24 is internally tapered 24a at the distal end (FIG. 29). It is preferable that length of this internal taper be in the range of 1 mm to 10 mm but more preferably in the range of 3 mm to 6 mm. It is also preferable that the internal taper angle on the distal end of the needle protector sheath be in the range of 2 degrees to 30 degrees, but more preferably in the range of 5 degrees to 15 degrees.

Figure 30:
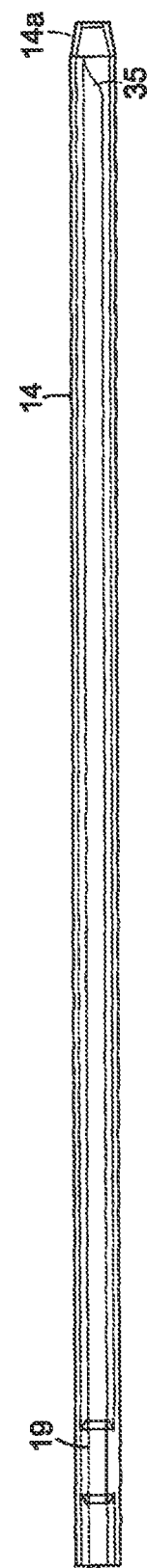
FIG. 30 is a drawing of the distal end of the aspiration needle sub-assembly housed in the catheter sheath of the delivery system of the present invention.
Figure 31:
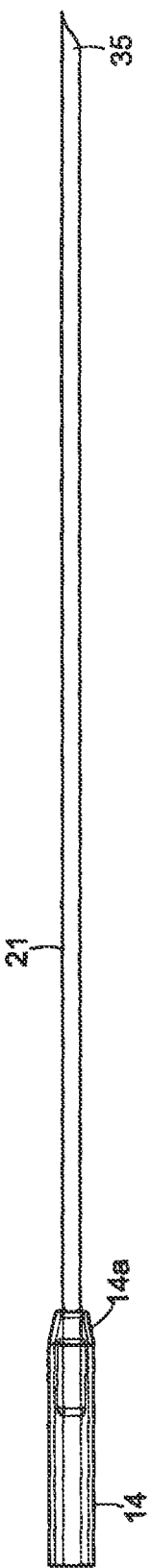
FIG. 31 is a drawing of the distal end of the aspiration needle sub-assembly extending from the catheter sheath of the delivery system of the present invention.

FIG. 30 is an illustration of the distal end 14a of the catheter sheath 14 of the delivery system (not shown) with aspiration needle loaded in the device handle, with the device handle in the fully retracted position. In this instance, the distal end of the needle lies proximal to the distal tapered end 14a of the catheter sheath 14. FIG. 31 illustrates the position of the needle shaft 21 and needle collet 19 relative the catheter sheath 14 when the needle is in a fully extended position. In the fully extended position, the needle collet 19 remains housed inside catheter sheath 14, proximal to the tapered distal tip.

Figure 33:
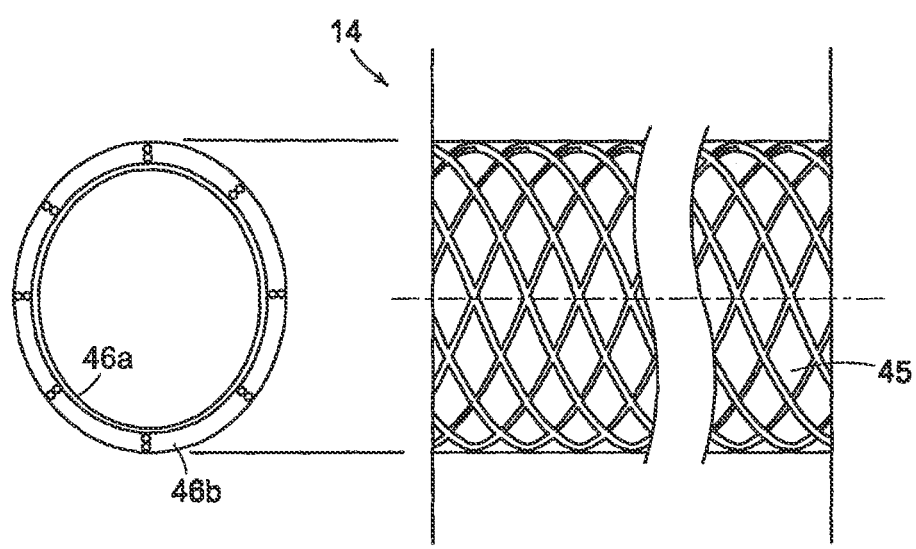
FIG. 33 is a drawing of the construction of the catheter sheath component of the present invention.

In the case of the present invention, the catheter sheath 14 is manufactured from a thermoplastic polymer such as, but not limited to Polyurethane, Polyamide and derivatives thereof, Ether block amide copolymers, Polyimide, Placental, Polyethylene and derivatives thereof, polytetrafluoroethylene. The preferred embodiment of the catheter sheath 14 (as shown in FIG. 33) is that the catheter sheath 14 incorporates a helically braided reinforcing structure 45 housed between inner 46a and outer polymer 46b layers, of outer thermoplastic material such as those mentioned above with a lubricious inner liner or core. In the case of the present invention, the helically braided reinforcing structure 45 is fabricated from stainless steel wire. It is preferable that the diameter of this reinforcing braid wire be in the range of 0.0005 inches to 0.010 inches but more preferably in the range of 0.0015 inches to 0.005 inches It is preferable that the outer diameter of the catheter sheath 14 be in the range of 0.050 inches to 0.140 inches but more preferably in the range of 0.085 inches to 0.0105 inches. It is preferable that the inner diameter of the catheter sheath 14 be in the range of 0.050 inches to 0.120 inches but more preferably in the range of 0.065 inches to 0.085 inches.

In the case of the present invention (and as illustrated in FIGS. 30 and 31), it is preferable that the distal end 14a of the catheter sheath 14 be tapered to reduce both the outer diameter and the internal diameter of the catheter sheath tip. This taper may be imparted to the distal end of the catheter sheath 14 via swaging or thermal heat forming techniques. It is preferable that the inner diameter of the catheter sheath 14 be tapered at the distal end 14a to an internal diameter in the range of 0.020 inches to 0.060 inches but more preferably in the range of 0.040 inches to 0.050 inches.

Figure 32:
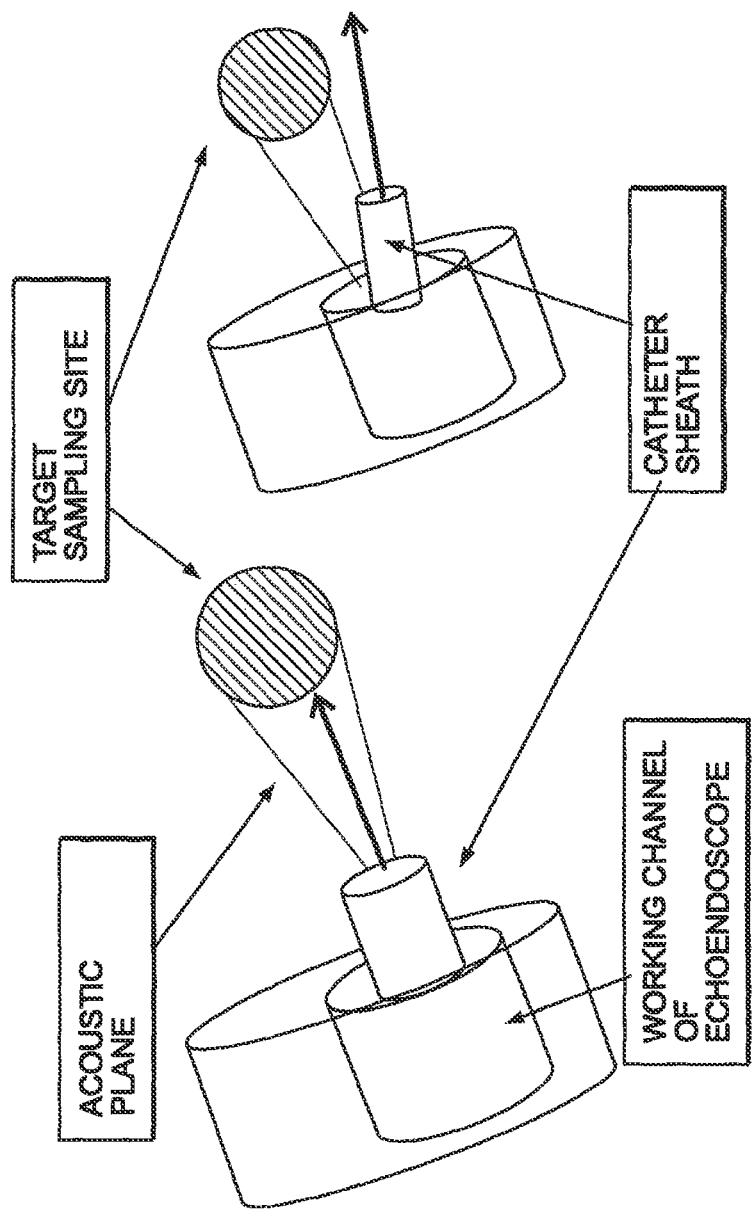
FIG. 32 is a drawing of the intended functionality of the present invention, and more specifically of the intended functionality of the catheter sheath of the present invention.

Referring now to FIG. 32, An aspect of the present invention which provides the clinician with improved procedural performance over prior art devices, concerns the ability of the tapered catheter sheath 14 of the present invention to keep the aspiration needle of the device centered in the working channel conduit of the endoscope. Due to the increased outer diameter of the catheter sheath 14 of the present invention (in the range of 6.5 French to 8 French) compared to that of the prior art (approximately 5 French to 5.4 French), the catheter sheath reduces the annular clearance between the catheter sheath 14 and the inner diameter of the endoscope working channel. By reducing the annular clearance with the working channel of the endoscope, the angle of exit of the catheter sheath 14 of the present invention is coaxial to working channel. This ensures that as the needle exits the distal end of the catheter sheath, the needle will exit the distal end of the catheter in a more "normal" plane relative to the longitudinal axis of the endoscope. The inclusion of an internal taper on the distal end of the catheter sheath, also ensures that the needle exits the catheter in a more "normal" plane than in the case of prior art devices.

Figure 34:
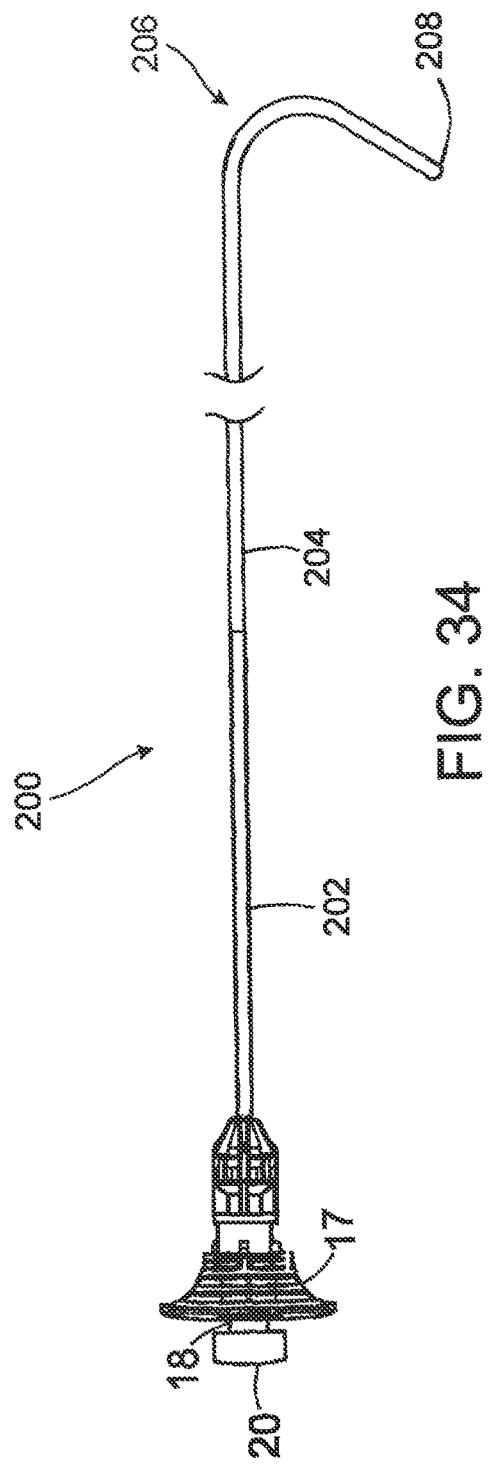
FIG. 34 is a side view of an access catheter subassembly of the present invention.

FIG. 34 is a side view of an access catheter subassembly of the present invention. As previously described here, the access catheter assembly of the present disclosure may be used in conjunction with minimally-invasive procedures. For example, an access catheter consistent with the present disclosure may be compatible for use with exemplary endoscopic delivery systems and methods discussed in Needle Biopsy Device with Exchangeable Needle and Integrated Needle Protection, U.S. Pub. 2012/0116248, Rapid Exchange FNA Biopsy Device with Diagnostic and Therapeutic Capabilities, U.S. Pub. 2011/0190662, Device for Needle Biopsy with Integrated Needle Protection, U.S. Pub. 2010/0121218, and Needle Biopsy Device, U.S. Pub. 2010/0081965, the contents of each of which are hereby incorporated by reference in their entirety.

As shown in FIG. 34, an access catheter assembly includes an access catheter 200 configured to gain access to and navigate a desired vessel for subsequent treatment thereof. In embodiments described herein, the access catheter 200 is configured to gain access to one or more tissues/organs associated with the pancreaticobiliary system for the purpose of providing treatment. For example, the access catheter 200 may be used, in conjunction with the endoscopic delivery device previously described herein, to gain access and navigate at least the common biliary duct via an Endoscopic Ultrasound-Guided Fine-Needle Aspiration (EUS-FNA) technique and to further allow procedures to treat narrowed areas or blockages within the bile duct, including palliative drainage procedures. Accordingly, an access system (access catheter assembly and endoscopic delivery device) consistent with the present disclosure is configured to provide Endoscopic Ultrasound Guided Biliary Drainage (EUS-BD). However, it should be noted that the access system of the present invention is not limited to the pancreaticobiliary system. The access system of the present invention can be used to provide access to a variety of different systems of the human body, particularly where maneuverability and accuracy is desirable.

Figure 35:
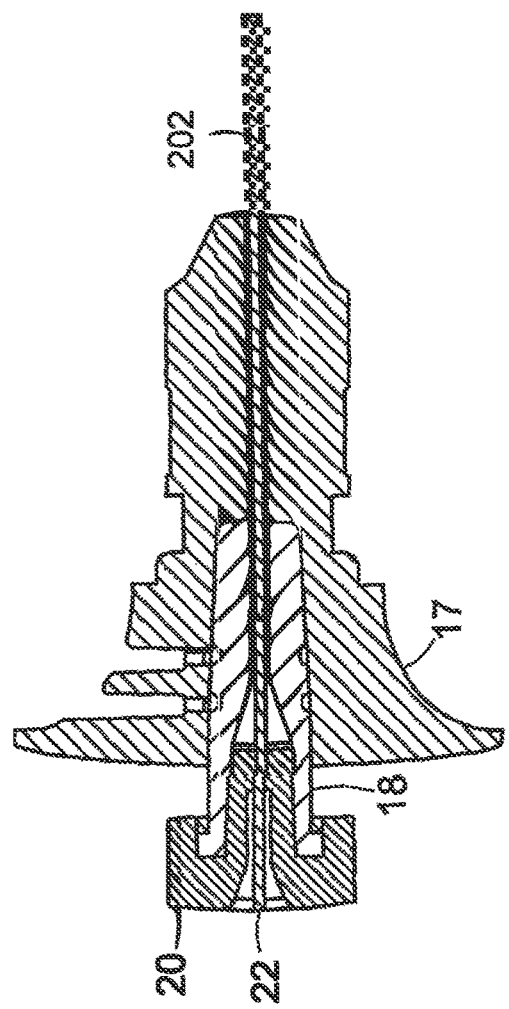
FIG. 35 is a cross sectional view of the proximal end of the access catheter subassembly of FIG. 34.

The access catheter 200 generally includes an elongate tubular body having a proximal section 202 having a proximal end, a distal section 204 having a distal end 208, an outer surface, and an inner surface defining a lumen extending from the proximal section 202 to the distal section 204. The distal section 204 further includes an adjustable portion 206 along a length thereof configured to transition to at least a pre-defined arcuate shape under certain conditions. The proximal section 202 of the catheter 200 is coupled to a catheter hub 17, which is similarly configured as needle hub 17 previously described herein and generally functions in the same manner. As shown in FIG. 35, the access catheter 200 may be configured to receive at least a stylette shaft 22 within. As described in greater detail herein, the stylette may be used during an EUS-BD rendezvous procedure, in which a tip of the stylette may be used to pierce through a wall of the duodenum tissue and through a wall of the common biliary duct (CBD) so as to allow the catheter 200 to gain access into and further navigate the CBD.

The access catheter 200 may have variable stiffness throughout its length. For example, in one embodiment, the proximal and distal sections 202, 204 may have different levels of stiffness. In one embodiment, the proximal section 202 may have a greater level of stiffness than the distal section 204. In some embodiments, the proximal and distal sections 202, 204 may be constructed of the same material, but may have different thickness thereby resulting in different levels of stiffness. For example, the proximal section 202 may have thicker wall while the distal section 204 has a thinner wall, thereby resulting in the proximal section 202 being rigid and the distal section 204 being more flexible.

In other embodiments, the proximal and distal sections 202, 204 may be constructed of different materials that result in different levels of stiffness. For example, the proximal section may be constructed of a relatively rigid material including, but not limited to, various metals (stainless steel, Nitinol, or alloys thereof) and polymers (rigid polyamide, polyurethane, or copolymers thereof). Additionally, or alternatively, the proximal section 202 be braided in construction consisting of inner and outer polymeric jackets, encasing stainless steel braid wire wound in a helically fashion, as generally understood by one skilled in the art.

The distal section 204 may be constructed of a relatively durable and flexible material including, but not limited to, a non-reinforced polymer extrusion from materials such as polyamide, polyurethane, or co-polymer derivatives thereof. In some embodiments, the distal section 204 may be constructed of polymer with braid wire reinforcement, such as previously described.

The proximal section 202 is tubular in design and may have an outer diameter in the range of approximately 0.1 to 0.3 cm. The proximal section 202 may have an inner diameter in the range of 0.03 to 0.3 cm. The transition from the proximal section 202 to the distal section 204 may be located between 5 and 150 cm from the needle hub 17. In some embodiments, the transition is located between 80 and 120 cm from the hub 17. The flexible distal section 204 is of tubular construction and may have an outer diameter in the range of 0.08 and 0.3 cm. In some embodiments, the distal section 204 may have an outer diameter in the range of 0.1 to 0.2 cm.

Figure 36:
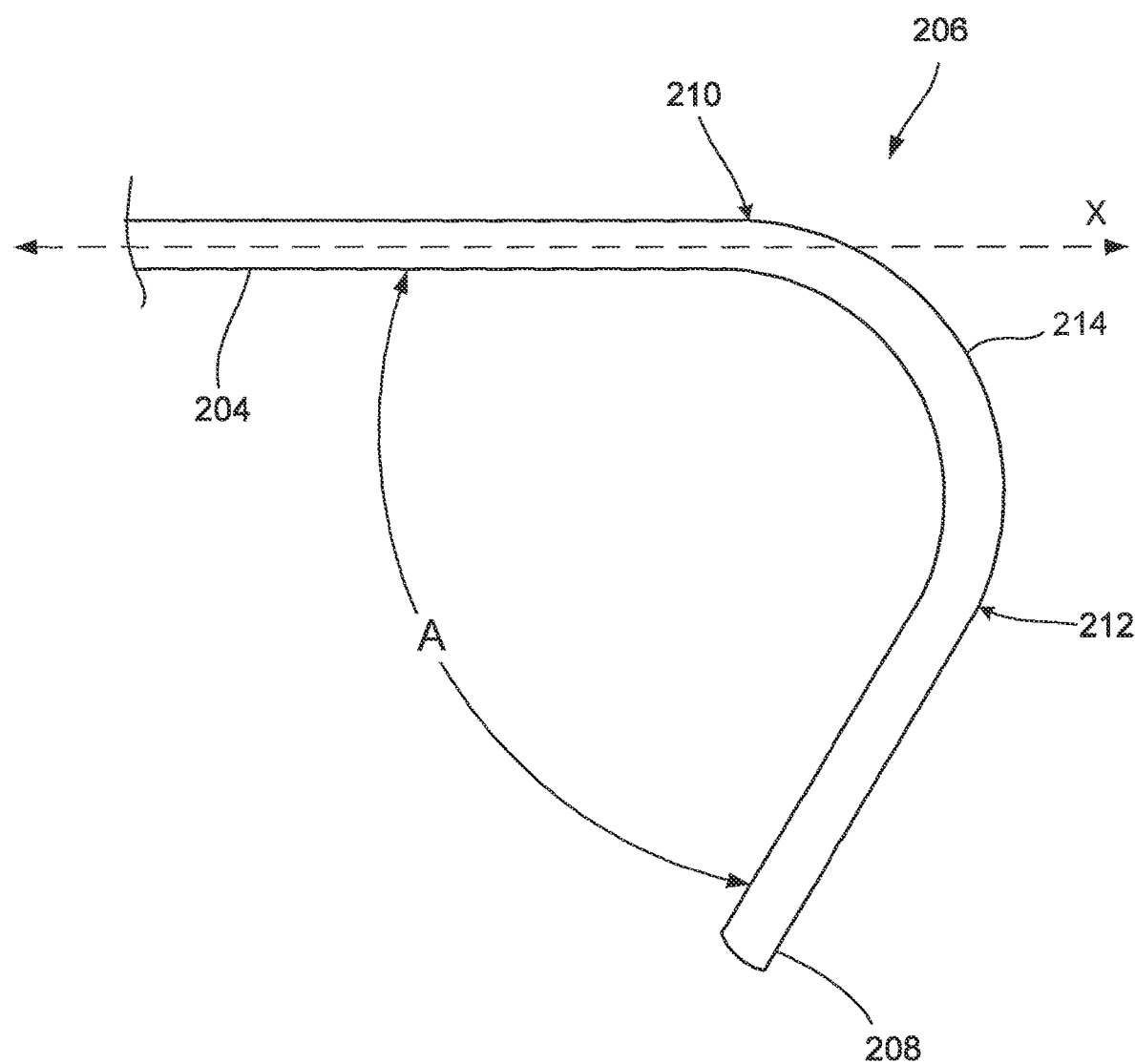
FIG. 36 is a side view of a distal section of an access catheter of the present invention.

FIG. 36 is a side view of a distal section of an access catheter 200 of the present invention. As shown, the adjustable portion 206 is configured to transition to a pre-defined arcuate shape under certain conditions. The adjustable portion 206 generally forms a curved shape relative to the longitudinal axis X defined by a lumen of the catheter body. The curved shaped generally has a first transition portion, indicated by arrow 210, upon which the catheter body extends along a curved path until a second transition portion, indicated by arrow 212, at which point the catheter body extends in a relatively linear path to the distal end 208. Accordingly, the adjustable portion 206 has an arcuate-shaped portion 214 between the first and second transition portions 210, 212. The curve styles may vary in length and angulation depending upon the specific tissue/organ and/or location inch which the catheter 200 is to be inserted. When in the pre-defined arcuate shape, the adjustable portion 206 forms at least one angle A relative to a longitudinal axis X defined by the lumen of the catheter body. In one embodiment, the at least one angle A is between 0 and 170 degrees. In some embodiments, the at least one angle A is between 30 and 140 degrees. In another embodiment, the at least one angle A is between 45 and 120 degrees. In another embodiment, the at least one angle A is between 60 and 100 degrees. In a preferred embodiment, the at least one angle A is between 90 and 170 degrees. It should be noted that the adjustable portion 206 may include more than one curved section. For example, the adjustable portion 206 may be of a pigtail configuration, or the like. The different shapes and ranges of curve angles is configured to provide the clinician with sufficient angle options so as to satisfy the variation in anatomy and aid in guidewire advancement.

Figure 37A:
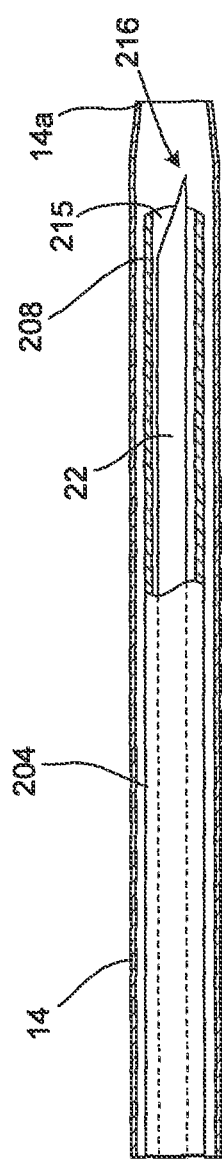
FIG. 37A is a side view, partly in section, of storage of the access catheter within the sheath of FIG. 34 including a stylette positioned within the access catheter.

FIG. 37A is a side view, partly in section, of storage of the access catheter 200 within the catheter sheath 14 of FIG. 5 including a stylette shaft 22 positioned within the access catheter 200. As previously described herein, the access catheter 200 is to be used in conjunction with the delivery system handle 10 previously described herein. Accordingly, the access catheter 200, as well as the hub 17, may be removably disposed within the inner lumen of the delivery handle assembly and lumen of the catheter sheath 14. In this instance, a stylette shaft 22 is also positioned within the lumen 215 of the catheter 200. A shown, when disposed within the lumen of the catheter sheath 14, the adjustable portion 206 of the access catheter 200 is configured to maintain a substantially linear shape, or at the very least, maintain a shape that corresponds to contour of the catheter sheath 14. In other words, while loaded within the catheter sheath 14, the distal section 204, including the adjustable portion 206, are constructed of sufficiently flexible materials configured to correspond to the shape of the lumen of the catheter sheath 14.

Figure 37B:
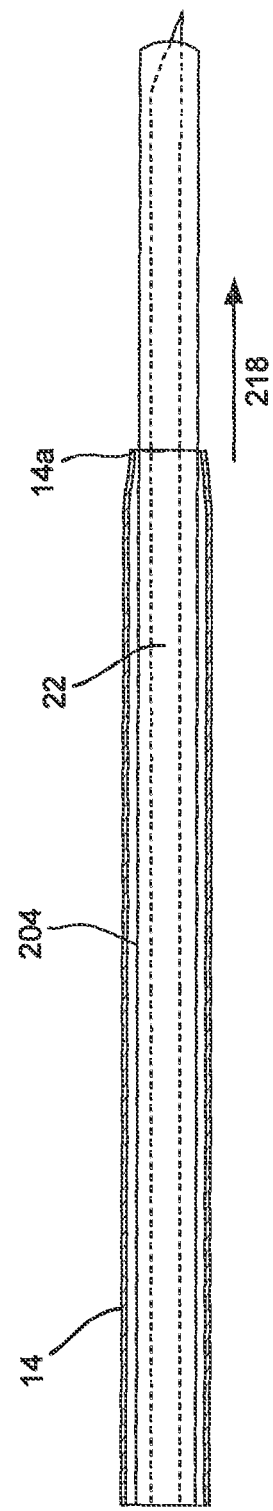
FIG. 37B is a side view, partly in section, of extension of the access catheter and stylette of FIG. 37A from the sheath of FIG. 34.

As shown in FIG. 37B, even upon extension of the access catheter 200 and stylette shaft 22, as indicated by arrow 218, the adjustable portion 206 of the catheter 200 is configured to maintain a substantially linear shape. In particular, while the relatively rigid stylette shaft 22 is positioned within the distal section 204, specifically the adjustable portion 206, of the catheter 200, the adjustable portion 206 is prevented from transitioning to the pre-defined arcuate shape. In this instance, the distal pointed tip 216 of the stylette shaft 22 can be used to pierce the tissue of a vessel (e.g., pierce the wall of the duodenum and the wall of the common biliary duct) so as to allow the catheter 200 to gain access to the vessel.

Figure 37C:
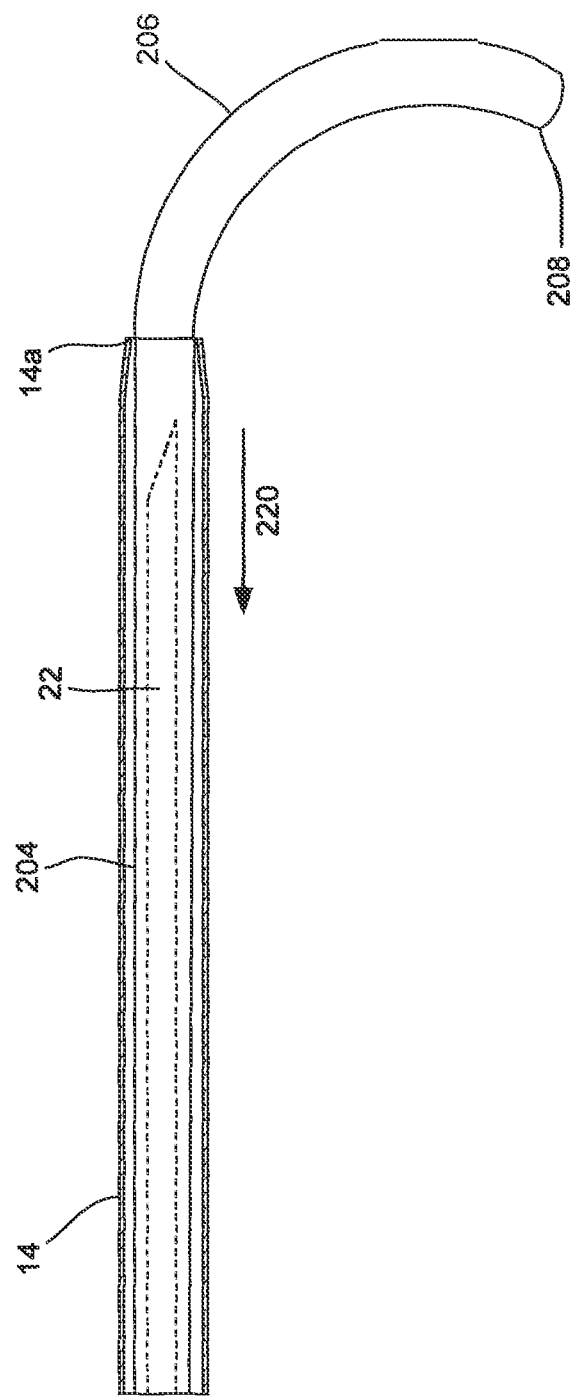
FIG. 37C is a side view, partly in section, of withdrawal of the stylette from within a portion of the distal section of the access catheter.

FIG. 37C is a side view, partly in section, of withdrawal of the stylette shaft 22 from within a portion of the distal section 204 of the access catheter 200. As shown, upon withdrawal of the stylette, as indicated by arrow 220, the adjustable portion 206 is configured to transition to the pre-defined arcuate shape. This will generally occur once adjustable portion 206 has been guided through the puncture between the duodenum and common biliary duct. Accordingly, the adjustable portion 206 may be constructed of flexible materials having shape memory properties. As shown in FIG. 37D, further extension of the access catheter 200 from the catheter sheath 14, as indicated by arrow 222, may result in the adjustable portion 206 fully transitioning to the arcuate shape. At this point, the lumen of the catheter 200 at the distal end 208 may be in relative coaxial alignment with the lumen of the common biliary duct, thereby providing a clinician with an improved initial access to the duct for additional tools (e.g., guidewire) to continue the biliary drainage procedure.

Figure 38:
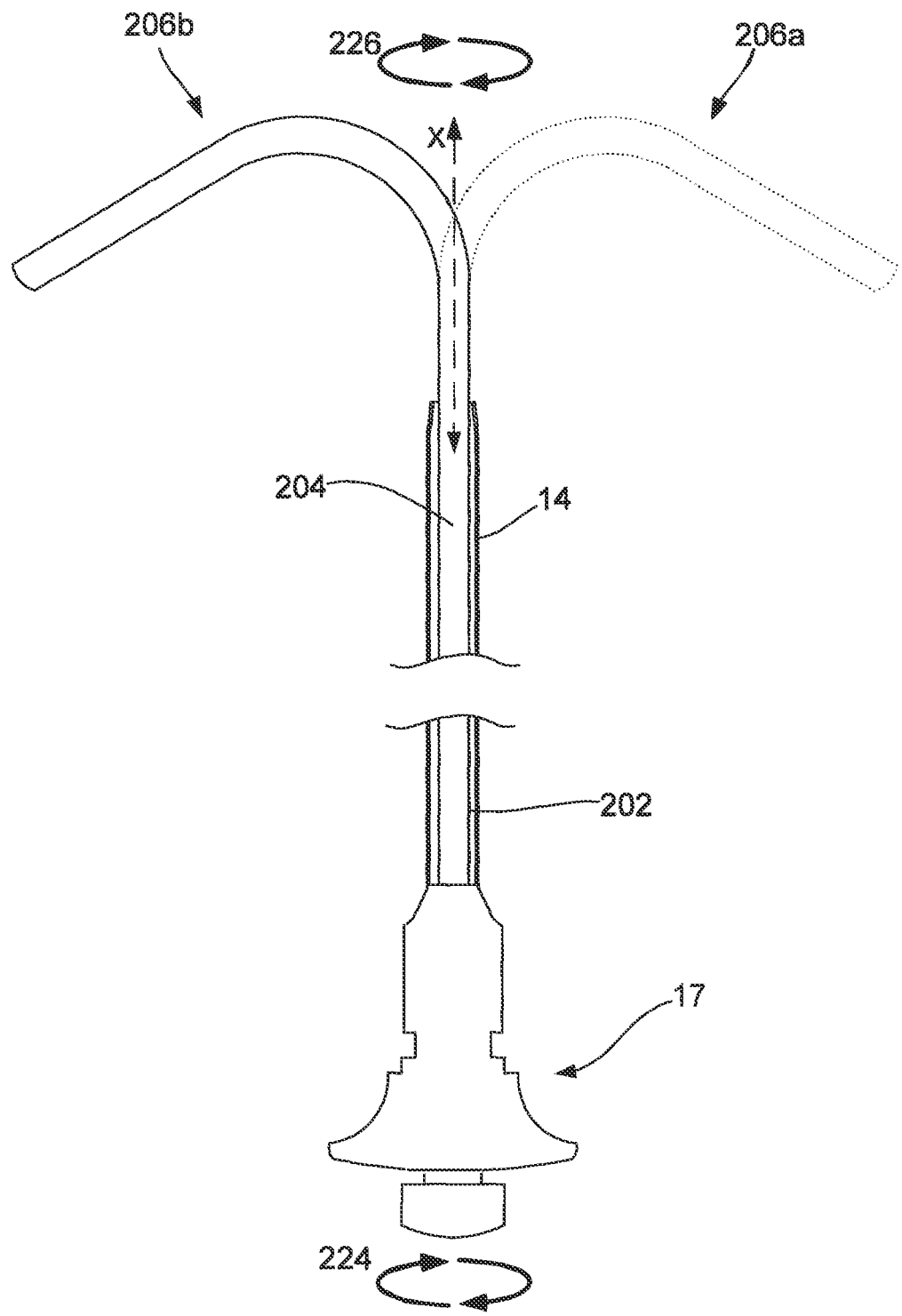
FIG. 38 is a side view, partly in section, of the extended distal end of the access catheter illustrating manipulation of the distal end based on rotational movement of a catheter hub.

FIG. 38 is a side view, partly in section, of the extended distal end 208 of the access catheter 200 illustrating manipulation of the distal end 208 and adjustable portion 206 based on rotational movement of a catheter hub 17. As described in greater detail herein, the handle assembly 10 includes one or more elements configured to allow a clinician to maneuver and manipulate the adjustable portion 206 and distal end 208 of the access catheter 200 while navigating the vessel. For example, a clinician may rotate the catheter hub 17, as indicated by arrow 224, which, in turn, results in rotational movement of the adjustable portion 206 and distal end 208, as indicated by arrow 226. Accordingly, a clinician may be able to manipulate the catheter 200 so as to better navigate the vessel. The adjustable portion 206 may rotate incrementally within a range of 0 to 360 degrees relative to the longitudinal axis X. For example, the clinician may rotate the hub 17 approximately 180 degrees, thereby resulting the adjustable portion rotating 180 degrees (206a position to 206b position).

Figure 39:
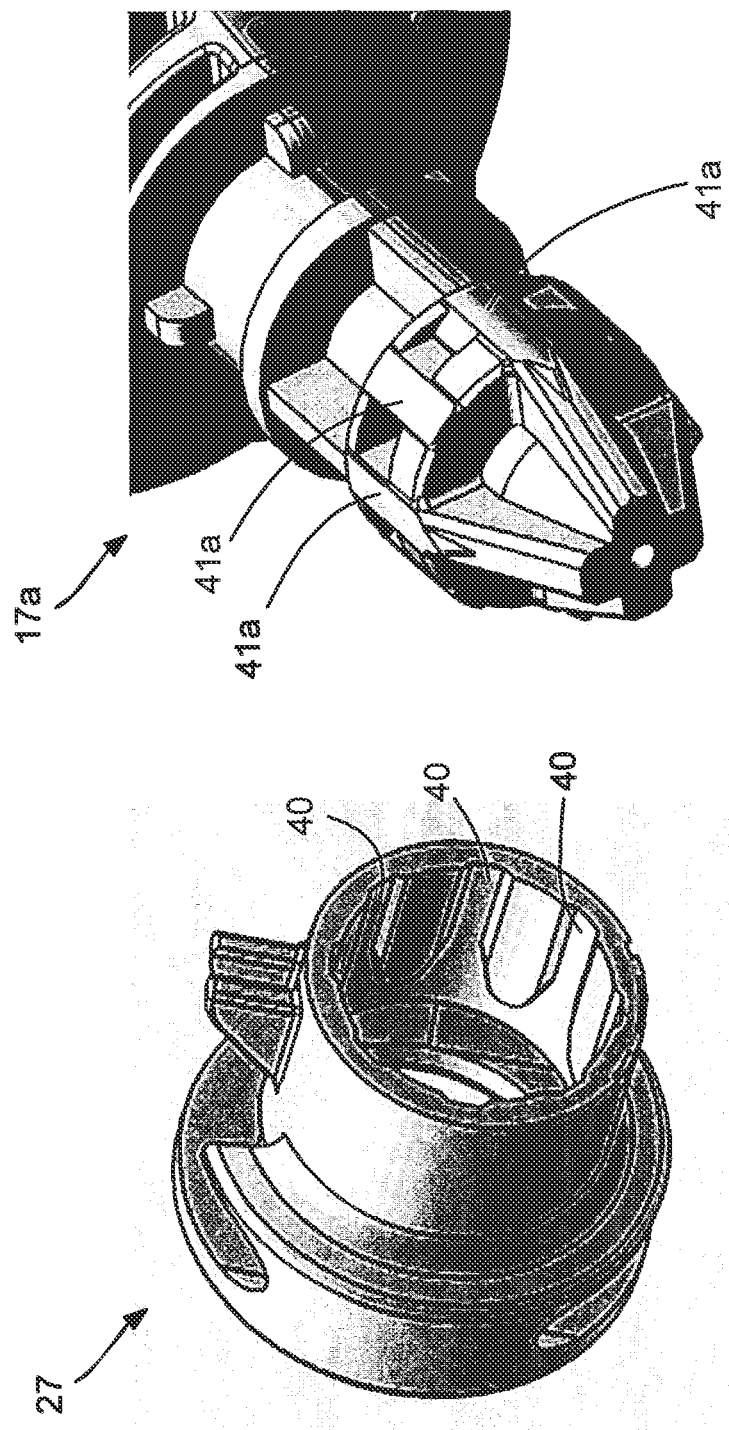
FIG. 39 is a perspective view of the inner hub housing of the delivery handle assembly and the catheter hub of the access catheter assembly.

FIG. 39 is a perspective view of the inner hub housing 27 of the delivery handle assembly 10 and the catheter hub 17 of the access catheter assembly. As previously described herein, and shown in FIG. 24, the inner hub housing 27 contains depressed female détentes 40 positioned between adjacent radially spaced barbs on the inner diameter of the inner hub housing 27. These détentes 40 are equispaced around the internal circumference of the hub housing body. The détente features provide a mechanical lock with corresponding interlocking barbs 41a on the external surface of the catheter hub 17. Each of the second plurality of barbs 41a are configured for selective engagement with a corresponding one of the first plurality of barbs and the corresponding female détentes 40 so as to permit incremental rotation of the catheter hub 17 relative to the inner hub housing 27. Each of the second plurality of barbs 41a differ from the barbs 41 previously described herein in that the barbs 41a have a reduced height so as to provide incremental interference. In other words, rather than being completely locked into corresponding détentes, the reduced height of the barbs 41a allows a temporary engagement, wherein, upon sufficient rotational force, the each barb 41a can move incrementally from détente to détente. Accordingly, the distal section 204, specifically the adjustable portion 206 and distal end 208 of the access catheter 200 is configured to incrementally rotate about the longitudinal axis X in conjunction with incremental rotation of the catheter hub 17. As such, upon removal of rotational force, engagement between inner hub housing 27 and catheter hub 17 is sufficient to ensure that the distal section, particularly the adjustable portion 206, remains fixed the desired location and does not whip, and further allows a clinician may remove their grip from the handle assembly, while the position of the distal section is maintained.

Figure 40:
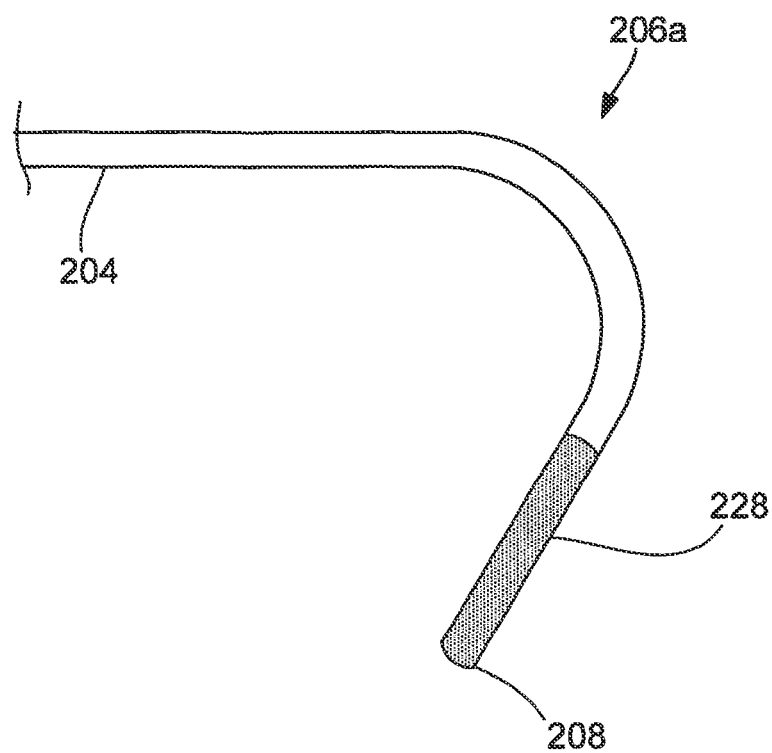
FIG. 40 is a side view of another embodiment of a distal section of an access catheter of the present invention.

FIG. 40 is a side view of another embodiment of a distal section of an access catheter of the present invention. As shown, the adjustable portion 206a may include a metallic distal tip 228 adjacent to the distal end 208. The metallic distal tip 228 may be coupled to the catheter by any known techniques. For example, in one embodiment, the metallic distal tip 228 may be thermally bonded to the distal end 208 of the catheter 200. The metallic distal tip 228 may provide sufficient durability and column strength and pushability for allowing the distal end 208 to puncture through relatively tough, dense, and/or fibrous tissue, such as through the duodenal or gastric walls and into the biliary tree. The metallic distal tip 228 may vary in length between 2 and 30 mm. In one embodiment, the metallic distal tip 228 may have a length in the range of 2 to 10 mm. The outer surface of the metallic distal tip 228 enhanced echogenicity or acoustic reflection. For example, this echogenically enhanced region can be fabricated by, but not limited to, roughening the metallic distal tip 228 over a pre-defined length. The length of the echogenically enhanced region may be in the range of 2 mm to 20 mm, but is more preferably in the range of 10 mm to 15 mm. The echogenic enhanced pattern may be imparted to the metallic distal tip 228 via a micro-blasting process which roughens the surface of the catheter over a specific length, improving the visibility of the metallic distal tip 228 under endoscopic ultrasound. Other surface roughening techniques may be used, such as laser or chemical etching. In other embodiments, the echogenically enhanced region of the metallic distal tip 228 may be achieved through the removal of material from the surface of the metallic distal tip 228 to provide greater reflectivity and strengthened reflected signal.

Figure 41:
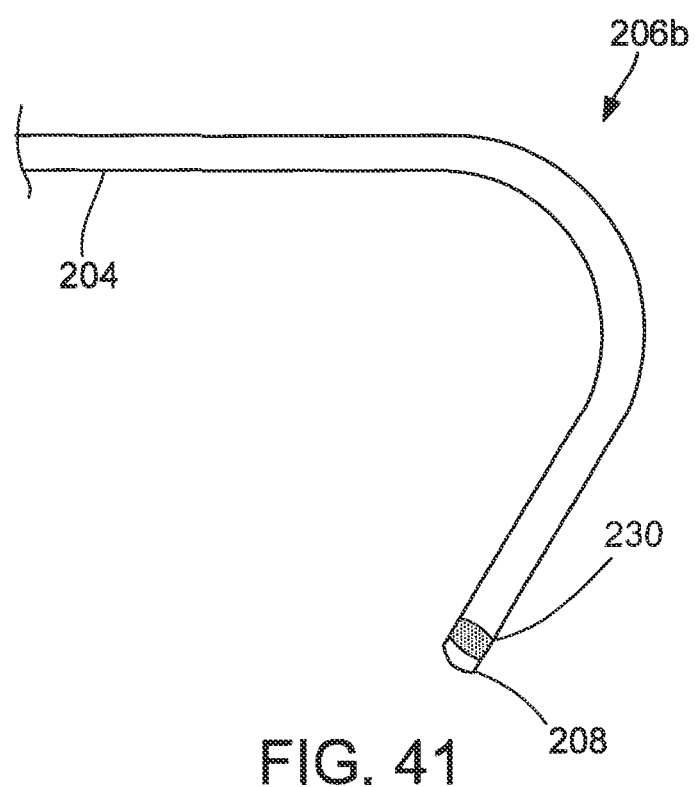
FIG. 41 is a side view of another embodiment of a distal section of an access catheter of the present invention.

FIG. 41 is a side view of another embodiment of a distal section of an access catheter of the present invention. In the illustrated embodiment, the access catheter 200 further includes a cutting element 230 positioned on the adjustable portion 206b and adjacent to the distal end 208. As generally understood, the cutting element 230 may be embodiment as any element configured to excise, cut, ablate, or otherwise remove tissue and/or debris. For example, the cutting element 230 may include, but is not limited to, a dielectric cautery ring, cutting knife, a cutting wire, pinching cutters, or the like. The cutting element 230 is configured to allow the clinician to ablate/cut through tissue so as to widen an obstructed pathway and/or completely remove a tumor or other obstruction (e.g., gallstone).

Figure 42:
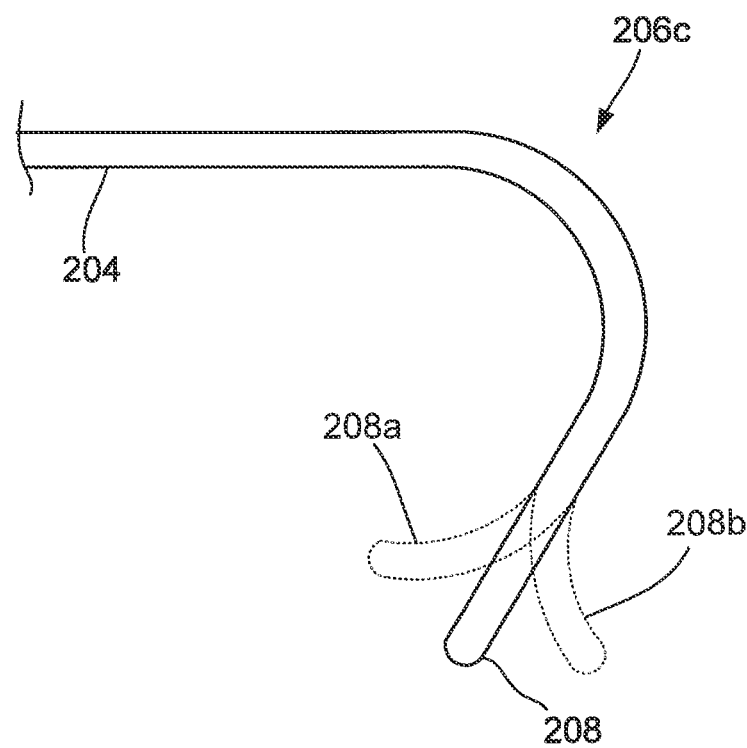
FIG. 42 is a side view of another embodiment of a distal section of an access catheter of the present invention.
Figure 43:
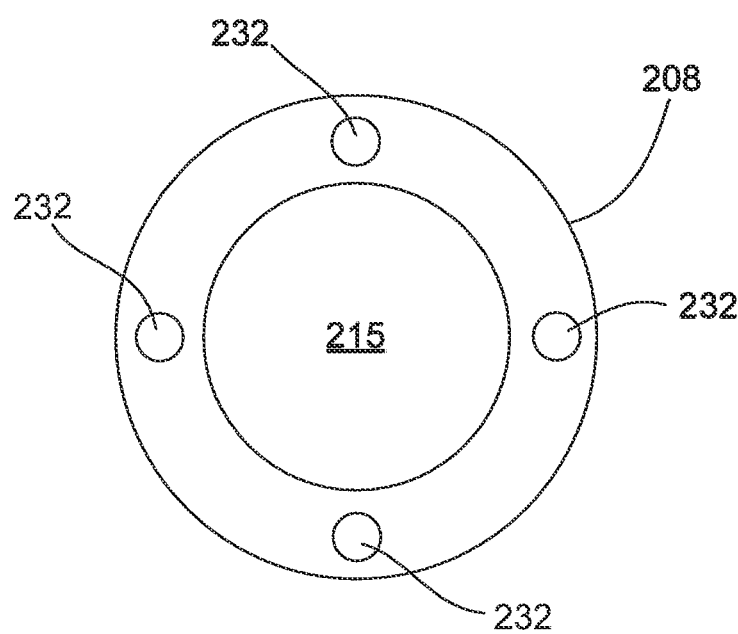
FIG. 43 is a cross sectional view of a portion of the distal section of the access catheter of FIG. 42.

FIG. 42 is a side view of another embodiment of a distal section of an access catheter of the present invention and FIG. 43 is a cross sectional view of a portion of the distal section of the access catheter of FIG. 42. As shown, the access catheter 200 may further includes at least one control element configured to cause movement of at least the distal end 208 and/or the adjustable portion 206c of the catheter 200 relative to a longitudinal axis X. For example, the catheter 200 may have steerable functionality, such that one or more control, or steering, wires 232 may be positioned within and anchored to at least the distal section 204 of the catheter 200, such that force applied to the one or more control wires 232 results in manipulation of at least the distal end 208 (shown as 208a, 208b). Control over the control wires 232 may be provided within the handle assembly 10 and/or separately on the catheter hub 17. Accordingly, upon a clinician applying tension to one or more control wires 232, at least the distal end 208 will move so as to provide improved manipulation for improving navigation of the catheter 200.

Figure 44:
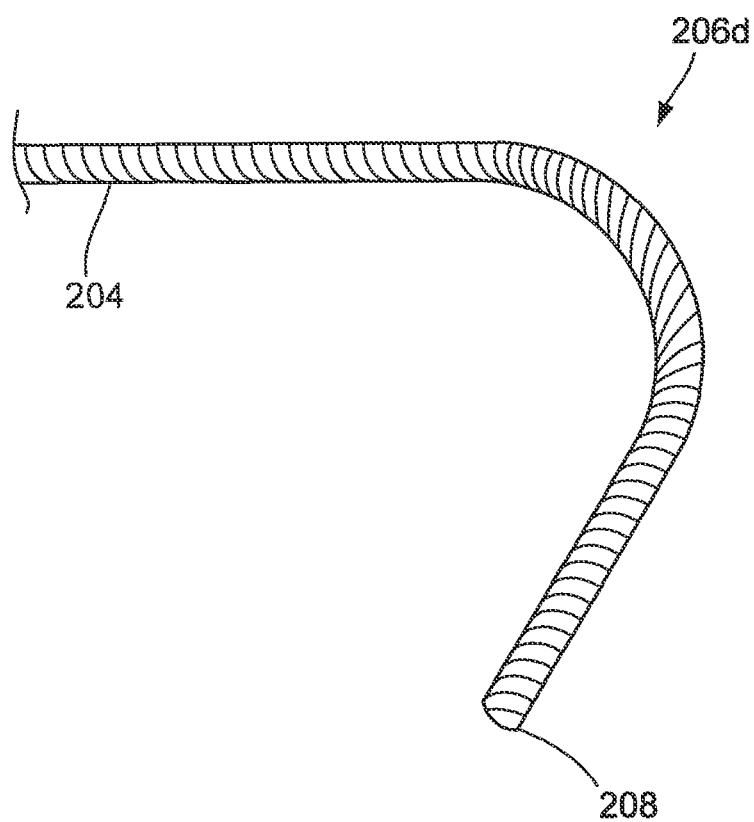
FIG. 44 is a side view of another embodiment of a distal section of an access catheter of the present invention.

FIG. 44 is a side view of another embodiment of a distal section of an access catheter of the present invention. As shown, at least the distal section 204 of the catheter 200 includes a tubular body formed from densely packed tubular coil. In some embodiments, the interior surface of the lumen of the distal section 204 has a liner disposed thereon having a relatively low coefficient of friction. For example, the liner may be a polytetrafluoroethylene (PTFE) liner. By providing a line having a low coefficient of friction, lubricity is enhance lubricity and guidewire movement. Additionally, such a coiled configuration is configured to enhance flexibility for access catheter advancement while also enhancing torque transmission from the hub 17 during rotational manipulation.

Accordingly, the access system of the present invention provides a clinician with the ability manipulate the adjustable portion of the distal section, particularly when the adjustable portion is in the pre-defined arcuate shape, thereby providing an increased overall range of motion to allow improved manipulation during navigation of a vessel. Thus, the access system of the present invention provides access to the appropriate vessel (e.g., biliary duct), allows manipulation of the catheter, as well as other tools (e.g., guidewire) into position so as to achieve trans-papillary placement (across the ampulla of Vater), and further achieve internal drainage of the biliary duct (e.g., via placement of a stent), all without having to perform a scope exchange (as current techniques require US scope to ERCP scope exchanges during rendezvous procedure for biliary duct drainage).

The access system of the present invention overcomes many of the drawbacks associated with the EUS/ERCP rendezvous technique. In particular, the pre-defined arcuate shape of the access catheter of the present invention provides improved initial access to the biliary duct, due in part to the initial trans-duodenal puncture, which occurs in a relatively orthogonal angle to the lumen of the biliary duct. Accordingly, upon initially accessing the biliary duct with the catheter, the pre-defined arcuate shape of the distal section results in the distal end of the catheter being aligned with the lumen of the biliary duct, such that guidewire advancement is improved and decreases the risk of injury to surrounding tissue when advancing a guidewire. Furthermore, the increased mobility of the access catheter, particularly the increased flexibility of the distal end, as well as improved manipulation of the distal end, not only in a rotational manner, but also in left, right, front, and back directions relative to the longitudinal axis of the catheter, improves the clinician's ability to navigate the lumen of the duct, and further advance past obstructions that may have been otherwise impassable with conventional catheters used in EUS/ERCP rendezvous technique.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A system for providing access to a vessel, the system comprising:
an adjustable delivery handle system comprising:
a delivery handle assembly, at least a portion of which comprises an inner lumen configured to receive one of a plurality of exchangeable subassemblies; and
an inner hub housing coupled to a portion of the deliver handle assembly, the inner hub housing having a first plurality of radially-spaced barbs disposed on an inner diameter thereof;
a sheath coupled to a distal end of the handle assembly and having a lumen in fluid communication with the inner lumen of the delivery handle assembly; and
an access catheter subassembly removably disposed within the inner lumen of the delivery handle assembly and lumen of the sheath, the access catheter subassembly comprising:
a catheter hub configured for insertion into the inner hub housing, the catheter hub having a second plurality of radially-spaced barbs disposed on an outer diameter thereof, wherein each of the second plurality of radially-spaced barbs are configured for selective engagement with a corresponding one of the first plurality of radially-spaced barbs to permit incremental rotation of the catheter hub relative to the inner hub housing; and
an access catheter having an elongate tubular catheter body having a proximal section having a proximal end, a distal section having a distal end, an outer surface, and an inner surface defining a lumen extending from the proximal end to the distal end,
wherein the distal section of the access catheter is configured to incrementally rotate about a longitudinal axis defined by the lumen of the catheter body in conjunction with incremental rotation of the catheter hub.

2. The system of claim 1, wherein the distal section includes an adjustable portion along a length thereof configured to transition to a pre-defined arcuate shape.

3. The system of claim 2, wherein, when disposed within the lumen of the sheath, the adjustable portion of the distal section of the access catheter is configured to maintain a substantially linear shape.

4. The system of claim 2, wherein, upon extension from the lumen of the sheath, the adjustable portion of the distal section of the access catheter is configured to transition to the pre-defined arcuate shape.

5. The system of claim 2, wherein, when in the pre-defined arcuate shape, the adjustable portion forms at least one angle relative to the longitudinal axis defined by the lumen of the catheter body, wherein the at least one angle is between 0 and 170 degrees.

6. The system of claim 2, further comprising a stylette member removably disposed within the inner lumen of the delivery handle assembly, lumen of the sheath, and lumen of the access catheter, the stylette member having a distal end configured to pierce tissue of the vessel to provide access to an interior of the vessel.

7. The system of claim 6, wherein the adjustable portion is configured to maintain a substantially linear shape when the stylette member is disposed within a lumen of the adjustable portion of the distal section of the access catheter.

8. The system of claim 7, wherein the adjustable portion is configured to transition to the pre-defined arcuate shape upon removal of the stylette member from within the lumen of the adjustable portion.

9. The system of claim 1, wherein the proximal section and the distal section of the access catheter have different levels of stiffness.

10. The system of claim 9, wherein the proximal section has a greater level of stiffness than the distal section.

11. The system of claim 1, wherein the distal section of the access catheter further comprises a portion adjacent the distal end having enhanced echogenicity or acoustic reflection.

12. The system of claim 1, wherein the distal section of the access catheter has a metallic distal tip.

13. The system of claim 1, wherein the distal section of the access catheter comprises a tubular body formed from densely packed tubular coil.

14. The system of claim 13, wherein an interior surface of the lumen of the distal section has a liner disposed thereon having a coefficient of friction.

15. The system of claim 1, wherein the access catheter further comprises a cutting element positioned on the distal section adjacent to the distal end.

16. The system of claim 1, wherein the access catheter further comprises at least one control element configured to cause movement of at least the distal end relative to the longitudinal axis defined by the lumen of the catheter body upon application of force thereto.

* * * * *